United States Patent
Mudde

(10) Patent No.: US 10,434,170 B2
(45) Date of Patent: Oct. 8, 2019

(54) IMMUNOREGULATORY VACCINE

(71) Applicant: S-TARGET THERAPEUTICS GMBH, Vienna (AT)

(72) Inventor: Geert Mudde, Breitenfurt (AT)

(73) Assignee: S-TARGET THERAPEUTICS GMBH, Vienna (AT)

( * ) Notice: Subject to any disclaimer, the term of this patent is extended or adjusted under 35 U.S.C. 154(b) by 812 days.

(21) Appl. No.: 14/414,337

(22) PCT Filed: Jul. 2, 2013

(86) PCT No.: PCT/EP2013/063959
§ 371 (c)(1),
(2) Date: Jan. 12, 2015

(87) PCT Pub. No.: WO2014/009209
PCT Pub. Date: Jan. 16, 2014

(65) Prior Publication Data
US 2015/0196636 A1    Jul. 16, 2015

(30) Foreign Application Priority Data

Jul. 13, 2012  (EP) .................................. 12176348.6
Mar. 8, 2013   (EP) .................................. 13158410.4
May 21, 2013   (EP) .................................. 13168578.6

(51) Int. Cl.
| | |
|---|---|
| *A61K 39/39* | (2006.01) |
| *A61K 39/00* | (2006.01) |
| *A61K 39/36* | (2006.01) |
| *A61K 39/35* | (2006.01) |

(52) U.S. Cl.
CPC ............ *A61K 39/39* (2013.01); *A61K 39/001* (2013.01); *A61K 39/0003* (2013.01); *A61K 39/0005* (2013.01); *A61K 39/0008* (2013.01); *A61K 39/0011* (2013.01); *A61K 39/35* (2013.01); *A61K 39/36* (2013.01); *A61K 2039/505* (2013.01); *A61K 2039/55516* (2013.01); *A61K 2039/55561* (2013.01); *A61K 2039/577* (2013.01); *A61K 2039/6031* (2013.01); *A61K 2039/64* (2013.01)

(58) Field of Classification Search
None
See application file for complete search history.

(56) References Cited

U.S. PATENT DOCUMENTS

| 5,023,077 A | 6/1991 | Gevas et al. |
| 5,609,870 A | 3/1997 | Gevas et al. |
| 8,580,274 B2 | 11/2013 | Arakawa et al. |
| 2012/0100165 A1 | 4/2012 | Arakawa et al. |

FOREIGN PATENT DOCUMENTS

| EP | 0178085 A1 | 4/1986 |
| EP | 0287361 A2 | 10/1988 |
| EP | 2 397 547 A1 | 12/2011 |
| WO | 97/07218 | 2/1997 |
| WO | WO 2007/098934 A1 | 9/2007 |
| WO | 2010092963 A1 | 8/2010 |

OTHER PUBLICATIONS

Ngo et al. 'Computational Complexity, Protein Structure Prediction, and the Levinthal Paradox'. The Protein Folding Problem and Tertiary Structure Prediction. Ed. K. Merz and S. Le Grand. Boston: Birkhauser, 1994.491-495.*
Skolnick et al. 'From genes to protein structure and function: novel applications of computational approaches in the genomic era.' Trends in Biotech. 18:34-39, 2000.*
Attwood et al. 'The Babel of Bioinformatics.' Science. 290(5491):471-473.*
Blumenthal et al. 'Definition of an Allergen.' Allergens and Allergen Immunotherapy. Ed. R Lockey, S. Bukantz and J. Bousquet. New York: Marcel Decker, 2004.37-50.*
Kuby Immunology, 4th Edition, Chapter 18, "Vaccines," pp. 449-465 (2001).*
Mukherjee et al. 'Allergic Asthma: Influence of Genetic and Environmental Factors.' J. Biol. Chem. 286(38):32883-32889, 2011.*
Kurucz etal. 'Current Animal Models of Bronchial Asthma.' Curr. Pharm. Des. 12:3175-3194, 2006.*
Lupas et al, "The Structure of x-Helical Coiled Coils", Adv Protein Chem., 2005, 70:37-78.
International Preliminary Report on Patentability for International Patent Application No. PCT/EP2013/063959, dated Jan. 13, 2015; 9 pages.
Mudde,G.C., F.C.Van Reijsen, G.J.Boland, G.C.De Gast, P.L.B. Bruijnzeel, and C.A.F.M.Bruijnzeel-Koomen, Allergen presentation by epidermal Langerhans' cells from patients with atopic dermatitis is mediated by IgE, Immunology, 69:335-341 (1990).
K. Arndt, et al. "Helix-stabilized Fv (hsFv) Antibody Fragments: Substituting the Constant Domains of a Fab Fragment for a Heterodimeric Coiled-coil Domain." J Mol Biol 312, 2001, pp. 221-228, Academic Press.
H. Chao, et al. "Use of a heterodimeric coiled-coil system for biosensor application and affinity purification." Journal of Chromatography B, 715, 1998, pp. 307-329.
R. Ashman, et al. "Optical oligonucleotide sequences for TLR9 inhibitory activity in human cells: lack of correlation with TLR9 binding." The Japanese Society for Immunology, 2011, vol. 23, No. 3 pp. 203-214.

(Continued)

*Primary Examiner* — Nora M Rooney
(74) *Attorney, Agent, or Firm* — Loza & Loza, LLP; Michael F. Fedrick

(57) ABSTRACT

An immune-regulatory vaccine comprising—a directed adjuvant comprising at least an anti-CD32 moiety linked to a TLR9 ligand and a first peptidic alpha-helix, and—an immunogen with at least one epitope and a second peptidic alpha-helix coiled to the first alpha-helix, a kit for preparing the vaccine, and a sensibilizing vaccine comprising at least an anti-CD32 moiety linked to a TLR9 ligand and a peptidic alpha-helix in a pharmaceutical formulation.

Figure 1:
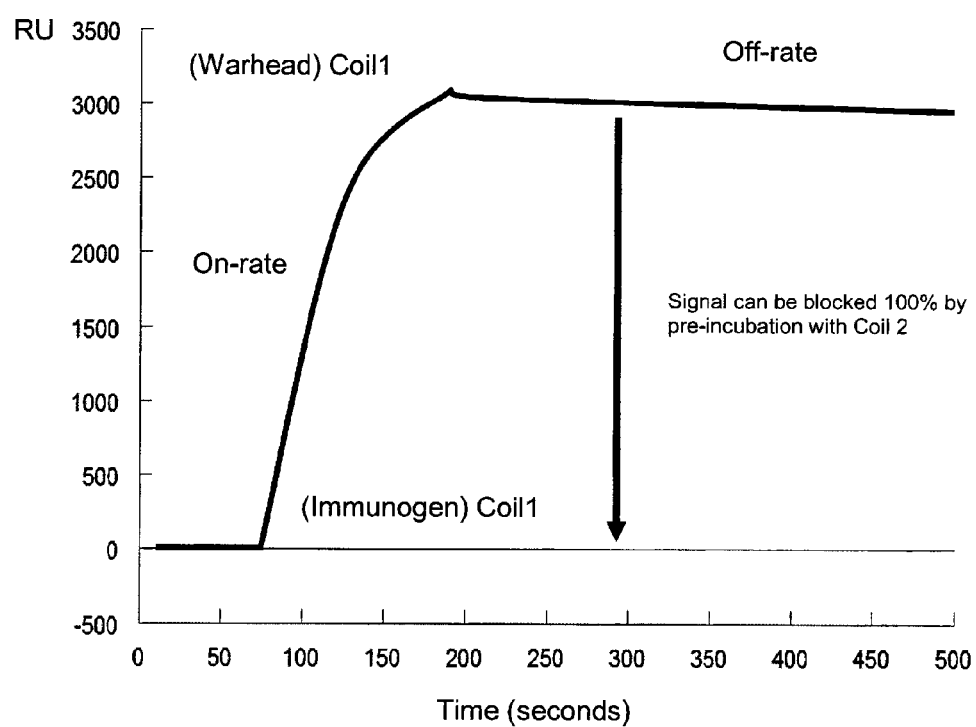

13 Claims, 13 Drawing Sheets
Specification includes a Sequence Listing.

(56) References Cited

OTHER PUBLICATIONS

M. Cheever, et al. "Provenge (Sipuleucel-T) in Prostate Cancer: The First FDA-Approved Therapeutic Cancer Vaccine." Clinical Cancer Research, 2011, Apr. 6, 2011, vol. 17, pp. 3520-3526.
G. Berntzen, "Identification of a High Affinity Fcgamma RIIA binding peptide that distinguishes Fcgamma RIIA from Fcgamma RIIB and exploits Fcgamma RIIA mediated phagocytosis and degradation." The Journal of Chemistry vol. 284, No. 2, Jan. 9, 2009, pp. 1126-1135.
G. Ciccotosto, et al. "Gastrin Processing and Secretion in Patients with End-Stage Renal Failure." Journal of Clinical Endocrinology and Metabolism, 1996, pp. 3231-3238, vol. 81, No. 9.
K. Abel, et al. "Deoxycytidyl-Deoxyguanosine Oligonucleotide Classes A, B, and C Induce Distinct Cytokine Gene Expression Patterns in Rhesus Monkey Peripheral Blood Mononuclear Cells and Distinct Alpha Interferon Responses in TLR9-Expressing Rhesus Monkey Plasmacytoid Dendritic Cells." Clinical and Diagnostic Laboratory Immunology, May 2005, pp. 606-621, vol. 12, No. 5.
B.T Brett, et al. "Phase II Study of Anti-Gastrin-17 Antibodies, Raised to G17DT, in Advanced Pancreatic Cancer" Journal of Clinical Oncology, Oct. 15, 2002, vol. 20, No. 20, pp. 4225-4231.
M. Daëron, et al. "Regulation of High-affinity IgE Receptor-medicated Mast Cell Activation by Murine Low-affinity IgG Receptors." The American Society for Clinical Investigation, Inc. Feb. 1995, vol. 95, pp. 577-585.
A. Krieg, et al. "CpG motifs in bacterial DNA trigger direct B-cell activation." Letters to Nature, Apr. 6, 1995, pp. 546-549, vol. 374.
J. R. Litowski, et al. "Designing heterodimeric two-stranded x-helical coiled-coils: the effect of chain length on protein folding, stability and specificity." J. Pept. Res. 58, pp. 477-492.
A. Bassiri, et al. "Toll-Like Receptor 9 Can Be Expressed at the Cell Surface of Distinct Populations of Tonsils and Human Peripheral Blood Mononuclear Cells." Infection and Immunity, Dec. 2004, pp. 7202-7211.
A. Krug, et al. "Identification of CpG oligonucleotide sequences with high induction of IFN-a/β in plasmacytoid dendritic cells." Eur. J. Immunol. 2001, 31, pp. 2154-2163.
R. Looney, et al. "Human Monocytes and U937 Cells Bear Two Distinct Fc Receptors for IgG1." The Journal of Immunology, vol. 136. No. 5, Mar. 1, 1986 pp. 1641-1647, Rochester, NY.
J. Greenman, et al. "Characterization of a New Monoclonal Anti-Fcy RII Antibody, AT10, and Its Incorporation into a Bispecific F (ab')₂ Derivative for Recruitment of Cytotoxic Effectors." Molecular Immunology, 1991 vol. 28, No. 11, pp. 1243-1254, Great Britain.
A. Linley, et at. "Tumor-assoicated antigens: considerations for their use in tumour immunotherapy." The Japanese Society of Hematology, Feb. 1, 2011, 93, pp. 263-273, School of Science and Technology, Nottingham Trent University, Clifton Lane, Nottingham UK.
J. Lund, et al. "Toll like Receptor 9-mediated Recognition of Herpes Simplex Virus-2 by Plasmacytoid Dendritic Cells." The Journal of Experimental Medicine, vol. 198, No. 3, Aug. 4, 2003, pp. 513-520.
G. Hartmann, et al. "Rational design of new CpG oligonucleotides that combine B cell activation with high IFN-a induction in plasmacytoid dendritic cells." Eur. J. Immunol. 2003. 33, pp. 1633-1641.
J. Litowski, et al. "Designing Heterodimeric Two-stranded alpha-Helical Coiled-coils." The Journal of Biological Chemistry, Oct. 4, 2002, vol. 277, No. 40, pp. 37272-37279.
E. Macintyre, et al. "Mechanism of Human Monocyte Activation Via the 40-kDa Fc Receptor for IgG." The Journal of Immunology, Dec. 15, 1988, vol. 141, No. 12, pp. 4333-4343.
D. Mathis, et al. "Back to Central Tolerance" Immunity, May 2004, vol. 20, pp. 509-516.

M. Morton, et al. "Targeting gastrin for the treatment of gastric acid related disorders and pancreatic cancer" Trends in Pharmacological Sciences, Apr. 2011, vol. 32, No. 4 pp. 201-205.
D. Maurer, et al. The High Affinity IgE Receptor (FceRI) Mediates IgE-Dependent Allergen Presentation1, The American Association of Immunologists, J. Immunol. 1995, pp. 6285-5290.
G. Mudde, et al. "Antigen presentation in allergic sensitization" Immunology and Cell Biology, Jan. 8, 1996, 74 pp. 167-173.
J. Miller, "Peripheral T Cell Tolerance" Annu. Rev Immunol. 1992, 10, pp. 51-69.
J. Tversky, et al. "Subcutaneous Allergen Immunotherapy Restores Human Dendritic Cell Innate Immune Function" Clinical Exp Allergy, Jan. 2010.
F. Van Reijsen, et al. "Skin-derived aeroallergen-specific T-cell clones of Th2 phenotype in patients with atopic dermatitis" J. Allergy Clin. Immunol, Aug. 1992, pp. 184-193, vol. 90 No. 2.
S.A. Watson, et al. "Potential role of endocrine gastrin in the colonic adenoma carcinoma sequence" British Journal of Cancer, May 16, 2002, 87 pp. 567-573.
S.A. Watson, et al. "Antibodies Raised by Gastrimmune Inhibit the Spontaneous Metastasis of a Human Colorectal Tumour, AP5LV", European Journal of Cancer, vol. 35, No. 8 pp. 1286-1291.
G. Plitas, et al. "Toll-like receptor 9 inhibition reduces morality in polymicrobial sepsis" The Journal of Experimental Medicine, 2008, vol. 205 No. 6, pp. 1277-1283.
K. Saikh, et al. "Human Monocytes Infected with Yersinia pestis Express Cell Surface TLR9 and Differentiate into Dendritic Cells", The Journal of Immunology, Nov. 20, 2014, 173, pp. 7426-7434.
S. Stuart, et al. "Isolation and Expression of cDNA Clones Encoding a Human Receptor for IgG (FcyRII)", J. Exp. Med. vol. 166, Dec. 1987, pp. 1668-1684.
J. Tanaka, et al. "Functional cell surface expression of Toll-like receptor 9 promotes cell proliferation and survival in human hepatocellular carcinomas" International Journal of Oncology 37, Apr. 19, 2010, pp. 805-814.
M. Puig, et al. "Tlr9 and Tlr7 agonists mediate distinct type I IFN responses in humans and nonhuman primates in vitro and in vivo", Journal of Leukocyte Biology, Jan. 2012, vol. 91, pp. 147-158.
F. Sallusto, et al. "Efficient Presentation of Soluble Antigen by Cultured Human Dendritic Cells Is Maintained by Granulocyte/Macrophage Colony-stimulating Factor Plus Interleukin 4 and Downregulated by Tumor Necrosis Factor a" J. Exp Med. Apr. 1994, vol. 179; pp. 1109-1118.
A. Tafuri, et al. "T Cell Awareness of Paternal Alloantigens During Pregnancy" Science, Oct. 27, 1995, vol. 270, pp. 630-633.
J. Tel, et al. "Targeted delivery of CpG ODN to CD32 on human and monkey plasmacytoid dendritic cells augments IFN a secretion" Immunobiology 217, Jan. 18, 2012 pp. 1017-1024.
W. Rengifo-Cam, et al. "Role of Progastrins and Gastrins and Their Receptors in GI and Pancreatic Cancers: Targets for Treatment", Bentham Science Publishers Ltd. 2004, Current Pharmaceutical Design, 2004, vol. 10, No. 19 pp. 2345-2358.
L. Santamaria, et al. "Antigen Focusing by Specific Monomeric Immunoglobulin E Bound to CD23 on Epstein-Barr Virus-Transformed B Cells", 1993, Human Immunology 37, 23-30.
T. Takai, et al. "Augmented humoral and anaphylactic responses in FcyRII-deficient mice." Letters to Nature, Jan. 25, 1996, vol. 379, pp. 346-349.
Cendron, Angela C et al. "An FcyRIIa-binding peptide that mimics the interaction between FCyRIIa and IgG", ScienceDirect, Molecular Immunoloqhy 45, pp. 307-319 (2008).
First Office Action in co-pending JP Application No. 2015-520903, dated Aug. 8, 2017, 3 pages.
Response to Office Action in co-pending EP Application No. 13732967.8, dated Oct. 17, 2018, 8 pages.

\* cited by examiner

Figure 12:

SEQ ID 78:
pEGPWLEEEEE AYGWMDF

SEQ ID 79:
pEGPWLEEEEEAY

SEQ ID 80:
pEXPX
Wherein
X at position 2, 4 is any amino acid.

SEQ ID 81:
pEXPX
Wherein
X at position 2 is any of G or R;
X at position 4 is any of W or R SEQ ID 82:
pEXPXXEEEEXAY
Wherein
X at position 2, 4, 5 or 10 is any amino acid.

SEQ ID 83:
pEXPXXEEEEXAY
Wherein
X at position 2 is any of G or R;
X at position 4 is any of W or R;
X at position 5 is any of L or M; and
X at position 10 is any of E or A.

Figure 12 (cont.):

SEQ ID 84:
pEXPXXEEEEXAYG
Wherein
X at position 2, 4, 5 or 10 is any amino acid.

SEQ ID 85:
pEXPXXEEEEXAYG
Wherein
X at position 2 is any of G or R;
X at position 4 is any of W or R;
X at position 5 is any of L or M; and
X at position 10 is any of E or A.

SEQ ID 86:
pEGPWLEEEEEAYG

SEQ ID 87:
pEGPWLEEEEEAYGGGSGG<u>KVSALKEKVSALKEKVSALKEKVSALKEKVSALKE</u>
bold is the peptide immunogen, *italic is linker*, <u>underlined is coil</u>

SEQ ID 88:
pEGPWLEEEEEAYGGG
              K*GGSGG*<u>KVSALKEKVSALKEKVSALKEKVSALKEKVSALKE</u>
pEGPWLEEEEEAYGGG
bold is the peptide immunogen, *italic is linker*, <u>underlined is coil</u>

SEQ ID 89:
GGSGG

SEQ ID 90:
GG
  |
  KGGSGG
  |
GG

IMMUNOREGULATORY VACCINE

The invention refers to an immunoregulatory vaccine comprising an immunogen and a directed adjuvant linked thereto, thereby modulating the immune response to the immunogen. The invention further refers to a vaccine comprising an immunogenic composition comprising
a directed adjuvant comprising at least an anti-CD32 moiety linked to a TLR9 ligand, and
an immunogen, which is bound to the directed adjuvant,
for use in treating a subject for eliciting a transient IgG immune response directed to the immunogen.

BACKGROUND

For immune diseases including allergy, cancer, and autoimmune diseases there is a pivotal role of regulation for the immune balance regulated by Th1/Th2/Th17/Treg cells and its application to development of novel immune therapies.

Th1 cells, (Type 1 helper T cells) are characterized by the production of proinflammatory cytokines like IFN-γ, IL-2, and TNF-β. Th1 cells are involved in cell-mediated immunity. The cytokines produced by Th1 cells stimulate the phagocytosis and destruction of microbial pathogens. Several chronic inflammatory diseases have been described as Th1 dominant diseases i.e. multiple sclerosis, diabetes, and rheumatoid arthritis.

Th2 cells (Type 2 helper T cells) are characterized by the production of IL-4, IL-5, IL-9, IL-10, and IL-13. Th2 cells are thought to play a role in allergy responses. Cytokines like IL-4 generally stimulate the production of antibodies. IL-5 stimulates eosinophil responses, also part of the immune response. Atopy and allergy are thought to be Th2 dominant conditions.

The imbalance of Th1/Th2 or Th17/Treg immunity becomes the cause of various immune diseases.

Allergy is considered to be a hypersensitive reaction to proteins in the environment. Allergens are antigens to which atopic patients respond with IgE antibody responses subsequently leading to allergic reactions. Antigens in the complexes or fusion proteins can be environmental allergens (e.g. house dust mite, birch pollen, grass pollen, cat antigens, cockroach antigens), or food allergens (e.g. cow milk, peanut, shrimp, soya), or a combination of both. IgE molecules are important because of their role in effector cell (mast cell, basophiles and eosinophiles) activation. It is generally accepted that IgE also plays an important role in the induction phase of allergic diseases, by up-regulating the antigen capture potential of B cells and dendritic cells (DC), both through low affinity (CD23) and high affinity receptors (FcεRI). The negative functions of IgE antibodies can be counteracted by allergen specific IgG antibodies. e.g. because they direct the immune response away from B cells to monocytes and DC and they are able to down regulate IgE receptor mediated activation of effector cells through co-cross linking the FcεRI with FcγRIIb (CD32b) on these cells. In addition, they compete with IgE molecules for allergen binding sites. Allergies therefore can be treated, cured and prevented by the induction of allergen specific IgG molecules especially IgG1.

IgG molecules have a serum half-life of approximately 3 weeks as compared to roughly 3 days for IgE molecules. IgE molecules are induced by the interaction between (naïve) B cells and Th2 cells which provide the IL-4 and IL-13 together with CD40L expression necessary to induce a class switch to IgE in memory B cells and plasma cells. In contrast, Th1 cells, which produce IFN-γ and IL-2, induce a class switch to IgG. Therefore, induction of Th1, rather than Th2 helper T cell responses against allergens, is beneficial for the prevention, treatment and cure of allergic diseases.

To date several forms of active vaccination using allergens are used. The most common is the so called “immunotherapy”, which depends on frequent immunizations with relatively high concentrations of allergens. This technique is only moderately effective in a minority of allergic diseases such as bee venom allergy and in some cases of rhinitis and conjunctivitis, and recently some reports have shown effectiveness in milder forms of asthma and atopic dermatitis. More recently rush immunotherapy, where increasing amounts of allergen are injected in a rather short time frame, has been applied with slightly better results. Usually the subcutaneous route is used for administration of the allergens, but recently this route has been compared to oral application or even local application, the results are generally positive but not always consistent. A different technique for immunotherapy is the one described by Saint-Remy (EP0178085 and EP0287361), which makes use of autologous IgG antibodies which are in vitro complexed to the relevant allergens. This technique allows far smaller amounts of allergen to be applied with fewer side effects.

The mechanism behind these therapies is unclear. In the classical therapy there seems to be a beneficial effect if the therapy induces an increase in specific IgG antibodies, although not every significant increase of specific IgG is correlated with successful immunotherapy. A possible argument why this is the case is the relatively low affinity of IgG antibodies for CD32 on B cells, monocytes and mast cells. The Saint-Remy approach selects the specific IgG antibodies from the patient, which are subsequently mixed with relevant allergens in vitro. This way they assure that the allergen cannot react freely with cells or other antibody isotypes on cells such as IgE on mast cells. In addition they claim that anti-idiotypic antibodies are raised against the specific IgG molecules, which in the future will prevent allergy.

In WO 97/07218 Allergen-anti-CD32 Fusion Proteins are described. In this publication the problems with isolating specific IgG molecules and the low affinity of these IgG antibodies for CD32 are circumvented and the risk factors of classical immunotherapy, which uses complete “IgE binding” allergens, are reduced. However, the claimed induction of Th1 memory responses due to solely directing the anti-CD32 containing vaccine to dendritic cells is not substantiated.

WO2007098934A1 describes molecules capable of binding to TLR9 and to CD32 comprising at least one epitope of at least one antigen, its production and its use as medicament, especially for the treatment of allergies.

Immunoregulation may work not only in the case of allergic diseases, but also in a series of other diseases.

Enhancing the immune response to infectious agents, such as microbial pathogens, is the goal of prophylactic or therapeutic anti-infectious immunotherapy.

In tumor immunotherapies there is also the goal to use tumor antigen specific T helper type 1 (Th1) cells in addition to cytotoxic T lymphocytes (CTL).

Cancer known medically as a malignant neoplasm, is a broad group of various diseases, all involving unregulated cell growth. In cancer, cells divide and grow uncontrollably, forming malignant tumors, and invade nearby parts of the body. The cancer may also spread to more distant parts of the body through the lymphatic system or bloodstream. Not all tumors are cancerous. Benign tumors do not grow uncontrollably, do not invade neighboring tissues, and do not spread throughout the body. There are over 200 different known cancers that afflict humans.

Determining what causes cancer is complex. Many things are known to increase the risk of cancer, including tobacco use, certain infections, radiation, lack of physical activity, obesity, and environmental pollutants. These can directly damage genes or combine with existing genetic faults within cells to cause the disease. Approximately five to ten percent of cancers are entirely hereditary.

Cancer can be detected in a number of ways, including the presence of certain signs and symptoms, screening tests, or medical imaging. Once a possible cancer is detected it is diagnosed by microscopic examination of a tissue sample. Cancer is usually treated with chemotherapy, radiation therapy and surgery. The chances of surviving the disease vary greatly by the type and location of the cancer and the extent of disease at the start of treatment. While cancer can affect people of all ages, and a few types of cancer are more common in children, the risk of developing cancer generally increases with age. In 2007, cancer caused about 13% of all human deaths worldwide (7.9 million). Rates are rising as more people live to an old age and as mass lifestyle changes occur in the developing world.

Since the immune system responds to the environmental factors it encounters on the basis of discrimination between self and non-self, many kinds of tumor cells that arise as a result of the onset of cancer are more or less tolerated by the patient's own immune system since the tumor cells are essentially the patient's own cells that are growing, dividing and spreading without proper regulatory control.

Immune tolerance or immunological tolerance is the process by which the immune system does not attack an antigen. In natural or self-tolerance, the body does not mount an immune response to self-antigens. It occurs in three forms: central tolerance, peripheral tolerance and acquired tolerance Central Tolerance[1]:

Central tolerance occurs during lymphocyte development and operates in the thymus and bone marrow. Here, T and B lymphocytes that recognize self-antigens are deleted before they develop into fully immunocompetent cells, preventing autoimmunity. This process is most active in fetal life, but continues throughout life as immature lymphocytes are generated.

Peripheral Tolerance[2]:

Peripheral tolerance is immunological tolerance developed after T and B cells mature and enter the periphery. The T cells that leave the thymus are relatively but not completely safe. Some will have receptors (TCRs) that can respond to self-antigens that are present in such high concentration that they can bind to "weak" receptors the T cell did not encounter in the thymus (such as, tissue-specific molecules like those in the islets of Langerhans, brain or spinal cord). Those self-reactive T cells that escape intrathymic negative selection in the thymus can inflict cell injury unless they are deleted or effectively muzzled in the peripheral tissue. Several feedback mechanism to silence such potentially auto reactive T cells are known to exist. They include following: Anergy, Activation-induced cell death, Peripheral suppression Acquired or Induced Tolerance[3]:

Acquired or induced tolerance refers to the immune system's adaptation to external antigens characterized by a specific non-reactivity of the lymphoid tissues to a given antigen that in other circumstances would likely induce cell-mediated or humoral immunity. One of the most important natural kinds of acquired tolerance is immune tolerance in pregnancy, where the fetus and the placenta must be tolerated by the maternal immune system.

Immunotherapy Targeting Tumor Associated Antigens:

Cancer immunotherapy is the use of the immune system to reject cancer. The main premise is stimulating the patient's immune system to attack the malignant tumor cells that are responsible for the disease. This can be done either through active immunization of the patient (e.g., by administering a cellular cancer vaccine, such as Provenge, Dendreon, Seattle, Wash., US)[4], in which case the patient's own immune system is trained to recognize tumor cells as targets to be destroyed, or through the administration of therapeutic antibodies as drugs, in which case the patient's immune system is recruited to destroy tumor cells by the therapeutic antibodies. Another approach for activating the patient's immune system against tumors is to make use of so called tumor associated antigens (TAA's), which are self-proteins which are to some extend expressed on healthy normal cells, but overexpressed on tumor cells or they comprise of cell hormones/growth factors to which the tumor cells proliferate[5]. These TAAs are formulated and presented to the body in an immunogenic fashion such that the immune system will build a response despite the fact that these proteins are self. Obviously this approach will only be useful for TAAs against which the patient has developed peripheral or acquired tolerance. When the T and B cells recognizing the TAA have been deleted from the immunological repertoire, active cancer immunotherapy is not an option.

Gastrin:

An example of an autoantigen (hormone/growth factor) that may be used as target for treatment of gastro intestinal cancers such as pancreatic cancer is little gastrin (G17)[6-9]. In addition, neutralization of G17 may also be beneficial in any gastrin related disease condition, including gastric ulcers, Gastro Esophageal Reflux Disease (GERD)[10], since the pH of the stomach is regulated by gastrin, and for End Stage Renal Failure (ESRF)[11], since gastrin circulates at higher than normal concentrations in ESRF patients.

U.S. Pat. No. 5,023,077 describes immunogenic compositions and methods for the treatment and prevention of gastric and duodenal ulcer disease, which immunogenic compositions are based on gastrin peptides, which are coupled to an immunogenic carrier, such as diptheria toxoid, tetanus toxoid, keyhole limpet hemocyanin or bovine serum albumin.

Gastrin has several important functions in the gastrointestinal tract, the two most important being stimulation of acid secretion and stimulation of the growth of cells in the gastrointestinal tract. The hormone exists in at least two molecular forms, heptadecagastrin, the so-called little gastrin ("G17"), and tetratriacontagastrin ("G34") named according to the number of amino acid residues ("AA's") in each molecule, wherein the G17 constitutes the 17 amino terminal ("N-terminal") residues of G34.

U.S. Pat. No. 5,609,870 describes the preparation of an anti-G17 immunogen which raises antibodies in a mammal against its own G17 which do not react with G34 comprising conjugating a peptide which consists of a sequence corresponding to a fragment of the N-terminal amino acid sequence of G17 up to amino acid residue number 12 by its C-terminus to a spacer peptide which is conjugated to an immunogenic carrier, such as diphtheria toxoid, tetanus toxoid, keyhole limpet hemocyanin, and bovine serum albumin.

Immune Balance:

The immune balance regulated by Th1/Th2/Th17/Treg cells plays a significant part in the development of immune therapies.

In autoimmune diseases there is a need to regulate the Th1/Th2/Th17/Treg imbalance, i.e. in conditions where the immune system attacks self-tissue.

The Role of TLR9:

Toll-like receptors (TLRs) are a class of proteins that play a key role in the innate immune system. They are single, membrane-spanning, non-catalytic receptors usually expressed on the cell surface and in the endocytic compartment of sentinel cells such as macrophages and dendritic cells. TLR's recognize pathogen-associated molecular patterns (PAMPs), structurally conserved molecules, derived from microbes and initiate signalling to induce production of cytokines necessary for the innate immunity and subsequent adaptive immunity.

The various TLRs exhibit different patterns of expression. This gene is preferentially expressed in immune cell rich tissues, such as spleen, lymph node, bone marrow and peripheral blood leukocytes.

Thirteen TLRs (named simply TLR1 to TLR13) have been identified in humans and mice together, and equivalent forms of many of these have been found in other mammalian species. However, not every TLR receptor in mice is also found in humans or vice versa. In addition, not for every TLR receptor the ligand and function is known, e.g. TLR10 is orphan receptor with unknown function.

Activation of TLR receptors has been used for the treatment of various diseases e.g activation of TLR9 by pharmaceutical products has been shown to be beneficial in treatment of allergy and oncology. Studies in mice and human indicate that the natural ligands of TLR9 are unmethylated CpG sequences in DNA molecules. CpG sites are relatively rare (~1%) on vertebrate genomes in comparison to bacterial genomes or viral DNA. TLR9 is expressed by numerous cells of the immune system such as dendritic cells, B lymphocytes, monocytes and natural killer (NK) cells. However in healthy humans the TLR9 is expression is restricted to plasmacytoid dendritic cells (pDCs) and B cells. The expression is intracellularly, within the endosomal compartments and functions to alert the immune system of viral and bacterial infections by binding to DNA rich in CpG motifs. However under pathological conditions TLR9 expression has been reported on the cell surface of cells as well[12-14].

Many different synthetic TLR9 agonist molecules have been reported. The agonistic ligands (TLR9 activating) have been classified into three groups:

The group consisting of CpG class A, in particular CpG-A (D)[15] oligodeoxynucleotides (ODN), also known as "D"-type ODN. Such TLR9 agonists induce a strong IFNa induction and minimal maturation of dendritic cells, and are herein called "group 1" TLR9 ligand. An example is ODN2216[16]:

GGGGGACGATCGTCGGGGGG (SEQ ID 48)

The group consisting of CpG class B, in particular CpG-B (K)[17] oligodeoxynucleotides (ODN), also known as "K"-type ODN. Such TLR9 agonists induce a weak IFNa induction and maturation of dendritic cells, and are herein called "group 2" TLR9 ligand. An example is ODN2006[18;19]:

TCGTCGTTTTGTCGTTTTGTCGTT (SEQ ID 49)

The group consisting of CpG class C, also known as CpG-C[20] oligodeoxynucleotides (ODN). Such TLR9 agonists induce IFNa and maturation of immature dendritic cells, and are herein called "group 3" TLR9 ligand. An example is ODNM362[21]:

TCGTCGTCGTTCGAACGACGTTGAT (SEQ ID 69)

All of the ligands for TLR9 described to date are based on nucleotides. Although antibodies specific for TLR9 have been reported and used to demonstrate the presence and location of the receptor, these molecules have not been described as ligands for TLR9, there was no report of any TLR9 activating or inhibiting activity.

The Role of CD32:

CD32 is strongly expressed on monocytes/dendritic cells and B cells and thus such molecules are designed to direct the immune response to these important immunological cells, with the intention to prevent antigen presentation by the B cells, while promoting antigen presentation by especially dendritic cells (DCs), the latter leads to induction of Th1 responses against the antigen, when sufficiently stimulated. There are at least two types of DCs: myeloid (mDC) and plasmacytoid dendritic cells (pDC), which has led to the new concept of DC1 and DC2 cells. In this concept DC1 cells promote the induction of Th1 cell development after antigen specific stimulation and DC2 cells support the development of Th2 cells. Monocyte derived DC (or mDC) are generally considered to be of DC1 type, whereas pDC are considered to be DC2 type. Both types of DC express CD32a and will induce an antigen specific T cell response; however it is not guaranteed that the outcome will be of Th1 type. In fact, in allergic donors Th2 responses are more likely. Importantly, the pDC express the TLR9 receptor, which binds CpG-ODNs (oligodeoxynucleotides (ODNs) containing unmethylated CpG motifs). Activation of this receptor in the pDC leads to a very strong production of IFN-alpha and IL-12, which promotes Th1 induction and thus transforms the potential DC2 into DC1 cells.

Thus, such molecules can combine the activation of the TLR9 receptor in pDC with the specific stimulation and induction of antigen specific Th1 cells.

In tumor immunotherapies there is the particular goal to use tumor antigen specific T helper type 1 (Th1) cells in addition to cytotoxic T lymphocytes (CTL).

Coiled Coils:

Coiled coils are consisting of structural motifs in proteins, in which 2-7 alpha-helices are coiled together like the strands of a rope; dimers and trimers are the most common types. The coiled coil helixes have been used to stabilize Fv antibody fragments resulting in heterodimeric coiled-coil domains[22].

The stability and folded structure of complex proteinaceous molecules is crucial when designing immunogens. It is thus the object of the invention to provide a vaccine with improved stability and structure to regulate the immune response to specific immunogens.

There is further a need to provide improved immunotherapies targeting gastrin and gastrin dependent disease conditions. It is thus the object of the invention to provide a vaccine with improved immunogenicity, stability and structure to regulate the immune response to specific gastrin epitopes.

SUMMARY OF THE INVENTION

The object is solved by the subject matter as claimed.

According to the invention there is provided an immunoregulatory vaccine comprising
- a directed adjuvant comprising at least an anti-CD32 moiety linked to a TLR9 ligand and a first peptidic alpha-helix, and
- an immunogen with at least one epitope and a second peptidic alpha-helix coiled to the first alpha-helix.

Specifically the epitope is a T cell and/or B cell epitope.

According to a specific aspect of the invention, each of said first and second alpha-helices comprises 3-5 amino acid repeats of an amino acid motive, specifically binding to each other with a Kd of less than $10^{-6}$ M, preferably with a Kd of less than $10^{-7}$ M, more preferred less than $10^{-8}$ M or $10^{-9}$ M.

According to a further specific aspect of the invention, said anti-CD32 moiety is selected from the group consisting of an anti-CD32 antibody, an antibody fragment and a peptide, preferably targeting CD32a. The antibody fragment specifically may e.g. be an Fab, Fv, scFv, dAb, F(ab)2 or Fcab fragment, or any other possible binding entity, as long as it specifically binds to the receptor and is internalized after binding.

According to another aspect of the invention, the TLR9 ligand is a TLR9 agonist selected from the group consisting of CpG class A, in particular CpG-A (D)[23] oligodeoxynucleotides (ODN), also known as "D"-type ODN. Such TLR9 agonists induce a strong IFNa induction and minimal maturation of dendritic cells, and are herein called "group 1" TLR9 ligand.

According to another aspect of the invention, the TLR9 ligand is a TLR9 agonist selected from the group consisting of CpG class B, in particular CpG-B (K)[24] oligodeoxynucleotides (ODN), also known as "K"-type ODN. Such TLR9 agonists induce a weak IFNa induction and maturation of dendritic cells, and are herein called "group 2" TLR9 ligand.

According to another aspect of the invention, said TLR9 ligand specifically is a TLR9 agonist selected from the group consisting of CpG class C, also known as CpG-C[25;26] oligodeoxynucleotides (ODN). Such TLR9 agonists induce IFNa and maturation of immature dendritic cells, and are herein called "group 3" TLR9 ligand.

According to another aspect of the invention, said TLR9 ligand specifically is an immunostimulatory peptide mimicking any of the CpG class A, B or C oligodeoxynucleotides, i.e. a peptide specifically binding to TLR9 with activating, agonistic function.

According to another aspect of the invention, the TLR9 ligand is a TLR9 antagonist selected from the group consisting of inhibitory ODNs[27;28] oligodeoxynucleotides (sometimes called inhibitory CPGs), e.g. those which contain the inhibitory motif consisting of CCx(not-C)(not-C) xxGGG (x=any base)[29]. Specific inhibitory ODNs have proven not to induce IFNa and not to induce maturation of dendritic cells, also blocking activation through an agonist of TLR9.

Such TLR9 agonist or antagonist can be determined in a suitable cell based assay, which measures stable expression of either of IFNa, or at least one of the markers CD80, CD83 and CD86, which reflect the maturation of immature dendritic cells (DC). For this purpose plasmacytoid dendritic cells (pDCs) are purified from blood of a healthy donor as described by Tel et al[30] and subsequently incubated with the appropriate concentration of the TLR9 ligand. After 24 h IFNa is measured in the supernatant using standard ELISA protocols. For determination of the maturation state of the cells, pDCs are stained for expression of CD80, CD83 or CD86 using standard FACS procedures with commercially available specific antibodies before and after the incubation with the TLR9 ligand.

The induction of IFNa may be determined by the level of IFNa expression and the respective increase with respect to a reference level. The increase relative to non-stimulated cells may be compared to the induction levels induced by established references for each type of CpG as defined by group 1, 2 or 3 TLR9 ligand and is typically between 30% and 300% of the respective reference, preferably at least 100%, more preferably at least 120%, at least 150%, at least 200% or at least 250%.

The maturation of immature dendritic cells may be determined by the level of expression of any of the markers CD80, CD83 and CD86. The respective increase relative to non-stimulated cells may be compared to the induction levels induced by established references for each type of CpG as defined by group 1, 2 or 3 TLR9 ligand and is typically between 30% and 300% of the respective reference, preferably at least 100%, more preferably at least 120%, at least 150%, at least 200% or at least 250%.

Specifically, the TLR9 agonist of group 1 and 3 would result in an increased IFNa expression and a TRL9 agonist of group 2 and 3 would lead to an increased expression of any of the DC maturation factors CD80, CD83 and CD86. The TLR9 antagonist would result in a reduced IFNa expression and a reduced expression of any of the DC maturation factors CD80, CD83 and CD86, even in the presence of a TLR9 agonist of either group 1-3.

According to a specific embodiment of the invention, the immunogen is derived from either
- a tumor associated-antigen, for use in the immunotherapy of cancer diseases, or
- a pathogen, for use in the immunotherapy of infectious diseases, or
- an allergen, for use in the immunotherapy of allergy diseases.

Such vaccine is typically an immunostimulating vaccine, e.g. stimulating the humoral and T-cell (Th1) immune response.

This embodiment of an immunostimulating vaccine specifically employs a TLR9 ligand which is a TLR9 agonist. In this case the vaccine predominantly induces Th1 responses against the immunogen.

Specifically said anti-CD32 moiety is targeting CD32a, preferably with a high affinity of Kd≤$10^{-6}$ M, more preferred less than $10^{-7}$ M or less than $10^{-8}$ M.

More specifically said anti-CD32 moiety is a specific or selective CD32a binder, i.e. not targeting CD32b or targeting CD32b with a low affinity of Kd>$10^{-6}$ M, preferably higher than $10^{-5}$ M, more preferred higher than $10^{-4}$ M. The differential affinity of binding to CD32a and CD32b is preferably at least 1 log, more preferred at least 2 logs or at least 3 logs, or higher difference in the Kd value.

The specifically preferred high affinity or high differential affinity of the anti-CD32 moiety to bind CD32a rather than CD32b is typically used in an immunostimulating vaccine further employing the TLR9 agonist. It is further preferred that such vaccine employs an immunogen selected from a series of oncology targets or pathogenic targets, where a Th1 response and specific IgG antibodies are necessary to effectively combat diseases.

According to an alternative embodiment, said anti-CD32 moiety is targeting both, CD32a and CD32b, with a high affinity of Kd $10^{-6}$ M, preferably higher affinity than $10^{-7}$ M, more preferred higher affinity than $10^{-5}$ M. The specifically preferred high affinity of the anti-CD32 moiety to bind both, CD32a and CD32b, is typically used in a vaccine further employing the TLR9 agonist. It is further preferred that such vaccine employs an immunogen selected from a series of allergy targets, where a redirection of a Th2 response to obtain a Th1 response is obtained. Typically, antibodies against the vaccine itself are not preferred. Further, a specific vaccine is preferred that binds to CD32b with about the same affinity as to CD32a.

Binding affinity of the anti-CD32 moiety targeting specifically any of CD32a or CD32b, or both, CD32a and CD32b, can be determined in a suitable assay such as a typical ELISA using commercially available HIS-tagged recombinant forms of CD32a and CD32b, coated to Ni-NTA ELISA plates, e.g. Ni-NTA HisSorb Plates (Qiagen, Austria). The anti-CD32 moieties may be biotinylated and as such may be detected using streptavidine-HRP or streptavidine AP and the appropriate substrates. Alternatively the moieties may be tested in a FACS assay using U937 cells (e.g. ATCC: CRL 1593) expressing CD32a but not CD32b and EBV transformed B cells e.g. CFB4:2 as described by van Reijsen et al[31], expressing CD32b and not CD32a.

According to further embodiment of the invention, the immunogen is derived from either

- an allergen, for use in the immunotherapy of allergy diseases, or
- a human auto-antigen, for use in the immunotherapy of autoimmune diseases Such vaccine for use in autoimmune disease is typically an immunotolerance vaccine, e.g. inducing T-cell tolerance against the immunogen by the regulatory T-cells and down-modulating the humoral immune response.

This embodiment of an immunotolerance specifically employs a TLR9 ligand which is a TLR9 agonist of group 1 or is a TLR9 antagonist. In this case the vaccine would predominantly down-regulate Th1/2/17 responses against the immunogen, but activate Treg cells.

Such vaccine for use in allergy can be either:

- an immunotolerance vaccine e.g. inducing T-cell tolerance against the immunogen by the regulatory T-cells and down-modulating the humoral immune response, employing a TLR9 ligand which is a TLR9 agonist of group 1 or is a TLR9 antagonist. In this case the vaccine would predominantly down-regulate Th1/2/17 responses against the immunogen, but activate Treg cells;
  or
- an immunostimulating vaccine inducing Th1 responses against the immunogen while preventing humoral immune response against the vaccine, employing a TLR9 ligand which is a TLR9 agonist of group 3.

According to this embodiment of an immunotolerance vaccine, said anti-CD32 moiety is specifically targeting either CD32b or both, CD32a and CD32b, with a high affinity of Kd≤$10^{-6}$ M, preferably a higher affinity with a Kd≤$10^{-7}$ M, more preferred Kd≤$10^{-8}$ M. It is preferred that the anti-CD32 moiety is specifically targeting both CD32a and CD32b.

Also for the immunostimulating vaccine for use in allergy, said anti-CD32 moiety is specifically targeting CD32a and CD32b, with a high affinity of Kd≤$10^{-6}$ M, preferably with a higher affinity, e.g. a Kd≤$10^{-7}$ M, more preferred Kd≤$10^{-8}$ M. It is preferred that the anti-CD32 moiety is specifically targeting both CD32a and CD32b.

Specifically, there is provided a vaccine according to the invention, wherein said immunogen is derived from an allergen, for use in the immunotherapy of allergy diseases and wherein said anti-CD32 moiety is targeting CD32a and CD32b.

Specific embodiments of the invention may be depicted from the following table, indicating the selection of the anti-CD32 moiety according to its specificity and affinity of binding CD32a and/or CD32b, the type of TLR9 ligand and the type of immunogen.

TABLE 1

| Specific embodiments: | | | | | | | | |
|---|---|---|---|---|---|---|---|---|
| Indication | CD32a >> CD32b | CD32b = CD32a | TLR9 agonist Group 1 | TLR9 agonist Group 2 | TLR9 agonist Group 3 | TLR9 antagonist | Immunogen | Vaccine type |
| Autoimmune disease | | X | X | | | | autoantigen | Immuno tolerance |
| Autoimmune disease | | X | | X | | | autoantigen | Immuno tolerance |
| Autoimmune disease | | X | | | | X | autoantigen | Immuno tolerance |
| Allergy | | X | | | | X | Allergen | Immuno tolerance |
| Allergy | | X | | | X | | Allergen | Immuno stimulating |
| Allergy | X | | | | X | | Allergen | Immuno stimulating |
| Oncology | X | | | | X | | Tumor Ass. Anti | Immuno stimulating |
| Infectious diseases | X | | | | X | | Pathogen | Immuno stimulating |

Columns 2 and 3 refer to the selectivity and/or affinity of anti-CD32 moiety binding to either of CD32a and CD32b:

CD32a>>CD32b meaning a selective binding to CD32a (difference in binding affinity/Kd of at least 1 log);

CD32b=CD32a meaning binding to both CD32a and CD32b to about the same extent (difference in binding affinity/Kd of less than 1 log).

Particularly when providing an anti-allergy vaccine, i.e. an immunotolerance vaccine for the treatment of allergic disease conditions, or an anti-autoimmune disease vaccine, i.e. an immunotolerance vaccine for the treatment of autoimmune disease conditions, the anti-CD32 moiety is specifically targeting both CD32a and CD32b with about equally high affinity, e.g. a differential affinity of binding to each of the CD32a and CD32b targets of less than 2 logs, preferably less than 1 log difference in the Kd values.

According to the invention there is further provided an immunogenic composition comprising a. a directed adjuvant comprising at least an anti-CD32 moiety linked to a TLR9 ligand and a first peptidic alpha-helix; and b. a gastrin-17 peptide immunogen linked to a second peptidic alpha-helix coiled to the first alpha-helix, which peptide immunogen is any of (i) human gastrin-17 comprising the amino acid sequence of SEQ ID 78, or a fragment thereof comprising the amino acid sequence of SEQ ID 79, or at least the 4 N-terminal amino acids of SEQ ID 79;

(ii) an analog of (i), preferably of rhesus monkey or murine origin; and/or (iii) a functionally active variant of any of (i) or (ii), with one, two, three or four point mutations in the amino acid sequence of SEQ ID 79.

Specifically, said peptide immunogen is a linear peptide comprising or consisting of (i) an amino acid sequence of SEQ ID 80, preferably SEQ ID 81;

(ii) an amino acid sequence of SEQ ID 82, preferably SEQ ID 83;

(iii) an amino acid sequence of SEQ ID 84, preferably SEQ ID 85; or (iii) an amino acid sequence of SEQ ID 79 or 86.

It is preferred that the immunogenic composition of the invention comprises at least two of the peptide immunogens linked to the second peptidic alpha-helix, preferably 2, 3 or 4 of the peptide immunogens.

When more than one peptide immunogens are bound to the second alpha-helix, the peptide immunogens may e.g. be conjugated to the alpha-helix consecutively, i.e. linking the peptide immunogens in a row, e.g. linking the C-terminus of a first peptide immunogen to an N-terminus of a second peptide immunogen, which first and second peptide immunogens are identical or differ from each other.

Alternatively, or in addition, further peptide immunogens may be incorporated into the immunogenic composition of the invention by cross-linking e.g. two or more peptide immunogens, which are either identical or differ from each other, are linked to the same alpha-helix by chemical reaction, such as chemical cross-linking permitting the establishment of inter-molecular cross-linkages, e.g. with homo-bifunctional reagents such as Dimethyl adipimidate (DMA), Dimethyl suberimidate (DMS), or glutaraldehyde. For example, such cross-linking may be performed employing glutaraldehyde crosslinking by free lysine groups of the alpha-helix or a spacer/linker, respectively. Thereby, two or more peptide immunogens as used according to the invention are coupled to the alpha-helix in parallel, or side-by-side.

According to a further specific aspect of the invention, the immunogenic composition comprises one or more linker sequences, preferably composed of glycine and/or serine and/or lysine residues, preferably an amino acid sequence of SEQ ID 89 or 90. The linker sequences may be linear or branched, e.g. to provide linkage or cross-linkage between two or more peptide or polypeptide entities.

According to a further specific aspect of the invention, the immunogenic composition comprises or consists of the amino acid sequence of SEQ ID 87 or SEQ ID 88.

According to the invention, there is further provided a vaccine comprising the immunogenic composition of the invention, and a pharmaceutically acceptable carrier. Such vaccine is typically an immunostimulating vaccine, e.g. stimulating the humoral and T-cell (Th1) immune response.

According to a preferred embodiment, the humoral and T-cell (Th1) immune response is transient, e.g. with a specific maximum IgG titer induced upon vaccination that is typically achieved within a period of 2 to 8 weeks upon vaccination, followed by a titer reduction by at least 30%, preferably at least 40%, or at least 50%, or at least 60%, or at least 70%, or at least 80%, or at least 90%, or up to 100%, within 6 months upon vaccination, preferably within 5 months, or within 4 months, or within 3 months, or within 2 months. Such reduced titer may be again increased upon a booster injection. In a series of vaccination, the transient immune response is possibly determined upon the last injection of the immunogenic composition or vaccine. The transient immune response has the advantage of a controlled treatment with, e.g. the possibility to interrupt or stop treatment as necessary.

The invention particularly provides for a vaccine comprising an immunogenic composition comprising a directed adjuvant comprising at least an anti-CD32 moiety linked to a TLR9 ligand, and an immunogen, which is bound to the directed adjuvant, preferably by linkage or affinity binding; e.g. fusion by recombinant DNA technologies or chemically conjugated.

for use in treating a subject for eliciting an IgG immune response directed to the immunogen which is transient, preferably with a specific maximum IgG titer induced upon vaccination that is typically achieved within a period of 2 to 8 weeks upon vaccination, followed by a titer reduction by at least 30%, preferably at least 40%, or at least 50%, or at least 60%, or at least 70%, or at least 80%, or at least 90%, or up to 100%, within 6 months upon vaccination, e.g. upon the last vaccination in a series of vaccinations.

Such vaccine is preferably used with an immunogen that is or comprises an antigen or epitope of a self-antigen, e.g. selected from the group consisting of a tumor associated antigen (TAA), preferably a tumor cell surface receptor or a soluble antigen produced by the tumor cell, such as Her2/neu, gastrin, interferon alpha (INFα), epidermal growth factor (EGF), EGF receptor (EGF-R), epithelial cell adhesion molecule (EpCAM), alphafetoprotein (AFP), carcinoembryonic antigen (CEA), MUC-1 or LewisY, prehormones and hormones, such as any of the digestive hormones, including secretin or insulin, thyroid hormones, or sexual hormones.

The self-antigen is particular of human origin when treating a human subject.

By the transient Th1 immune response induced with this type of vaccine, there is no irreversible autoimmune response, but a reversible one, which is indicated by the level of specific circulating IgG, e.g. that is less than, 50%, preferably less than 60%, preferably less than 70%, preferably less than 80%, or less than 90%, even up to 100% reduction of circulating IgG, after the IgG has been induced. The IgG induction is, typically, followed by the IgG reduction within a specific time period e.g within 1 year after last immunization, or within 6 months, or within 3 months.

In this regard, the invention further provides for a method of treating a subject in need of a transient reduction of self-antigens or autoantigens by administering an effective amount of the vaccine to the subject, e.g. in one or more doses, wherein at least the last dose provides for the transient effect.

According to the invention, there is further provided a kit for preparing the immunogenic composition of the invention, comprising the following components a. a directed adjuvant comprising at least an anti-CD32 moiety linked to a TLR9 ligand and a first peptidic alpha-helix; and b. a gastrin-17 peptide immunogen linked to a second peptidic alpha-helix matching the first alpha-helix, which peptide immunogen is any of (i) human gastrin-17 comprising the amino acid sequence of SEQ ID 78, or a fragment thereof comprising the amino acid sequence of SEQ ID 79, or at least the 4 N-terminal amino acids of SEQ ID 79;

(ii) an analog of (i), preferably of rhesus monkey or murine origin; and/or (iii) a functionally active variant of any of (i) or (ii), with one, two, three or four point mutations in the amino acid sequence of SEQ ID 79.

The kit may specifically be used to facilitate the production of the vaccine by using the preformed directed adjuvant component for the combination with an immunogen that may be provided according to the need of a subject group or the individual subject.

According to the invention, there is further provided the immunogenic composition for use in treating a subject suffering from gastrin dependent diseases or disease conditions. Such disease or disease condition is primarily caused by or associated with the endogenous gastrin production or over-production in the subject. The gastrin dependent diseases or disease conditions specifically include gastrin dependent tumors or gastrin dependent cancer, such as pancreatic cancer, or gastrointestinal cancers, gastric ulcer, gastroesophageal reflux disease (GERD), end-stage renal failure (ESRF), or obesity.

Thus, the invention specifically provides for a method of treating a subject suffering from gastrin dependent diseases, such as gastrin dependent tumors or gastrin dependent cancer, such as pancreatic cancer, or gastrointestinal cancers, gastric ulcer, gastroesophageal reflux disease (GERD), end-stage renal failure (ESRF), or obesity, by administering to the subject an effective amount of the immunogenic composition or the vaccine of the invention, either prophylactically, e.g. to prevent the outbreak of a disease or disease condition or the progress of disease, or therapeutically, e.g. to ameliorate a disease or disease condition.

Specifically, the composition is administered to the subject in an effective amount employing a prime-boost strategy.

Specifically, the effective amount is ranging between 0.0001 and 2 mg per administration, preferably between 0.001 and 2 mg per dose.

According to a specific embodiment of the invention, the subject is further treated by chemotherapy, e.g. in the course of treating a gastrin dependent cancer.

Specifically, the immunogenic composition of the invention triggers a protective immune response in the subject, preferably with a serum IgG titer against human gastrin-17 of at least $1/1000$, preferably at least $1/10^4$, preferably at least $1/10^5$, preferably at least $1/10^6$, or lower, thus, detectable at a higher dilution.

FIGURES

FIG. 1 shows the high affinity interaction of the coiled coil used in the invention (Example 4).

The immunogen with coil-K is coated to a BIACore Chip and the warhead with coil-E is in the flow-buffer. Each coil comprises of a 5 time heptad repeat alpha helix Data confirm extreme affinity of the two coils for each other (visualized by low off-rate)[32].

Figure 2:
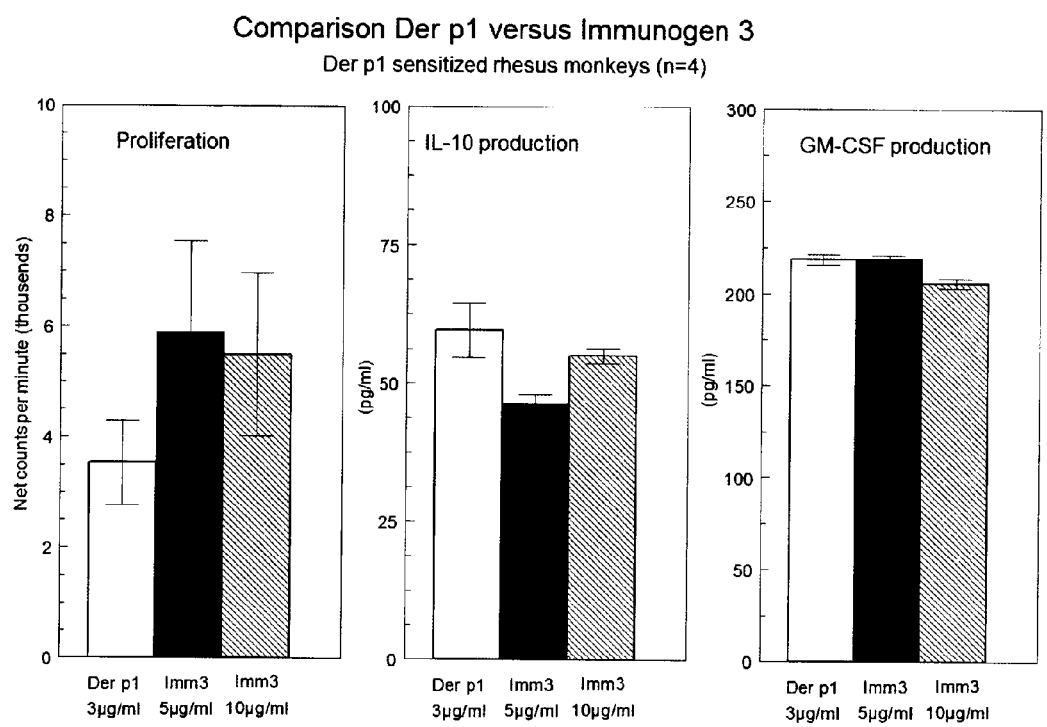

Binding of immunogen coil to warhead coil is specific and can be blocked by pre-incubation with immunogen FIG. 2 shows Immunogen 3 induced T cell reactivity (Example 6).

Figure 3:
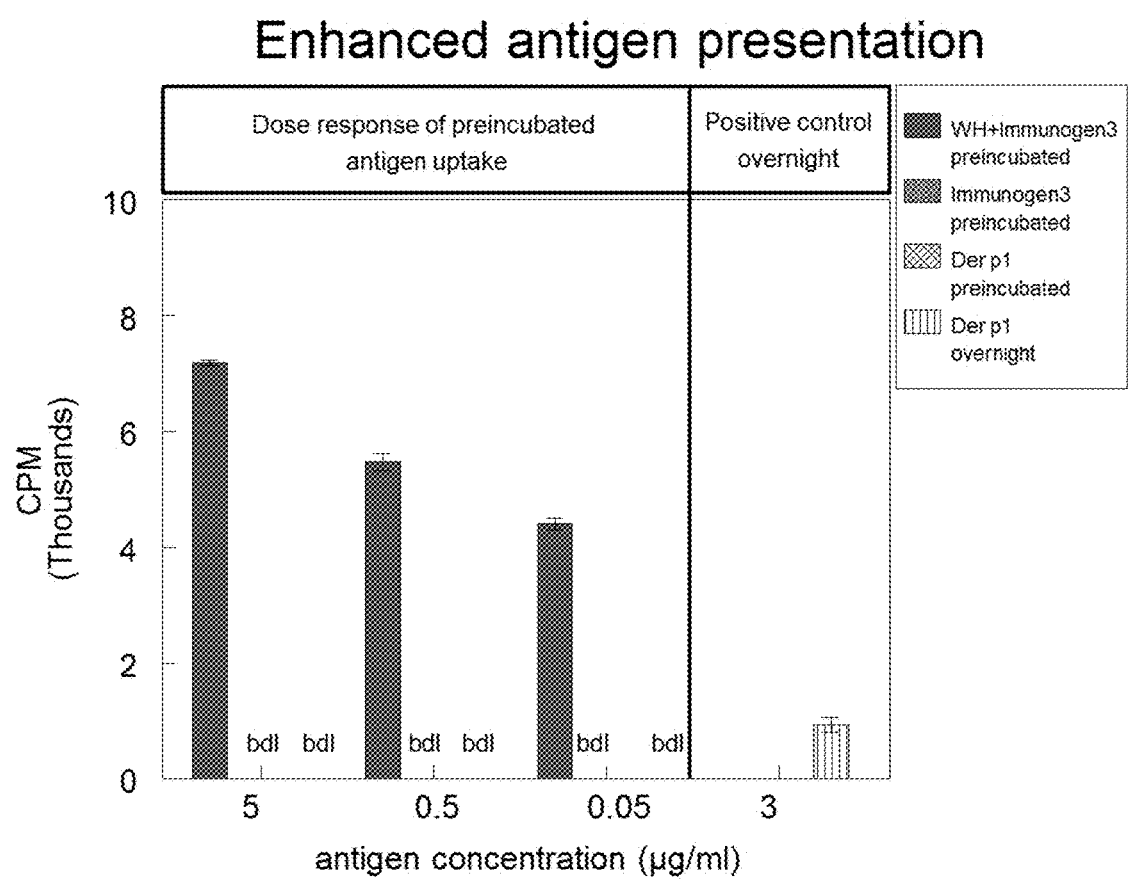

PBMCs from Der p1 sensitized rhesus monkeys (macaca mulatta) were cultured in triplicate with Der p1 or immunogen 3. Proliferation was assayed by the incorporation of [$^3$H]-thymidine. Results are shown as counts per minute. In addition supernatants were assayed for IL-10 and GM-CSF levels each indicated as pg/ml There is no significant difference between the response to Der p1 or immunogen 3, neither in proliferation nor in cytokine production, indicating that the T cell epitopes in immunogen 3, which were selected on the basis of human HLA Class II expression, are equally well presented by rhesus monkey class II molecules and induce equally strong T cells responses FIG. 3 shows: Warhead mediated enhanced antigen presentation (Example 7)

24 h proliferation (assayed by the incorporation of [$^3$H]-thymidine) of Rhesus monkey (macaca mulatta) T cells after pre incubation for 30 'on ice with respectively warhead and Der p1 or warhead and immunogen 3. After each pre-incubation the cells were washed. (bdl=below detection limit).

Only when the immunogen could interact with the warhead through its coil (immunogen3) T cell proliferation in a dose dependent fashion could be seen. Der p1 did not show a response when pre-incubated with warhead. As positive control Der p1 is shown to be reactive after overnight incubation (without washing).

Figure 4:
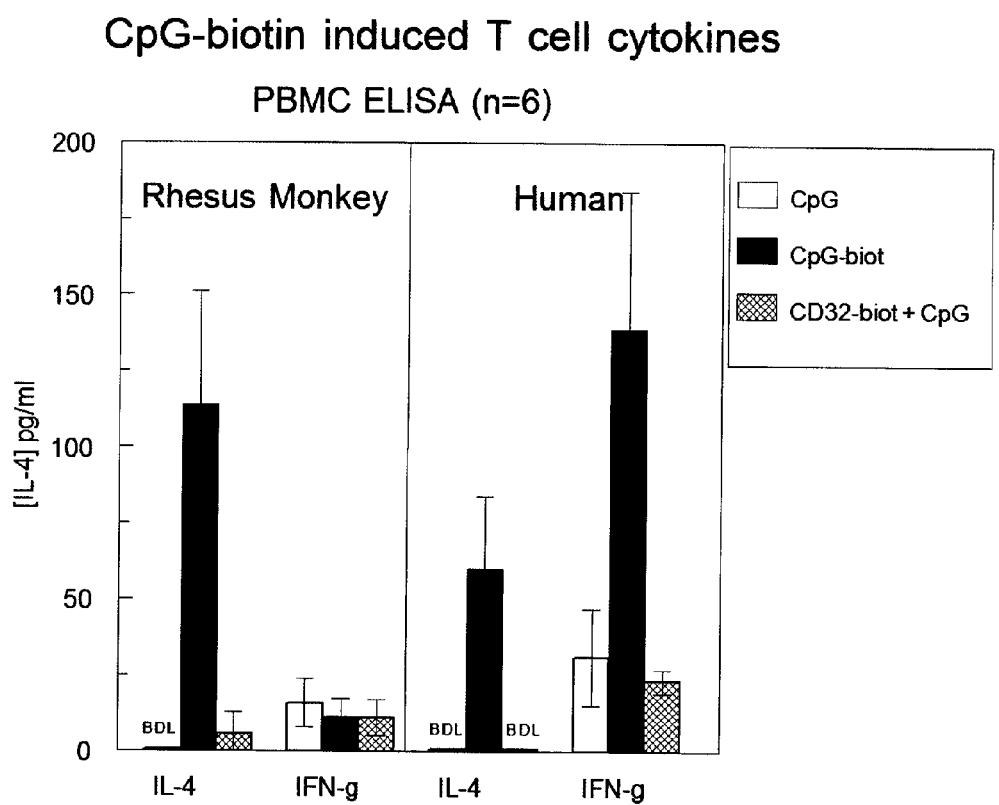

Warhead mediated antigen uptake is more efficient than uptake through pinocytosis FIG. 4 shows autoimmune response induced by an autoantigen coupled to CpG (Example 8)

PBMCs rhesus monkeys (macaca mulatta) and normal human PBMCs were cultured were cultured for 24 h with CpG or CpG-biot or aCD32-biot+CpG. Supernatants were harvested and assayed for IL-4 and IFNg s (each indicated as pg/ml)

Figure 5:
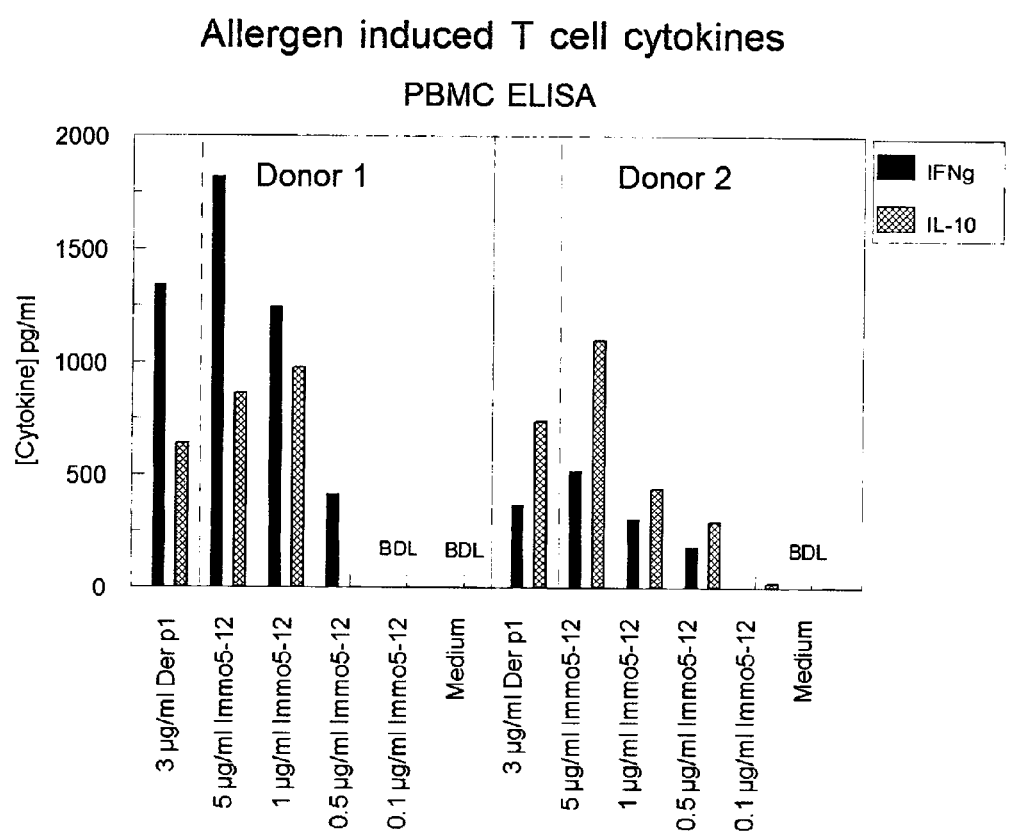

In the case where CpG was coupled to biot (CpG-biot) a strong IL-4 (rhesus monkey and human PBMC) was induced compared to CpG without biot. Human PBMC also showed a strong IFNg response against CpG-biot. When biot and CpG were not coupled (aCD32-biot+ CpG) no increased response was seen compared to CpG in humans or rhesus monkey PBMCs FIG. 5 shows Immunogen 5 induced T cell reactivity (Example 10)

PBMCs of healthy human donors were cultured for 24 h in triplicate with Der p1 or immunogen 5. Supernatants were harvested and assayed for IL-10 and GM-CSF levels (each indicated as pg/ml; BDL=below detection limit)

Human T cells respond equally well to immunogen 5 as to Der p1, as measured by IL-10 and IFNg induction.

Figure 6:
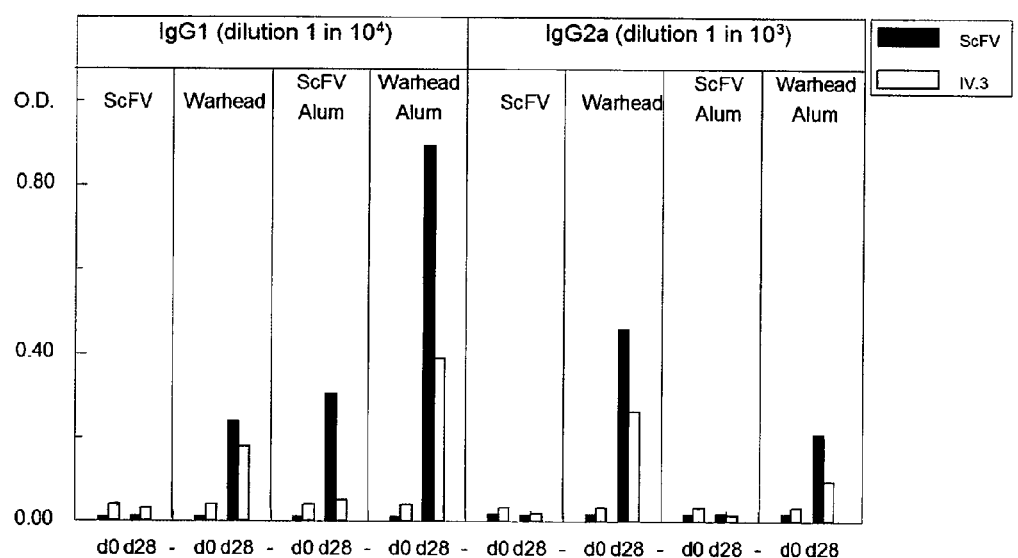

FIG. 6 shows induction of autoimmune response by the warhead SG100 Immunization with warhead induced a strong IgG1 and IgG2a response to ScFV-1-coil as well as to mAb IV.3 on day 28. A positive response was seen independent of the presence of Alum. Immunization with ScFV-1-coil only induced an IgG1 response against ScFV-1-coil and only in the presence of Alum, no IgG2a response was induced.

Figure 7:
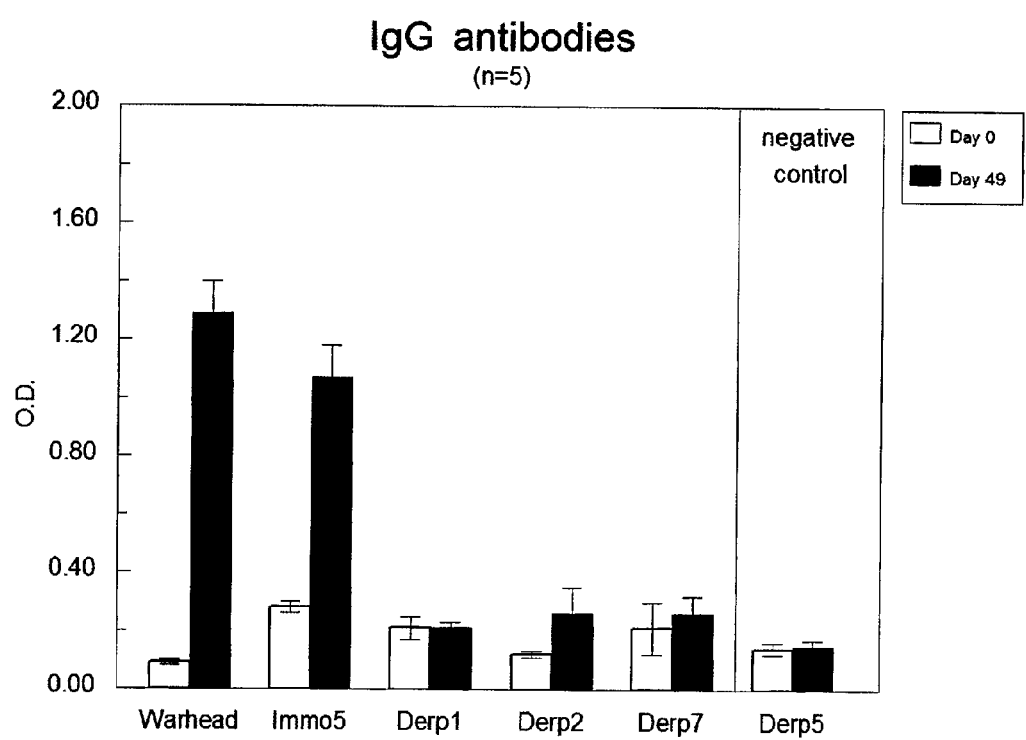

FIG. 7 (example 12.8)

Strong IgG responses were measured against the warhead and the immunogen of SG100, but no antibodies were detected against Der p1, Der p2, Der p5 or Der p7, indicating that the animals were naive for the tested HDM allergens and that SG100 does not contain B cell epitopes, which cross-react with the tested HDM allergens.

Figure 8:
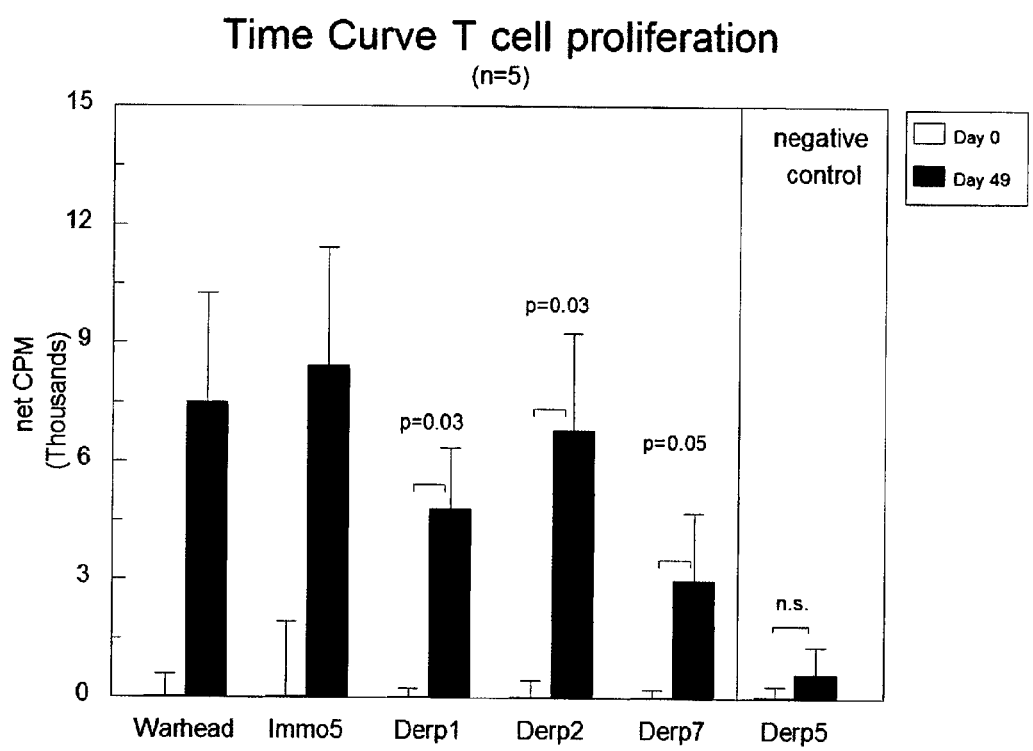

FIG. 8 (example 12.8)

Animals showed strong proliferation when stimulated in vitro with warhead, immo5, Der p1, Der p2, Der p7, but not against Der p5. Der p5 is not part of the immo5.

Figure 9:
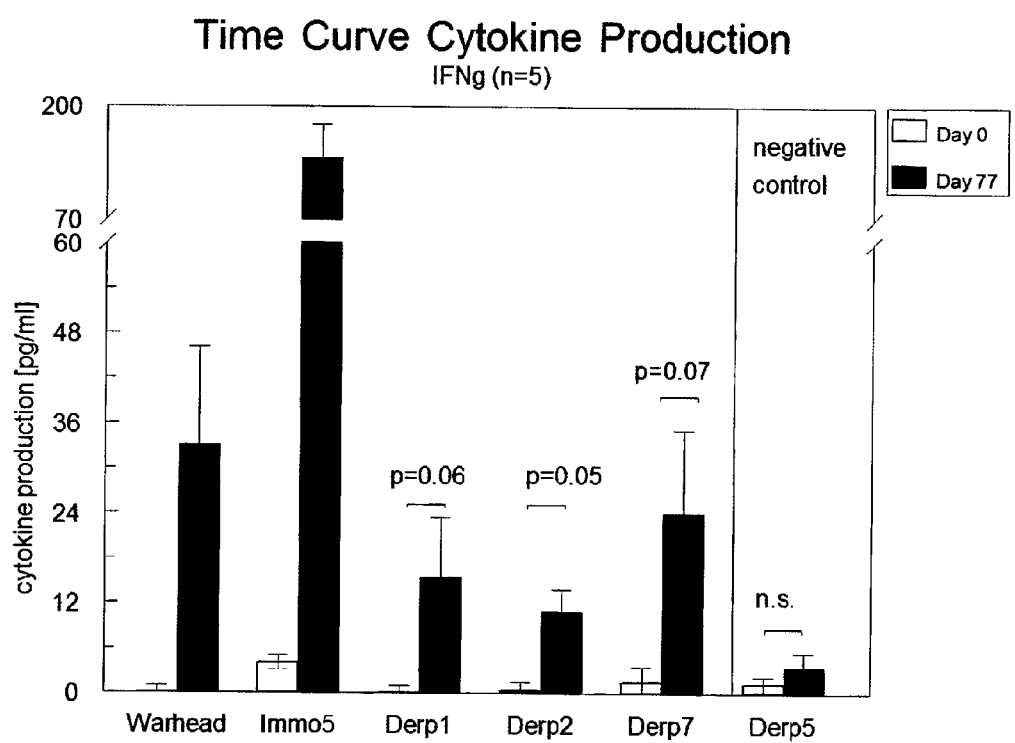

FIG. 9 (example 12.8)

Animals produced IFNγ but no IL-4 after stimulation with warhead, immo5, Der p1, Der p2, Der p7 but not with Der p5. Der p5 is not part of the immo5

Figure 10:
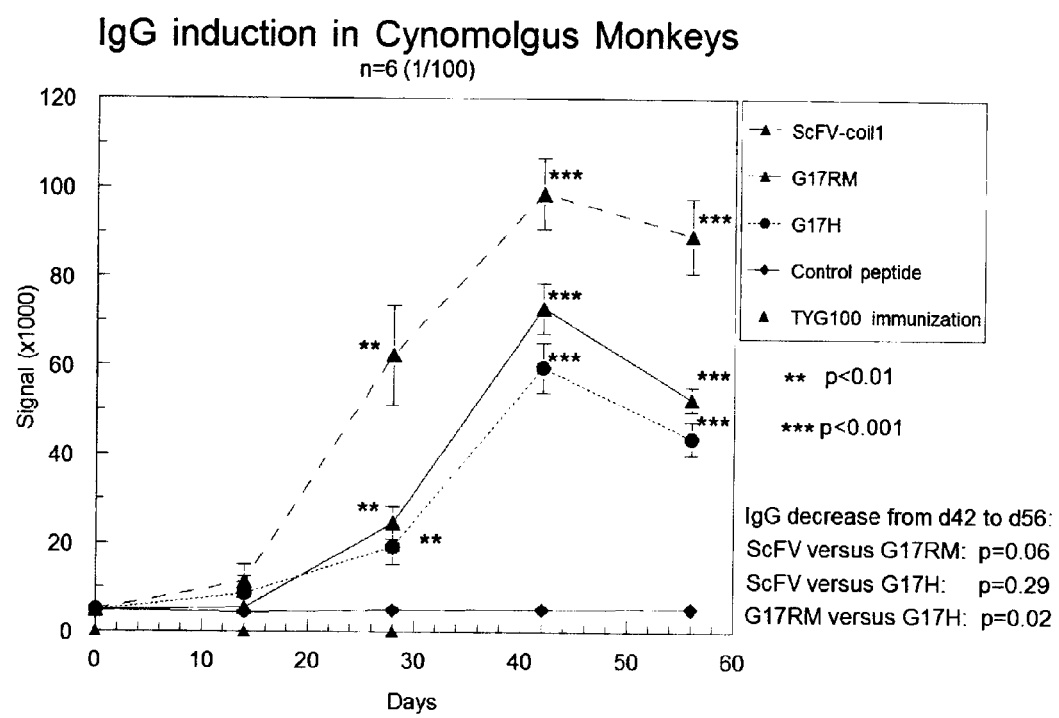

FIG. 10 shows the antibody (IgG induction) in cynomolgus monkeys. Time curve IgG anti G17 induction, after three injections with the vaccine (TYG100_2RM) on d0, d14 and d28.

Figure 11:
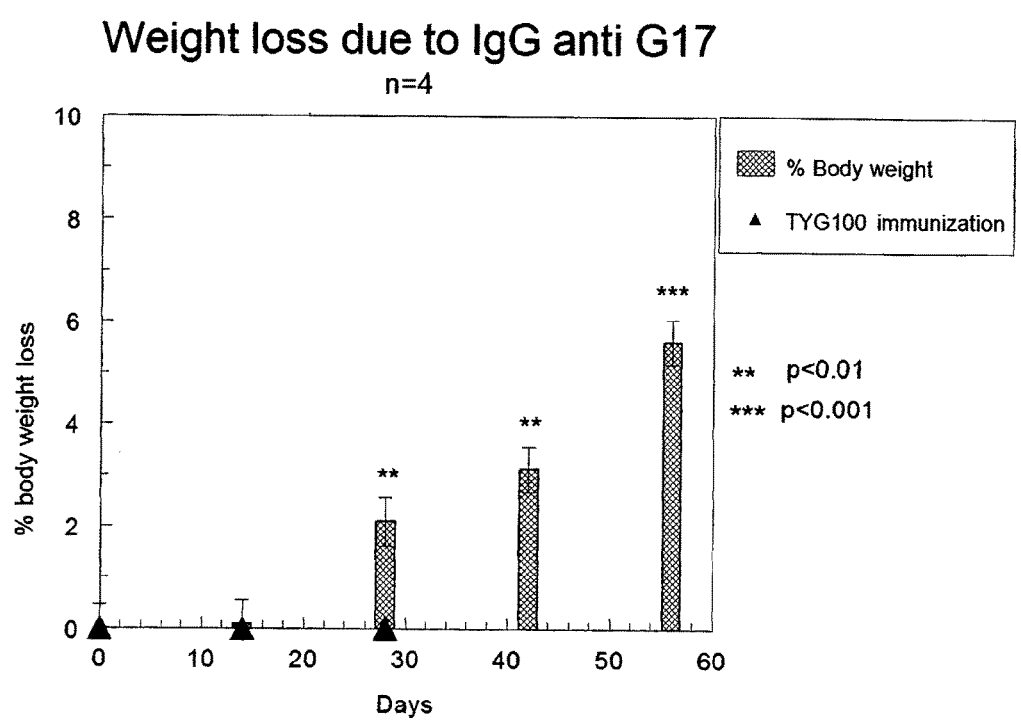

A significant IgG induction was seen against the ScFV-coil1 and G17RM and G17H. No response was seen against a control peptide of similar molecular weight or when the animals were immunized with G17RM_2 without the presence of warhead. All specific IgG titers decline 4 weeks after last immunization indicating that booster injections are necessary to maintain the IgG levels. In addition, the presence of natural G17RM does not boost the response and since the decrease in IgG against G17RM is significantly higher than the one for ScFV-coil1, it may be concluded that the induced immune response is reversible FIG. 11 shows the weight loss upon anti-gastrin immunization.

Four out of 6 animals showed a significant time dependent weight loss after immunization with TYG100_2RM. It was observed by the animal care takers that these animals lost appetite for their afternoon snacks, without losing interest in normal daily food. Such observations were never made with other vaccines, therefore the anti-gastrin vaccine of the invention can be used to control obesity.

FIG. 12 shows the sequence information of

SEQ ID 78: human little gastrin, G17;

SEQ ID 79: human gastrin peptide, first (N-terminal) 12 AA (amino acids) of little gastrin, G12;

SEQ ID 80: N-terminal epitope of little gastrin, first (N-terminal) 4 AA, including specific functionally active variants with point mutations;

SEQ ID 81: N-terminal epitope of little gastrin, first (N-terminal) 4 AA, including more specific functionally active variants with point mutations;

SEQ ID 82: N-terminal epitope of little gastrin, first (N-terminal) 12 AA, including specific functionally active variants with point mutations;

SEQ ID 83: N-terminal epitope of little gastrin, first (N-terminal) 12 AA, including more specific functionally active variants with point mutations;

SEQ ID 84: N-terminal epitope of little gastrin, first (N-terminal) 13 AA, including specific functionally active variants with point mutations;

SEQ ID 85: N-terminal epitope of little gastrin, first (N-terminal) 13 AA, including more specific functionally active variants with point mutations;

SEQ ID 86: human gastrin peptide, first (N-terminal) 13 AA (amino acids) of little gastrin, G13;

SEQ ID 87: Immunogen component of TYG100_1H: Part of an immunogenic composition of the invention, comprising one human gastrin peptide of SEQ ID 86, a linker sequence and a peptide alpha-helix (TYG100_1H). This part may be linked to the suitable directed adjuvant by a coiled-coil linkage.

bold is the peptide immunogen, italic is linker, underlined is coil

SEQ ID 88: Immunogen component of TYG100_2H: Part of an immunogenic composition of the invention, comprising two human gastrin peptides of SEQ ID 86, a branched linker sequence and a peptide alpha-helix (TYG100_2H). This part may be linked to the suitable directed adjuvant by a coiled-coil linkage.

bold is the peptide immunogen, italic is linker, underlined is coil

SEQ ID 89: linear linker sequence;

SEQ ID 90: branched linker sequence.

DETAILED DESCRIPTION OF THE INVENTION

Specific terms as used throughout the specification have the following meaning.

The term "adjuvant" as used herein shall mean an integrated or co-administered component of a vaccine, which:
enhances the immune response to a specific immunogen, e.g. an antigen or a hapten. The immune response is typically greater than the immune response elicited by an equivalent amount of the immunogenic composition administered without the adjuvant,
and/or
the adjuvant is used to direct a particular type or class of immune response against the immunogen, e.g. a Th1 or Treg type of immune response, herein understood as "directed adjuvant".

An "effective amount" of an adjuvant of the present invention specifically is an amount which enhances an immunological response to the immunogen such that, for example, lower or fewer doses of the immunogenic composition are required to generate an efficient immune response of the intended class.

The directed adjuvant according to the invention not only mediates the efficient immune response, but also the regulation of the immune response in the desired way. By directing the immunogen to the appropriate immune cells for its internalization and further processing, the Th1 immune response is induced rather than the Th2 immune response, in particular when employing a TLR9 ligand that is a TLR9 agonist of group 3. If a TLR9 antagonist is used in the vaccine composition, the respective immune response is down-modulated in any case. If a TLR9 agonist of group 1 is combined with an anti-CD32 moiety that binds CD32b, the induction of Treg cells is usually anticipated.

An "effective amount" of an adjuvant of the present invention specifically is an amount which enhances an immunological response to the immunogen such that, for example, lower or fewer doses of the immunogenic composition are required to generate an efficient immune response of the intended class.

The directed adjuvant according to the invention not only mediates the efficient immune response, but also the regulation of the immune response in the desired way. By directing the immunogen to the appropriate immune cells for its internalization and further processing, the Th1 immune response is induced rather than the Th2 immune response, in particular when employing a TLR9 ligand that is a TLR9 agonist of group 3. If a TLR9 agonist of group 1 is combined with an anti-CD32 moiety that binds CD32b, the induction of Treg cells is usually anticipated.

An "effective amount" of an immunogenic composition, e.g. as used in a vaccine of the invention refers to an amount sufficient to show a meaningful benefit in a subject being treated, when administered as part of a vaccination dosing regimen. Those of ordinary skill in the art will appreciate that, in some embodiments, a particular composition may be considered to contain a prophylactically or therapeutically effective amount if it contains an amount appropriate for a unit dosage form administered in a specific dosing regimen, even though such amount may be insufficient to achieve the meaningful benefit if administered as a single unit dose. Those of ordinary skill will further appreciate that an effective amount of an immunogenic composition may differ for different subjects receiving the composition, for example depending on such factors as the desired biological endpoint, the nature of the composition, the route of administration, the health, size and/or age of the subject being treated, etc. In some embodiments, an effective amount is one that has been correlated with beneficial effect when administered as part of a particular dosing regimen, e.g. a single administration or a series of administrations such as in a "boosting" regimen.

The term "peptidic alpha-helix" as used herein shall mean a coiled structural motif based on a peptide sequence comprising a number of repeats, also called coil repeats. Such alpha-helix is capable of binding to another counterpart, also called matching alpha-helix of the same type to form a dimer, trimer or further oligomer, also called coiled coil.

A coiled coil is a structural motif in polypeptides or peptides, in which two to seven alpha-helices are coiled together like the strands of a rope. In some embodiments, the coiled coil of the vaccine is one with two alpha-helices coiled together. Such alpha helical regions are likely to form coiled-coil structures and may be involved in oligomerization of the coil repeats as measured in a suitable coiled coil interaction binding assay.

Specifically, a dimer of alpha-helices can be formed by contacting the two monomers, such that the dimer is formed through an interaction with the two alpha helix coiled coil domains. In some embodiments the coils comprise a peptide with the amino acid sequence as set forth in SEQ ID NO: 1 or 2 (coil and anti-coil), which include x repeats.

```
                                            (SEQ ID 97)
EVSAL

E5:
                                            (SEQ ID 1)
EVSALEKEVSALEKEVSALEKEVSALEKEVSALEK-NH2

(SEQ ID 98)
KVSAL

K5:
                                            (SEQ ID 2)
KVSALKEKVSALKEKVSALKEKVSALKEKVSALKE-NH2
```

Alternatively, any of the sequences described by Chao et al[33] or Litowsky et al[34] or functional equivalents, which generate the specific coiled-coil type linkage, may be used:

| Coil Type | Type/number of repeats: Exemplary sequence |
|---|---|
| EIAAL SEQ ID 91 | E3: EIAALEKEIAALEKEIAALEK-NH2 (SEQ ID 3) |
| EIAAL SEQ ID 91 | E4: EIAALEKEIAALEKEIAALEKEIAALEK-NH2 (SEQ ID 4) |
| KIAAL SEQ ID 92 | K3: KIAALKEKIAALKEKIAALKE-NH2 (SEQ ID 5) |
| KIAAL SEQ ID 92 | K4: KIAALKEKIAALKEKIAALKEKIAALKE-NH2 (SEQ ID 6) |
| EISAL SEQ ID 93 | E3: EISALEKEISALEKEISALEK-NH2 (SEQ ID 7) |
| EISAL SEQ ID 93 | E4: EISALEKEISALEKEISALEKEISALEK-NH2 (SEQ ID 8) |
| KISAL SEQ ID 94 | K3: KISALKEKISALKEKISALKE-NH2 (SEQ ID 9) |
| KISAL SEQ ID 94 | K4: KISALKEKISALKEKISALKEKISALKE-NH2 (SEQ ID 10) |
| EVAAL SEQ ID 95 | E3: EVAALEKEVAALEKEVAALEK-NH2 (SEQ ID 11) |
| EVAAL SEQ ID 95 | E4: EVAALEKEVAALEKEVAALEKEVAALEK-NH2 (SEQ ID 12) |
| KVAAL SEQ ID 96 | K3: KVAALKEKVAALKEKVAALKE-NH2 (SEQ ID 13) |
| KVAAL SEQ ID 96 | K4: KVAALKEKVAALKEKVAALKEKVAALKE-NH2 (SEQ ID 14) |
| EVSAL SEQ ID 97 | E3: EVSALEKEVSALEKEVSALEK-NH2 (SEQ ID 15) |
| EVSAL SEQ ID 97 | E4: EVSALEKEVSALEKEVSALEKEVSALEK-NH2 (SEQ ID 16) |
| KVSAL SEQ ID 98 | K3: KVSALKEKVSALKEKVSALKE-NH2 (SEQ ID 17) |
| KVSAL SEQ ID 98 | K4: KVSALKEKVSALKEKVSALKEKVSALKE-NH2 (SEQ ID 18) |

For the purpose of the invention the preferred type of a coiled coil is a dimer, either a heterodimer (heterocoil) of two different, but matching helices, which differ in at least one amino acid in the coil repeat sequence, or else a homodimer of two identical matching helices, i.e. those comprising the matching coil repeat sequences (the "coils").

The preferred number of coil repeats is 3-5, preferably any of the combinations 3+3, 3+4, 3+5, 4+4, 4+5, 5+5, 4+3, 5+3 or 5+4.

As an alternative to heptad repeats (repeats of an amino acid sequence consisting of 7 amino acids, 7-mers), 6-mers, 8-mers, or 9-mers may be used.

In case of a homodimeric coiled coil, the typical number of coil repeats is specifically not more than 5, so to avoid undesired mismatches of the structure. In case of a heterodimeric coiled coil, it is typically desirable to employ a length of the peptide sequence with at least 3 coils. Thereby the binding of the components of the vaccine, i.e. the directed adjuvant and the immunogen components, to each other is typically achieved with preferred high affinity of a Kd of less than $10^{-7}$ M, more preferred less than $10^{-5}$ M or $10^{-9}$ M. However, although more repeats increase the affinity, this may be at the cost of increased homodimerisation The components of the immunogenic composition of the invention may also comprise a peptide spacer so to link the anti-CD32 moiety and/or the TLR9 ligand, and optionally also the epitope (e.g. of the peptide immunogen) with the coil repeats, respectively. For example, the peptide spacer can be on either or both ends of a coiled coil. Each of the peptide spacers can be attached to a single alpha helix coiled coil domain of the coiled coil.

The peptide spacer can be, for example, a peptide of at least 5, 6, 7, 8, 9, 10, 15, 20, 25, 30, 35, 40, 45 or 50 amino acids or more, either linear or branched, e.g. to provide for two, three, four, or more branches. The number of amino acids in the peptide spacer may be, in some embodiments, 20 amino acids or up to 10 amino acids greater or fewer, depending on the particular sequences and length of the coil.

The term "anti-CD32 moiety" as used herein shall mean a ligand specifically binding to the cellular target CD32, either CD32a, CD32b or both, CD32a and CD32b. The moiety can be any binding structure, such as derived from proteins, polypeptides or peptides, including antibodies and antibody fragments or composite molecules with a binding part. The binding part of the molecules or molecule complex of the invention can be comprised of proteins such as antibodies or antibody fragments, such as Fab, Fv, VH/VL dimer, scFv, dAb, F(ab)2, minibody, small mutated immunoglobulin domains, Fcab, Mab$^2$ or other biological binders, such as soluble T-cell receptor, Darpins, etc. Antibodies and antibody fragments and derivatives may be generated and selected for binding to CD32 according to known methods such as hybridoma technology, B-cell cloning, phage display, yeast display, ribosome display or cell surface display of antibody libraries, array screening of variant antibodies. Exemplary anti-CD32 moieties are scFv derived from the anti-CD32 monoclonal antibody AT-10[35], IV.3[36], 2E6[37] or any other aCD32 monoclonal antibody The specific binding may be determined in a suitable binding assay, such as conventional immunoassays.

There are numerous methods known in the art for detecting binding in an immunoassay. Various immunoassays known in the art can be used including competitive and non-competitive assay systems using techniques such as radioimmunoassays, ELISA (enzyme linked immunosorbent assay), immunoradiometric assays, gel diffusion precipitation reactions, immunodiffusion assays, western blot, BIAcore etc.

The term "cross-reactive" with respect to antigens or antibodies as used herein shall refer to epitopes shared between antigens of different origin, e.g. from human, rhesus monkey or mouse origin. The N-terminal epitope consisting or comprising the first 4 AA of G17 was found to be cross-reactive in peptides of various origin, which epitope triggers an immune response and IgG antibodies that are cross-reactive with the epitopes.

The immunogenic composition of the invention is specifically useful to treat gastrin dependent diseases or disease conditions that are associated with excess gastrin, e.g. gastrin dependent tumors or gastrin dependent cancer, such as pancreatic cancer, gastric ulcer, gastroesophageal reflux disease (GERD), end-stage renal failure (ESRF), or obesity.

The term "gastrin dependent tumor" or "gastrin dependent cancer" as used herein shall refer to tumors or disease or disease conditions associated therewith, of e.g. gastrin-dependent colorectal adenocarcinoma and other gastrin-dependent cancers such as stomach, liver, pancreatic and small cell carcinoma of the lungs. The term is specifically used herein with regard to treating the tumor for preventing tumor disease progression, for a positive tumor response or for tumor shrinkage. The term is also applied to minimal residual disease, which would be successfully treated, e.g. targeting circulating tumor cells to reduce their number below a certain threshold, e.g. below the detection limit.

Gastric ulcer disease, may be caused by increased stomach acid and a breakdown of the complex stomach defenses that normally protect the gastric mucosa from acid damage. Although the two conditions have different etiologies, both benefit from a reduction in gastric acid secretion. Gastric acid is produced in a specialized stomach cell, the parietal cell. Parietal cells can be stimulated to secrete acid by acetylcholine, histamine and gastrin, upon the binding of each of these compounds with specific receptors on the surface of the cell. Of these the most potent stimulator of acid secretion is the peptide hormone gastrin. The anti-gastrin immunotherapy therapy as described herein, would ameliorate the gastric ulcer disease conditions.

The term "gastrin-17 peptide" or "G17 peptide" or "G17" as used herein shall refer to the little gastrin G17, which consists of the N-terminal 17 AA of gastrin. The G17 peptide may be of human origin, or other mammalian origin, including rhesus monkey, or mouse, thus, has a human or other mammalian sequence, or may be an artificial construct, such as to incorporate artificial sequences, e.g. obtained by changing the type and/or sequence of amino acid residues in the native (naturally occurring) G17 sequence. The term shall specifically include variants of human G17, with an amino acid sequence of SEQ ID 78, or fragments thereof, but differs from its peptide sequence, in that it is derived from a homologous sequence of a different species. These are referred to as naturally occurring variants or analogs. The term "analogs" shall also refer to chimeric constructs originating from two or more origins, wherein at least one part is naturally occurring, e.g. which constitutes the major part (at least 50%) of the peptide immunogen, and another part is different thereto, either naturally occurring or synthetic (artificial).

The term shall specifically include fragments or functionally active variants of G17, e.g. those comprising one or more point mutations, or else peptides or polypeptides comprising further amino acid sequences besides the G17, e.g. by extending the N-terminus and/or the C-terminus by additional one or more amino acid residues or sequences. An extension of the C-terminus is e.g. preferred with repeats of G17 sequences, either identical or not, or with further amino acid sequences of gastrin.

The term shall specifically include the peptides with one or more modified amino acid residues. Common modifications include phosphorylation, methylation, acetylation, amidation, formation of pyrrolidone carboxylic acid, isomerization, hydroxylation, sulfation, flavin-binding, cysteine oxidation and nitrosylation. The exemplary modification as described herein is the modification of the N-terminal glutamic acid of G17, i.e. the pyroGlu at position 1, which is also known as "Pyrrolidone carboxylic acid (Glu)" or pGlu or pE.

The term "functionally active variants" as used herein with respect to the peptide immunogen of the invention, shall mean a sequence resulting from modification of this sequence (a parent sequence), e.g. by insertion, deletion or substitution of one or more amino acids, such as by recombination techniques or chemical derivatization of one or more amino acid residues in the amino acid sequence, or nucleotides within the coding nucleotide sequence, or at either or both of the distal ends of the sequence, and which modification does not affect (in particular impair) the activity of this sequence. In the case of a peptide immunogen eliciting a certain immune response to target gastrin, the functionally active variant of the peptide immunogen would still incorporate the antigenic determinant or epitope, though this could be changed, e.g. to increase the immunogenicity. Specifically, the functionally active variants of the G17 peptide immunogen, or a fragment thereof, such as the G12 or G13 fragment, have the potency to elicit IgG anti-gastrin antibodies in a treated subject, which antibodies cross-react with the endogenous gastrin of the subject.

Functionally active variants may be obtained, e.g. by changing the sequence of a parent peptide, e.g. the human, rhesus monkey or murine G17 peptide, or a fragment thereof, e.g. the G12 or G13 peptide, by introducing one or more modifications that do not substantially impair the cross-reactive epitopes, to obtain a molecule with substantially the same immunogenicity. The term "substantially the same immunogenicity" as used herein refers to the amount of an immune response or anti-gastrin IgG antibodies induced in a subject treated with the immunogenic composition, which amount is preferably at least 20% at least 30% at least 40%, at least 50% at least 60%, at least 70%, at least 80%, at least 90%, at least 95%, at least 98% or even at least 100% or at least 110%, or at least 120%, or at least 130%, or at least 140%, or at least 150%, or at least 160%, or at least 170%, or at least 180%, or at least 190%, e.g. up to 200% of the amount as determined for the parent peptide.

In a preferred embodiment the functionally active variant of a parent peptide
a) is derived from the peptide by at least one amino acid substitution, insertion (addition) and/or deletion, e.g. comprising one or more point mutations wherein the functionally active variant has a specific sequence identity to the parent molecule, such as at least 50% sequence identity, preferably at least 60%, more preferably at least 70%, more preferably at least 80%, still more preferably at least 90%; and/or
b) consists of the peptide and additionally at least one amino acid heterologous to the peptide.

Functionally active variants may be obtained by sequence alterations in the peptide sequence, e.g. by one or more point mutations, wherein the sequence alterations substantially retains a function of the unaltered peptide sequence, when used in according to the invention. Such sequence alterations or point mutations can include, but are not limited to, (conservative) substitutions, additions, deletions, mutations and insertions, e.g. the alteration of 1, 2, 3, or 4 amino acids, or by addition or insertion of one to several amino acids, e.g. 1, 2, 3, or 4 amino acids, or by a chemical derivatization of one to several amino acids, e.g. 1, 2, 3, or 4, or combination thereof, preferably by point mutations that are not contiguous. The substitutions in amino acid residues may be conservative substitutions, for example, substituting one hydrophobic amino acid for an alternative hydrophobic amino acid.

Conservative substitutions are those that take place within a family of amino acids that are related in their side chains and chemical properties. Examples of such families are amino acids with basic side chains, with acidic side chains, with non-polar aliphatic side chains, with non-polar aromatic side chains, with uncharged polar side chains, with small side chains, with large side chains etc.

Preferred point mutations refer to the exchange of amino acids of the same polarity and/or charge. In this regard, amino acids refer to twenty naturally occurring amino acids encoded by sixty-four triplet codons. These 20 amino acids can be split into those that have neutral charges, positive charges, and negative charges:

The "neutral" amino acids are shown below along with their respective three-letter and single-letter code and polarity:

Alanine: (Ala, A) nonpolar, neutral;
Asparagine: (Asn, N) polar, neutral;
Cysteine: (Cys, C) nonpolar, neutral;
Glutamine: (Gln, Q) polar, neutral;
Glycine: (Gly, G) nonpolar, neutral;
Isoleucine: (Ile, I) nonpolar, neutral;
Leucine: (Leu, L) nonpolar, neutral;
Methionine: (Met, M) nonpolar, neutral;
Phenylalanine: (Phe, F) nonpolar, neutral;
Praline: (Pro, P) nonpolar, neutral;
Serine: (Ser, S) polar, neutral;
Threonine: (Thr, T) polar, neutral;
Tryptophan: (Trp, W) nonpolar, neutral;
Tyrosine: (Tyr, Y) polar, neutral;
Valine: (Val, V) nonpolar, neutral; and
Histidine: (His, H) polar, positive (10%) neutral (90%).
The "positively" charged amino acids are:
Arginine: (Arg, R) polar, positive; and
Lysine: (Lys, K) polar, positive.
The "negatively" charged amino acids are:
Aspartic acid: (Asp, D) polar, negative; and
Glutamic acid: (Glu, E) polar, negative.

"Percent (%) amino acid sequence identity" with respect to the peptide sequences described herein is defined as the percentage of amino acid residues in a candidate sequence that are identical with the amino acid residues in the specific peptide sequence, after aligning the sequence and introducing gaps, if necessary, to achieve the maximum percent sequence identity, and not considering any conservative substitutions as part of the sequence identity. Those skilled in the art can determine appropriate parameters for measuring alignment, including any algorithms needed to achieve maximal alignment over the full length of the sequences being compared.

Functionally active variants may be obtained by any of the known mutagenesis methods, including point mutations at desired positions, e.g. obtained by randomisation techniques. In some cases positions are chosen randomly, e.g. with either any of the possible amino acids or a selection of preferred amino acids to randomise the peptide sequences. In this regard, the term "mutagenesis" refers to any art recognized technique for altering a polynucleotide or polypeptide sequence.

The term "immunogen" as used herein shall mean one or more antigens triggering an immune response in a subject. The term "antigen" as used herein shall in particular refer to any antigenic determinant, which can be possibly recognized by a binding site of an antibody or is able to bind to the peptide groove of HLA class I or class II molecules and as such may serve as stimulant for specific T cells. The target antigen is either recognized as a whole target molecule or as a fragment of such molecule, especially substructures, e.g. a polypeptide or carbohydrate structure of targets, generally referred to as "epitopes", e.g. B-cell epitopes, T-cell epitope), which are immunologically relevant, i.e. are also recognizable by natural or monoclonal antibodies. Herein the use of T cell epitopes is preferred, e.g. to provide for allergy vaccines.

The term "peptide immunogen" as used herein shall mean an antigen or immunogen of peptidic structure, in particular an immunogen that comprises or consists of a peptide of a specific amino acid sequence, which is either provided as a linear peptide or branched peptide, comprising naturally occurring amino acid residues or modified ones, e.g. a derivative obtained by modification or chemical derivatization, such as by phosphorylation, methylation, acetylation, amidation, formation of pyrrolidone carboxylic acid, isomerization, hydroxylation, sulfation, flavin-binding, cysteine oxidation and nitrosylation.

The peptide immunogen is specifically designed to trigger an immune response in a subject, and particularly includes one or more antigenic determinants, which can be possibly recognized by a binding site of an antibody or is able to bind to the peptide groove of HLA class I or class II molecules or other antigen presenting molecules such as CD1 and as such may serve as stimulant for specific T cells. The target antigen is either recognized as a whole target molecule or as a fragment of such molecule, especially substructures, e.g. a polypeptide or carbohydrate structure of targets, generally referred to as "epitopes", e.g. B-cell epitopes, T-cell epitope, which are immunologically relevant, i.e. are also recognizable by natural or monoclonal antibodies. Herein the use of B cell epitopes is preferred to provide for e.g. oncology vaccines.

The term "epitope" as used herein according to the present invention shall in particular refer to a molecular structure which may completely make up a specific binding partner or be part of a specific binding partner to a binding site of modular antibody of the present invention. The term epitope may also refer to haptens. Chemically, an epitope may either be composed of a carbohydrate, a peptide, a fatty acid, an organic, biochemical or inorganic substance or derivatives thereof and any combinations thereof. If an epitope is a polypeptide, it will usually include at least 3 amino acids, preferably at least 4, 5, 6, 7, 8, 9, 10, 11, 12 or 13 amino acids. There is no critical upper limit to the length of the peptide, which could comprise nearly the full length of a polypeptide sequence of a protein. Epitopes can be either linear or conformational epitopes. A linear epitope is comprised of a single segment of a primary sequence of a polypeptide or carbohydrate chain. Linear epitopes can be contiguous or overlapping. Conformational epitopes are comprised of amino acids or carbohydrates brought together by folding of the polypeptide to form a tertiary structure and the amino acids are not necessarily adjacent to one another in the linear sequence. Specifically, epitopes are at least part of diagnostically relevant molecules, i.e. the absence or presence of an epitope in a sample is qualitatively or quantitatively correlated to either a disease or to the health status of a patient or to a process status in manufacturing or to environmental and food status. Epitopes may also be at least part of therapeutically relevant molecules, i.e. molecules which can be targeted by the specific binding domain which changes the course of the disease.

One or more epitopes of the same antigen or different antigens may be used according to the present invention, which can include antigens of all the self-antigens, pathogens, allergens or auto-antigens for which the regulation of the immune response is desired, e.g. against which induction of a substantial Th1-type response or Treg response (depending on the type of vaccine) in the host is desired.

In cancer disease an immune response to a self-antigen is desirable. The term "self-antigen" as used herein means any antigen, specifically polypeptide or peptide produced by a normal, healthy subject that does not elicit an immune response as such. These self-antigens may be produced at aberrant or high levels in certain disease states, including cancer disease, so called tumour associated antigens (TAAs). Herein, the human gastrin or human G17 is understood as a self-antigen in human subjects, and specifically as a TAA in subjects suffering from a gastrin dependent tumor. Self-antigens which are associated with auto-immune disease are herein called auto-antigens.

It is understood that the self-antigens can be naturally occurring, recombinantly or synthetically produced. It is also understood that the self-antigens need not be identical to the naturally produced antigen, but rather can include variations thereto having certain sequence identities, similarities or homology.

The choice of the self-antigen for use in cancer therapy depends on the type and stage of the cancer disease, and in particular on the expression pattern of a cancer cell such as derived from a tumour or metastases. Specific examples of selected tumour associated antigens possibly used in a vaccine according to the invention are Epithelial cell adhesion molecule (EpCAM), Lewis Y, alphafetoprotein (AFP) and carcinoembryonic antigen (CEA), HER2/Neu, MUC-1, etc.

The choice of an auto-antigen for use in the therapy of auto-immune diseases depends on the type of the auto-immune disease. Specific examples of selected auto-immune disease associated antigens possibly used in a vaccine according to the invention are C1q, ADAMTS13, Desmogelin 3, keratin, gangliosides (e.g. GM1, GD1a, GQ1b), collagen type IV, IgM, cardiolipin, annexin A5, etc In some embodiments, the immunogen comprises one or more specific allergens. An "allergen" is an antigen which can initiate a state of hypersensitivity, or which can provoke an immediate hypersensitivity reaction in a subject already sensitized with the allergen. Allergens are commonly proteins or chemicals bound to proteins which have the property of being allergenic. However, allergens can also include organic or inorganic materials derived from a variety of synthetic or natural sources such as plant materials, metals, ingredients in cosmetics or detergents, latexes, or the like.

The choice of an allergen for use in the anti-allergy therapy depends on the type and severity of allergy. Specific examples of selected allergy associated antigens possibly used in a vaccine according to the invention are any allergen conventionally used as immunogen, specifically house dust mite allergens (e.g. Der p1, Der p2, Der p3/—Der p23, Der f1, Der f2, Derf3/—Der f23), cat dander, grass or tree pollen, cockroach allergens, etc.

The choice of an antigen specifically inducing immune response against a pathogen for use in the prophylaxis or therapy of infectious diseases depends on the type of the pathogen, e.g. a microbial or viral infectious agent. Specific examples of selected pathogen derived antigens possibly used in a vaccine according to the invention are hepatitis B, hepatitis C, Cholera, HIV, Pertussis, Influenza, Typhoid, etc.

The peptide immunogen or the immunogenic composition used in the vaccine according to the invention, is usually contained in a vaccine in an effective amount, which is herein specifically understood as "immunologically effective amount". By "immunologically effective amount", it is meant that the administration of that amount to a subject, either in a single dose or as part of a series of doses, is effective on the basis of the therapeutic or prophylactic objectives. This amount will vary depending upon the health and physical condition of the subject to be treated, age, the capacity of the subject's immune system to synthesize antibodies, the degree of immune response desired, the formulation of the vaccine, and other conditions.

The invention also provides a method for treating a subject or raising an immune response in a subject, comprising the step of administering an immunologically effective amount of the peptide immunogen, the immunogenic composition or the vaccine of the invention.

An effective amount or dosage may range from 0.0001 to 2 mg, e.g. between 0.001 and 2 mg, of the immunogenic composition administered to the subject in need thereof, e.g. an adult human subject. The effective dosage of the immunogenic composition is capable of eliciting an immune response in a patient of effective levels of antibody titer to bind and neutralize endogenous mature and precursor G17 for, e.g. 1-3 months after immunization. The effectiveness of the therapy may be assayed by the anti-gastrin antibody titers in samples of blood taken from the subject.

The term "TLR9 ligand" as used herein is understood in the following way.

Toll-like receptor 9 (TLR9) recognizes unmethylated bacterial CpG DNA and initiates a signalling cascade leading to the production of proinflammatory cytokines. There are numerous structures or sequences that have been shown to act as a ligand of TLR9, i.e. bind to this receptor and thereby either activate (stimulate, upregulate, TLR9 agonist) or de-activate (downregulate, TLR9 antagonist) TLR9. For instance, microbial DNA or synthetic DNA, e.g. synthetic CpG ODN may stimulate TLR9 with variations in the number and location of CpG dimers, as well as the precise base sequences flanking the CpG dimers. Synthetic CpG ODN differ from microbial DNA in that they have a partially or completely phosphorothioated backbone instead of the typical phosphodiester backbone and may or may not have a poly G tail at the 3' end, 5' end, or both.

The term "agonist" in conjunction with the TLR9 ligand as used herein shall specifically refer to the binding and activation of TLR9 in a cell-based assay.

The TLR9 ligand which is composed of a nucleotide sequence is typically coupled to the directed adjuvant component of the present immunogenic composition by chemical coupling e.g. using the commercially available KIT from Solulink. A peptidic TLR9 ligand may be coupled using standard peptide chemistry or may be integrated using recombinant DNA technology.

Exemplary TLR9 ligands are ODN 2216[38] (group 1), ODN 2006/ODN 2007[39] (group2) and CpG-M362[40] (group 3).

Further exemplary TLR9 ligands may be peptides that mimic the action of a CpG TLR9 agonist, e.g. identified by or obtained from a peptide library, which are selected for the affinity to bind the TLR9 and proven agonistic activity, or protein ligands, including specific antibodies.

Specific TLR9 ligands are immunostimulatory peptides, e.g. those that mimic any of the CpG classes, such as peptides selected from a suitable peptide library. Exemplary immunostimulatory peptides are selected from the group consisting of ESWDKFLSHYLP (SEQ ID 50), TDWSWFY (SEQ ID 51), YPVYWPW (SEQ ID 52), EWWFYWP (SEQ ID 53), WFPIEWW (SEQ ID 54), DQVDIGY (SEQ ID 55), THQVYIS (SEQ ID 56), WFPIEWWFYWP (SEQ ID 57), DSWQAFLTKFVL (SEQ ID 58), HDIQWFWQHWNS (SEQ ID 59), WSWWDHTFNYML (SEQ ID 60), TTQQTWNVRYPY (SEQ ID 61), DHTMPWTRNAKN (SEQ ID 62), SWDPYWPFPWFS (SEQ ID 63), AIYYVPSPMFTV (SEQ ID 64), ETTLLKMWLAQM (SEQ ID 65), YPWLDVAVVSLY (SEQ ID 66), VPGWHYLATLRA (SEQ ID 67) and FDPLGSRDIKGS (SEQ ID 68), and functionally active variants thereof, which are fragments, mutants, or hybrids thereof.

More specifically, the functionally active variant stimulates pDCs, thereby inducing an increased level of IL-6 and TNFalpha as compared to a negative control.

Specifically, the functionally active variant
a) has at least 60% homology to any of the peptides of SEQ ID 50-68;
b) is a mutant of any of the peptides of SEQ ID 50-68, obtainable by modifying the parent amino acid sequence by insertion, deletion or substitution of one or more amino acids within the sequence or at either or both of the distal ends of the sequence; or
c) is a fragment of any of the peptides of SEQ ID 50-68 comprising at least 5 amino acids.

Specific immunostimulatory peptides comprise a motif selected from the group consisting of EWWFYWP (SEQ ID 53), EWW (SEQ ID 125), WFY (SEQ ID 126), YWP (SEQ ID 127), and QVxI, x being any amino acid (SEQ ID 128).

The function of a TLR9 ligand or agonist or antagonist may be determined in a suitable assay, e.g. in the following way: pDCs are purified from blood of a healthy donor as described by Tel et al[41] and subsequently incubated with the appropriate concentration of the TLR9 ligand. After 24 h IFNa is measured in the supernatant using standard ELISA protocols. For determination of the maturation state of the cells, pDCs are stained for expression of CD80, CD83 or CD86 using standard FACS procedures with commercially available specific antibodies before and after the incubation with the TLR9 ligand.

The number of reactive T cells that are activated upon exposure to the vaccine according to the invention may be determined by a number of methods including ELISPOT, FACS analysis, cytokine release, or T cell proliferation assays.

As used herein, the term "specificity" or "specific binding" refers to a binding reaction which is determinative of the cognate ligand of interest in a heterogeneous population of molecules. Thus, under designated conditions (e.g. immunoassay conditions), one or more antigens are specifically bound by the respective binding site(s) of a binder, which does not bind in a significant amount to other molecules present in a sample. The specific binding means that binding is selective in terms of target identity, high, medium or low binding affinity or avidity, as selected. Selective binding is usually achieved, if the binding constant or binding dynamics is at least 10 fold different, preferably the difference is at least 100 fold, and more preferred a least 1000 fold. It is well-understood that the term shall also refer to cross-reactive or multispecific binders that specifically recognize one or more different antigens.

The term "treatment" as used herein shall always refer to treating subjects for prophylactic (i.e. to prevent infection and/or disease status) or therapeutic (i.e. to treat diseases regardless of their pathogenesis) purposes. Treatment of a subject will typically be therapeutic in cases of allergic, autoimmune or cancer disease conditions, or prophylactic in treating infectious disease conditions. Treatment of a subject will typically be therapeutic in cases of cancer disease conditions, including gastrin dependent tumors or gastrin dependent cancer. However, in case of patients suffering from a primary disease, which are at risk of disease progression or at risk of developing a secondary disease condition or side reaction, e.g. which is dependent on the endogenous gastrin production of gastrin effects, the treatment may be prophylactic.

Also in case of allergy patients at risk of developing the disease e.g. because of a family history of allergy, the treatment may be prophylactic.

Such treatment may be effected with the vaccine according to the invention as the sole prophylactic or therapeutic agent or else in combination with any suitable means, e.g. including chemotherapy, or the use of antacids.

The term "combination" as used in this regard, e.g. with respect to the combination of compounds or treatments specifically refers to the concomitant, simultaneous, parallel or consecutive treatment of a subject.

The following specific allergic diseases are treated according to the invention allergic rhinoconjunctivitis (hay fever), allergic asthma, allergic eczema, such as atopic eczema or atopic dermatitis.

For allergy therapy, particular additional therapeutic measures include application of (inhaled) corticosteroids combined with broncho-dilators in allergic asthma, steroid containing creams (atopic eczema) and in milder forms of allergy (e.g. hay fever), anti-histamines and specific immunotherapies.

Allergy, in which polarized Th2 responses, abundant IL-4/IL-13 secretion and IgE antibody response are inappropriate and harmful, is just an example of a failing immune response. Other examples are characterized by Th1-mediated conditions related to systemic autoimmune diseases.

Treatment of auto-immune diseases with the vaccine according to the invention may specifically among other examples refer to Diabetes, Guillain Barre syndrome, Systemic Lupus Erythematosis, Multiple sclerosis or thrombocytopenia.

Prophylaxis or therapy of infectious diseases employing the vaccine according to the present invention specifically refers to pathological conditions, such as microbial infections, i.e. conditions caused by bacterial, viral, fungal, protozoan or helminthic pathogens. For the purposes of the present invention, the term "pathogen" is used in a broad sense to refer to a specific causative agent of a disease or condition, and includes any agent that elicits an immune response. Pathogens include viruses, bacteria, fungi, protozoa, parasites, and the like. Typically, the immunogen is derived from one or more peptide, polypeptide, protein or carbohydrate antigens produced by a pathogen. Methods for identifying suitable antigens, obtaining and preparing such molecules, are well known in the art.

Treatment of infectious diseases caused by pathogens specifically refers to, e.g. hepatitis B, hepatitis C, Cholera, HIV, Pertussis, Influenza or Typhoid.

Immunotherapeutic methods of treating tumors as described herein specifically refer to methods and vaccines according to the invention for treating cervical, breast, colorectal, prostate, lung cancers, and melanomas.

In cancer therapy, additional therapeutic treatments include, for instance, surgical resection, radiation therapy, chemotherapy, hormone therapy, anti-tumor vaccines, antibody based therapies, whole body irradiation, bone marrow transplantation, peripheral blood stem cell transplantation, and the administration of chemotherapeutic agents.

For treatment the immunogenic composition or the vaccine according to the invention may be administered at once, or may be divided into the individual components and/or a number of smaller doses to be administered at intervals of time. The vaccine is typically administered at a concentration of 0.1 to 500 µg/mL, e.g. either subcutaneously, intradermal, intramuscularly, intravenously, orally, through inhalation or intranasally, with or without an additional adjuvant such as ALUM. It is understood that the precise dosage and duration of treatment is a function of the disease being treated and may be determined empirically using known testing protocols or by extrapolation from in vivo or in vitro test data.

The immunogenic composition or the vaccine of the present invention can be administered by any suitable means and respective formulations for including, but not limited to, for example, any of the parenteral (including subcutaneous, intramuscular, intravenous and intradermal) injection, or local injection into the affected site, such as joints or into or around the tumor. In a preferred embodiment the vaccine is provided in a formulation for intramuscular, subcutaneous or intradermal injection.

The invention also provides a delivery device, e.g. a syringe, pre-filled with the vaccine according to the invention.

Typically upon priming a subject by a first injection of a vaccine according to the invention, one or more booster injections may be performed over a period of time by the same or different administration routes. Where multiple injections are used, subsequent injections may be made, e.g. within 1 to 52 weeks of the previous injection, or even more.

The vaccine typically may contain diluents, such as water, saline, glycerol, ethanol, etc. Additionally, as auxiliary substances, such as wetting or emulsifying agents, pH buffering substances, and the like, may be present among excipients. Typically, the vaccine according to the invention is prepared as an injectable, either as liquid solutions or suspensions, or solid forms suitable for solution in, or suspension in, liquid vehicles prior to administration. The preparations also may be emulsified or encapsulated in liposomes.

Administration of the vaccine according to the invention may be suitably and additionally be combined with any of the TLR9 agonists or antagonists and/or further adjuvant measures to enhance the immunoregulatory effect or immune response. An enhanced immune response may include one or more of an enhanced Th1 immune response Th2 immune response Th17 immune response or Treg immune response.

An enhanced Th1 immune response may include an increase in one or more of the cytokines associated with a Th1 immune response (such as IFNγ), and an increase in activated macrophages.

An enhanced Th1 immune response may include one or more of an increase in antigen specific IgG antibodies, especially IgG1 antibodies.

For example, the immunogenic composition or the vaccine of the invention, may be in association (e.g. chemically or recombinantly linked, bound by affinity binding or a mixture of separate components) with one or more adjuvants and/or pharmaceutically acceptable excipients. The vaccine according to the invention may include one or more pharmaceutically acceptable excipients or vehicles, such as water, saline, glycerol, ethanol, etc. Additionally, auxiliary substances, such as wetting or emulsifying agents, pH buffering substances, and the like, may be present in such vehicles. Adjuvants may specifically be used to enhance the effectiveness of the vaccine. Adjuvants may be added directly to the vaccine compositions or can be administered separately, either concurrently with or shortly after, administration of the vaccine.

Suitable adjuvants include cytokines and similar compounds which help orchestrate an immune response to the immunogen. As used herein, the term "cytokine" is used as a generic name for a diverse group of soluble proteins and peptides which act as humoral regulators at nano-to picomolar concentrations and which, either under normal or pathological conditions, modulate the functional activities of individual cells and tissues. These proteins also mediate interactions between cells directly and regulate processes taking place in the extracellular environment.

Examples of cytokines include IL-1, IL-4, TNFα, IFNα, INFγ, GM-CSF, G-CSF

CpG oligonucleotides can also be used as an adjuvant in conjunction with presentation of respective epitopes. Other adjuvants include alum, (in)complete Freund's adjuvant, *B. pertussis* or its toxin, IC31, etc.

The components of the immunogenic composition, i.e. the directed adjuvant component, e.g. the anti-CD32 moiety linked to the TLR9 ligand and the first peptidic alpha-helix, and the immunogen component, e.g. comprising the peptide immunogen linked to the second peptidic alpha-helix that matches the first one, as well as the immunogenic composition or the vaccine, or any of its binding moieties or ligands and the immunogen with our without the coil repeats may be obtained by various methods known in the art, e.g. by purification or isolation from cell culture, recombinant technology or by chemical synthesis.

According to a specific embodiment, the immunogenic composition and/or the directed adjuvant component and/or the immunogen component thereof, is produced as a recombinant polypeptide, such as by recombinant DNA technology. As used herein, the term "recombinant" refers to a molecule or construct that does not naturally occur in a host cell. In some embodiments, recombinant nucleic acid molecules contain two or more naturally-occurring sequences that are linked together in a way that does not occur naturally. A recombinant protein refers to a protein that is encoded and/or expressed by a recombinant nucleic acid. In some embodiments, "recombinant cells" express genes that are not found in identical form within the native (i.e., non-recombinant) form of the cell and/or express native genes that are otherwise abnormally over-expressed, under-expressed, and/or not expressed at all due to deliberate human intervention. Recombinant cells contain at least one recombinant polynucleotide or polypeptide. "Recombination", "recombining", and generating a "recombined" nucleic acid generally encompass the assembly of at least two nucleic acid fragments. In certain embodiments, recombinant proteins and recombinant nucleic acids remain functional, i.e., retain their activity or exhibit an enhanced activity in the host cell.

Thus, the invention further refers to the production of the immunogenic composition or the components thereof, and the recombinant means for such production, including a nucleic acid encoding the amino acid sequence, an expression cassette, a vector or plasmid comprising the nucleic acid encoding the amino acid sequence to be expressed, and a host cell comprising any such means. Suitable standard recombinant DNA techniques are known in the art and described inter alia in Sambrook et al., "Molecular Cloning: A Laboratory Manual" (1989), 2nd Edition (Cold Spring Harbor Laboratory press).

The term "sensibilizing vaccine" is herein understood in the following way. A subject may undergo specific sensibilization to vaccine components apart from the immunogen, so to induce the specific humoral immune response. According to the present invention, a subject is e.g. sensibilized by treatment with the sensibilizing vaccine according to the invention, which comprises the directed adjuvant and the peptidic alpha-helix, preferably the coiled coil or double-helix to stabilize the molecule. Thus, the immunogen as used in the immunoregulatory vaccine according to the invention is specifically not employed in such sensibilizing vaccine. Upon administering such sensibilizing vaccine to a subject, the subject may develop the immune response against the epitopes of the sensibilizing vaccine. The further treatment of the same subject with the immunoregulatory vaccine according to the invention will then induce the specific immune response to the immunogen that is needed for treatment or prevention of the disease. Thanks to the sensibilization the potentially harmful existing immune memory to parts of the immunogen, e.g. in case allergic patients, will not induce unwanted immune reactions against those parts of the vaccine to which the patient is naïve before immunization.

Herein the term "subject" is understood to comprise human or mammalian subjects, including livestock animals, companion animals, and laboratory animals, in particular human beings, which are either patients suffering from a specific disease condition or healthy subjects.

The invention further provides a kit of components for preparing the immunogenic composition of the invention, e.g. a pharmaceutical kit comprising one or more containers filled with the components. The kits can be used in the above-described methods. In a particular embodiment, the kit further comprises instructions for using the components of the immunogenic composition or the prepared immunogenic composition or vaccine of the invention.

The vaccine components, i.e. the directed adjuvant component and the immunogen component, as well as the vaccine, or any of its binding moieties or ligands and the immunogen with our without the coil repeats may be obtained by various methods known in the art, e.g. by purification or isolation from cell culture, recombinant technology or by chemical synthesis.

Therefore, the present invention provides for a unique vaccine and respective applications.

According to a specific example, the vaccine according to the invention comprises a recombinant polypeptide of

```
SEQ ID 19:
EVQLQQSGPELKKPGETVKISCKASGYTFTNYGMNWVKQAPGKGLKWMG

WLNTYTGESIYPDDFKGRFAFSSETSASTAYLQINNLKNEDMATYFCAR

GDYGYDDPLDYWGQGTSVTVSSGGGGSGGGGSGGGGSDIVMTQAAPSVP

VTPGESVSISCRSSKSLLHTNGNTYLHWFLQRPGQSPQLLIYRMSVLAS

GVPDRFSGSGSGTAFTLSISRVEAEDVGVFYCMQHLEYPLTFGAGTKLE

LKGSISAWSHPQFEKGPEVSALEKEVSALEKEVSALEKEVSALEKEVSA

LEK
```

N-terminal underlined: sequence of ScFV specifically binding to CD32a;

Italic: Linker; any alternative linker commonly used in scFv preparations may be used.

Bold: StrepTag II for purification, any alternative tag may be used, e.g. flag tag or HIS tag.

C-terminal double underlined: heptad repeat alpha helix (pepE) to form the coiled coil with the counter heptad repeat alpha helix in the immunogen (pepK).

In this example (SEQ ID 19) 5 repeats are used; more repeats may cause auto-aggregation and less repeats may reduce the affinity. The preferred minimal functional number of repeats for the coils used is 3 and the preferred maximum functional number is $5^{42-44}$ but more repeats are feasible depending on which type of alpha helix is used. Limiting would be the number of repeats that start to induce homodimerization. Thus, homodimerization is specifically excluded.

Similar polypeptides may comprise a leader sequence, the amino acid sequence of a specific anti-CD32 moiety, which is e.g. a recombinant scFv, a linker, a tag for purification purposes and the sequence of the peptidic alpha-helix pepE. This construct with or without the TLR9 ligand is also called "warhead", which may then be used to construct a vaccine by combination with an immunogen linked to the counter alpha helix pepK.

According to another specific example, the anti-CD32 moiety is an anti-CD32a peptide with the sequence of SEQ ID 20: ADGAWAWVWLTETAVGAA[45] used as an alternative to the ScFv.

According to a further example, an immunogen containing coil comprising allergen, such as Der P1 and Der P2 T cell epitopes, is prepared. The peptidic alpha-helix is suitably linked to the immunogen by a linker to allow flexibility.

According to a further example, a stable coiled coil is established between the warhead scFv and the immunogen.

According to another example, the immunogen containing coil is prepared which comprises about 29 different T cell epitopes of an allergen.

In a further example it could be shown that the warhead mediated enhanced antigen presentation. T cells were effectively stimulated when the immunogen with the coil (the pepK coil) interacted with the warhead containing the counterpart coil (the pepE coil).

In a further example it has been proven that the TLR9 agonist CpG mediated activation of autoimmune reactive T cells.

Yet, in another example treatment of allergy is described, using a warhead employing either the anti-CD32 scFv or the anti-CD32a peptide linked by the coiled coil to the allergen specific immunogen.

According to a further example, a stable coiled coil is established between the warhead scFv and the immunogen.

It has proven that PBMC could be effectively stimulated with such immunogen or vaccine.

In a further example it could be shown that the warhead mediated enhanced antigen presentation. T cells were effectively stimulated when the immunogen with the coil (the pepK coil) interacted with the warhead containing the counterpart coil (the pepE coil).

In further examples treatment of pancreatic cancer in a mouse model and in a rhesus monkey model is described, using a warhead employing either the anti-CD32 scFv or the anti-CD32a peptide linked by the coiled coil to the G13 peptide immunogen. The appetite reduction and appetite control is described in the rhesus monkey model.

Therefore, the present invention provides for a unique immunogenic composition and vaccine, and respective applications.

The foregoing description will be more fully understood with reference to the following examples. Such examples are, however, merely representative of methods of practicing one or more embodiments of the present invention and should not be read as limiting the scope of invention.

EXAMPLES

Example 1

ScFV Warhead Containing Coil

```
Amino acid sequence 1.
                                              (SEQ ID 21)
1         10         20         30         40
MELGLSWIFL LAILKGVQCE VQLQQSGPEL KKPGETVKIS 50 51         60         70         80
CKASGYTFTN YNWVKQAPGK GLKWMGWLNT YTGESIYPDD 90        100 101        110        120
FKGRFAFSSE TSASTAYLQI NNLKGMNEDM ATYFCARGDY 130        140            150 151        160
GYDDPLDYWG QGTSVTVSSG GGGSGGGGSG SGGGDIVMTQ 170        180            190        200
AAPSVPVTPG ESVSISCRSS KSLLHTNGNT YLHWFLQRPG 201 210        220            230        240
QSPQLLIYRM SVLASGVPDR FSGSGSGTAF TLSISRVEAE 250 251        260            270        280
DVGVFYCMQH LEYPLTFGAG TKLELKGSIS AWSHPQFEKG 290        300 301        310        316
PEVSALEKEV SALEKEVSAL EKEVSALEKE VSALEK
```

AA 1-19: leader sequence (to secrete the product)

IAA 20-271 sequence of ScFV (the VH domain is underlined, VI is double underlined) order of VH and VL domain may be swapped)

IAA140-154 Linker may be changed to any linker used in ScFV preparation

AA 272-279: StrepTag II for purification may be exchanged to any type of tag e.g. flag tag or HIS tag.

AA280-281: short linker (maybe longer)

AA282-316: heptad repeat alpha helix (pepE) to form the coiled coil with the counter heptad repeat alpha helix in the immunogen (pepK). In the example 5 repeats are used, more repeats may cause auto-aggregation and less repeats will reduce the affinity, however 4 repeats are still functional. The minimal functional number of repeats for the coils used is 3 and 5[46-48]

A TRL9 agonist such as CpG may be coupled to the warhead using a chemical coupling e.g. using the Solulink antibody-oligo coupling KIT. A peptidic TRL9 agonist may be coupled using standard peptide chemistry.

Example 2

Peptide Warhead Containing Coiled Coil

```
Amino acid sequence 2 (SEQ ID 22):
1         10         20         30         40
ADGAWAWVWL TETAVGAAKG GGSWSHPQFE KGPEVSALEK 50 51         60         68
EVSALEKVS ALEKEVSALE KEVSALEK
```

AA1-19 sequence of aCD32a peptide published by Berntzen et al[45]

IAA20-24 and AA32-33: Linkers may be changed to any linker also longer linkers to allow flexibility between the two connected sequences.

AA24-31: StrepTag II for purification may be exchanged to any type of tag e.g. flag tag or HIS tag.

AA34-68: heptad repeat alpha helix (pepE) to form the coiled coil with the counter heptad repeat alpha helix in the immunogen (pepK). In the example 5 repeats are used, more repeats may cause autoaggregation and less repeats will reduce the affinity, however 4 repeats are still functional. The minimal functional number of repeats for the coils used is 3 and 5[49-51].

A TRL9 agonist such as CpG may be coupled to the warhead using chemical coupling e.g. using the Solulink antibody-oligo coupling KIT. A peptidic TRL9 agonist may be coupled using standard peptide chemistry.

Example 3

Immunogen 3 Containing Coil (Der P1 and Der P2 T Cell Epitopes Based on Human Class II Expression)

```
Amino acid sequence 3 (SEQ ID 23):
        10         20         30         40
HHHHHHYYRY VAREQSCRRP NAQRFGISNY CQIYPPNVNK 50         60         70         80
IREALAQTHS AIAVDLRQMR TVTPIRMQGG CGSCWAFSGV 90        100        110        120
AATESAYLQQ YDIKYTWNVP KIAPKSENVV VTVKVMGDDG 130        140        150        160
VLACAIATHA KIRDDAFRHY DGRTIIQRDN GYQPNYHAVN 170        180        190        200
IVGYSNAQGV DYWIVRNSWD TNWHEIKKVL VPGCHGSEPC 210        220        230        240
IIHRGKPFGG GSGGGSCGGK VSALKEKVSA LKEKVSALKE 250 254
KVSALKEKVS ALKE
```

AA1-6 His tag for purification may be exchanged to any type of tag e.g. flag tag or StrepTag II. Tag may also be positioned between linker and alpha helix see example 4). The C terminus is not preferred, since this may interfere with the functionality of the coiled coils.

AA208-219: linker between allergen peptides and linker (may be exchanged for any other linker to allow flexibility between the two connected sequences. The underlined cysteine may be removed from the sequence.

AA220-254: heptad repeat alpha helix (pepK) to form the coiled coil with the counter heptad repeat alpha helix in the warhead (pepE). In the example 5 repeats are used, more repeats may cause autoagreggataion and less repeats will reduce the affinity, however 4 repeats are still functional. The minimal functional number of repeats for the coils used is 3 and 5$^{52-54}$.

AA6-54: T cell epitopes from Der p1 (AA181-220 of native protein):

(SEQ ID 24)
Y*YRYVAREQS*CRRP*NAQRFGISNYCQIYPP*NANKI

REALAQTHSAIAV

Bold and italic are predicted T cell epitopes presented by HLA Class

AA55-88: T cell epitopes from Der p1 (95-128):

(SEQ ID 25)
D*LRQMRTVTPIRMQGGCGS*CWAFSGVAATESAYL

Bold and italic are predicted T cell epitopes presented by HLA Class

AA89-108: T cell epitopes from Der p2: (AA85-104 of native protein):

(SEQ ID 26)
*QQYDIKYT*WNVPKIAPKSEN

Bold and italic are predicted T cell epitopes presented by HLA Class

AA109-134: T cell epitopes from Der p2: (AA105-130 of native protein):

(SEQ ID 27)
*VVVTVKVMGD*DG*VLACAIATH*AKIRD

Bold and italic are predicted T cell epitopes presented by HLA Class

AA135-183: T cell epitopes from Der p1 (AA228-276 of native protein):

(SEQ ID 28)
DA*FRHYDG*RTI*IQRDNGY*QPNYHAVN*IVGYSNAQG*VDY

*WIVRNSWD*TNW

Bold and italic are predicted T cell epitopes presented by HLA Class

AA184-208: T cell enitones from DerP2: (AA11-45 of native protein):

(SEQ ID 29)
HE*IKKVLVPGC*HGSEPC*IIHRGKPF*

Bold and italic are predicted T cell epitopes presented by HLA Class

Example 4

Formation of a Stable Coiled Coil Between Warhead ScFV and Immunogen 3

Immunogen 3 was immobilized to a BIACore CM5 on flow cell 1, 2, 3 chip using standard procedures resulting in ~700 response units, subsequently warhead (10 µg/ml in PBS) was injected into flow cell 1 and a time dependent mass increase was measured (on rate), after ~160 seconds the buffer was changed to PBS only. The off rate indicates the stability of the binding between warhead and immunogen cell was injected with PBS only. When warhead was preincubated with the pepK coil and subsequently injected into flow cell 2, no binding of warhead to the chip was seen. Similarly when the chip was preincubated with pep E (flow cell 3) before injection with warhead no binding of the warhead to the immunogen was seen. (See FIG. 1)

Example 5

Immunogen 5-12 Containing Coil (~29 T Cell Epitopes of Der p1, Der p2, Der p3, Der p4, Der p7, Der p9, Der p10, Der p11, Der p14, Der p15, Based on Human Class II Expression

```
Amino acid sequence 3 (SEQ ID 30):
Immunogen 5-12:
        10         20         30         40
GVLACAIATH AKIREQERLV KLETVKKSLE QEVRTLHVRI 50         60         70         80
EEVEANALAG GDLRQMRTVT PIRMQGGCGS CWEAHEQQIR 90        100        110        120
IMTTKLKEAE ARQQYDIKYT WNVPKIAVNI VGYSNAQGVD 130        140        150        160
YWIVRNSWDT NWYHNPHFIG NRSVITHLME DLKGELDMRN
```

-continued

```
            170         180         190         200
     IQVRGLKQMK  RVGDANVKSE  DDAFRHYDGR  TIIQRDNGYQ 210         220         230         240
     PNYLDEYWIL  TAAHCVDGQT  VSKLIRSKVL  GEKISYYRYV 250         260         270         280
     AREQSCRRPN  AQRFGISNYC  VVVTVKVMGD  DELHTYFNVN 290         300         310         320
     YTMHYYLNNG  ATRDILDEYW  ILTAAHCVAG  QTASKLSIRY 330         340         350         360
     NSLKHSLFKY  RPFKVNELNL  EGEFGRELQH  KFRLMRNSQM 370         380         390         400
     EVEEGGGSHH  HHHHGGGSCG  GKVSALKEKV  SALKEKVSAL 410    416
     KEKVSALKEK  VSALKE
```

AA1369-274 His tag for purification may be exchanged to any type of tag e.g. flag tag or StrepTag II. Tag may also be positioned between linker and alpha helix see example 4). The C terminus is not preferred, since this may interfere with the functionality of the coiled coils.

AA365-368 and 375-381: linkers between allergen peptides HIS tag and pepK. The linkers (may be exchanged for any other linker to allow flexibility between the two connected sequences. The underlined cysteine (Cys379) is preferably removed from the sequence.

AA382-416: heptad repeat alpha helix (pepK) to form the coiled coil with the counter heptad repeat alpha helix in the warhead (pepE). In the example 5 repeats are used, more repeats may cause autoagreggation and less repeats will reduce the affinity, however 4 repeats are still functional. The minimal functional number of repeats for the coils used is 3 and 5[55]-57.

Warhead (based on ScFVcoil1 IV.3+ODNM362) is mixed with Immunogen 5-12 in a ratio which indicates that 10% to 100% of warhead is bound to the immunogen by the coiled-coil structure, preferably wherein no free or less than 50% free immunogen, and formulated on Alum.

As an example and further described below, according to a preferred embodiment, the invention provides for a vaccine wherein the immunoregulatory vaccine of the invention comprises

- a directed adjuvant that is composed of the anti-CD32 moiety linked to the first alpha-helix comprising or consisting of the sequence of SEQ ID 70, which is coupled to the TLR9 ligand of SEQ ID 69, e.g. in a ratio of 1:1-18 (molecule per molecule); and
- an immunogen that comprises or consists of the immunogen of SEQ ID 30 linked to the second alpha-helix, or a functionally active variant thereof, preferably a variant, wherein Cys379 is removed, or wherein the order of the allergen-derived peptides is changed, wherein the directed adjuvant and the immunogen are bound to each other by the coiled-coil structure formed by the first and second alpha-helices.

T cell epitopes (there are 15 allergen derived peptides in immo5-12: 1-2-3-4-5-6-7-8-9-10-11-12-13-14-15) The order of peptides derived from HDM allergens was optimized for solubility but any other order will be possible as well.

1) AA: 1-14 Der p2 (AA116-129 of native protein)

G*VLACAIATH*AKIR (SEQ ID 31)

Bold and italic are predicted T cell epitopes presented by HLA Class

2) AA: 15-51 Der p11 (AA697-733 of native protein)

(SEQ ID 32)
EQER*LVKLETVKKS*LEQE*VRTLHVRIEEVEAN*ALAGG

Bold and italic are predicted T cell epitopes presented by HLA Class

3) AA: 52-72 Der D1 (AA95-115 of native protein)

D*LRQMRTVTPIRMQGGC**GS*CW

Bold and italic are predicted T cell epitopes presented by HLA Class

4) AA: 73-92 Der p10 (AA219-238 of native protein)

EAHEQQ*IRIMTTKLK*EAEAR (SEQ ID 34)

Bold and italic are predicted T cell epitopes presented by HLA Class

5) AA: 93-106 Der p2: (AA85-98 of native protein)

*QQYDIKYT*WNVPKI (SEQ ID 35)

Bold and italic are predicted T cell epitopes presented by HLA Class

6) AA: 107-132 Der p1 (AA251-276 of native protein)

AVN*IVGYSNAQG*VDY*WIVRNSWD*TNW (SEQ ID 104)

Bold and italic are predicted T cell epitopes presented by HLA Class

7) AA: 133-150 Der p4 (AA2-19 of native protein):

YHNPH*FIGNRSVITHL*ME (SEQ ID 105)

Bold and italic are predicted T cell epitopes presented by HLA Class

8) AA: 151.181 Der p7 (AA66-96 of native protein):

(SEQ ID 36)
DLKGELD*MRNIQVRGLKQMKRVGD*ANVKSED

Bold and italic are predicted T cell epitopes presented by HLA Class

9) AA: 182-203 Der p1 (AA228-252 of native protein)

(SEQ ID 37)
DA*FRHYDG*RT*IIQRDNGY*QPNY

Bold and italic are predicted T cell epitopes presented by HLA Class

10) AA: 204-235 Der n9 (AA54-85 of native protein):

(SEQ ID 38)
LDE*YWILTAAHCV*GQT *VSKLIRSKVLGEK*IS

Bold and italic are predicted T cell epitopes presented by HLA Class

11) AA: 236-260 Der p1 (AA181-205 of native protein)

(SEQ ID 39)
Y*YRYVAREQS*CRRP*NAQRFGIS*NYC

Bold and italic are predicted T cell epitopes presented by HLA Class

12) AA: 261-271 Der p2 (AA105-115 of native protein)

(SEQ ID 40)
*VVVTVKVMGD*D

Bold and italic are predicted T cell epitopes presented by HLA Class

13) AA: 272-294 Der p15 (AA251-273 of native protein)

(SEQ ID 41)
ELHTY*FNVNYTMHYYLNNGA*TRD

Bold and italic are predicted T cell epitopes presented by HLA Class

14) AA: 295-327 Der p3 (AA58-90 of native protein)

(SEQ ID 42)
ILDE*YWILTAAHCV*AGQTASKLS*IRYNSLKHS*L

Bold and italic are predicted T cell epitopes presented by HLA Class

15) AA: 328-364 Der p14 (AA1061-1097 of native protein)

(SEQ ID 43)
FK*YRPFKVNEL*NLEGEFGRE*LQHKFRLMRNSQMEV*EE

Bold and italic are predicted T cell epitopes presented by HLA Class

Example 6

Stimulation of Monkey PBMC with Immunogen 3

PBMC (100.000/well) of Der p1 sensitized rhesus monkeys (macaca mulatta) were cultured in triplicate with medium, 3 Der p1 or 3 and 5 µg/ml immunogen 3 at 37° C./5% $CO_2$. in the presence of 20 U/ml IL-2. Proliferation was assayed by the incorporation of [$^3$H]-thymidine (0.5 µCi/well) during the final 18 hrs of a 2-day culture. Cells were harvested for β-scintillation counting (Topcount NXT, Packard, Ramsey, Minn., USA). Results are shown as counts per minute. In addition from parallel cultures, supernatants were assayed in duplicate for IL-10 and GM-CSF levels using a commercially-available ELISA kit (U-Cytech, Utrecht, The Netherlands) in accordance with the manufacturer's instructions. See FIG. 2.

There is non-significant difference between the response to Der p1 or to immunogen 3 neither in proliferation nor in cytokine production, indicating that the T cell epitopes in immunogen 3, which were selected on the basis of human HLA Class II expression, are equally well presented by rhesus monkey class II molecules.

Example 7

WH Mediated Enhanced Antigen Presentation

PBMC (100.000/well) of Der p1 sensitized rhesus monkeys (macaca mulatta) were preincubated (30 min on ice) with 1 µg/ml of warhead ScFV and washed 3 times with PBS or preincubated with PBS only and washed three times. Subsequently these cells incubated (30 min on ice) with different concentrations of Immunogen 3 or Der p1 at 3 µg/ml and washed 3 times with PBS after which the cells were culture at 37° C./5% $CO_2$ in the presence of 20 U/ml IL-2 for 48 hours. As a positive control PBMCs (without warhead preincubation) were incubated with 3 µg/ml Der Pb without washing and cultured at 37° C./5% $CO_2$ in the presence of 20 U/ml IL-2. Proliferation was assayed by the incorporation of [$^3$H]-thymidine (0.5 µCi/well) during the final 18 hrs of a 2-day culture. Cells were harvested for β-scintillation counting (Topcount NXT, Packard, Ramsey, Minn., USA). Results are shown as counts per minute. See FIG. 3.

In order to stimulate T cells, antigen needs to be internalized and processed by antigen presenting cells. This can be achieved by culturing the T cells and APC in the presence of antigen or by targeting the antigen to a cell surface receptor able to internalize and relocate into lysosomes[58-62]. In agreement with the literature, stimulation of PBMC with preincubated immunogen in the absence of warhead did not lead to proliferation (data not shown). Also preincubation with Der p1 in the presence of warhead did not lead to proliferation. However when PBMC were preincubated with 1 µg/ml warhead ScFV washed and subsequently incubated with different immunogen 3 concentrations and washed a dose dependent stimulation was seen, which was even higher than the positive control where PBMC were cultured 48 h in the presence of 3 µg/ml Der p1 without washing. So, only when immunogen (containing the pepK coil) was able to interact with the warhead (containing the pepE coil) so that a stable coiled coil was formed, a stimulation was seen. Warhead with in combination with Der P1 did not lead to stimulation since Der P1 lacks the coil and does not bind to PBMCs.

Example 8

CpG Mediated Activation of Autoimmune Reactive T Cells

PBMC (100.000/well) of rhesus monkeys (macaca mulatta) or normal human donors were incubated in triplicate with 50 µM CpG or CpG-biot. In parallel PBMCs were preincubated (30 min on ice) 1 µg/ml biotinylated warhead ScFV washed 3× and subsequently incubated with 50 µM CpG. Supernatants were assayed in duplicate for IL-4 and IFN gamma levels using a commercially-available ELISA kit in accordance with the manufacturer's instructions. See FIG. 4.

CpG did not induce a specific T cell response in monkey or human cells (left bars) nor did it enhance or induce a T cell response against the biotinylated protein that was co administered (right bars). Only when CpG and biotin were physically linked (green bars) a specific response against biotin was induced. Since biotin (also called vitamin b7, vitamin H or vitamin B8) is a self molecule, no immune response should occur. However when biotin is presented by TLR9 activated APC T cell tolerance is broken indicating that physically linking a TLR9 agonist to as self protein is will lead to an immune response that in the case the self protein is a tumor associated antigen (TAA) can be used to treat cancer. Physically linked means either directly coupled to the TAA or indirectly using the warhead and a TAA coupled with (or containing) a coil that interacts with the coil of the warhead. The latter is preferred. Any other form of complex between TRL9 agonist and TAA can be used as well, as long as it is assured that TLR9 agonist and TAA are taken up by the same APC.

Example 9

Cancer Treatment

In contrast to treating allergy, the warhead that is used for treatment of cancer should bind predominantly to CD32a and not to CD32b. The warhead from example 1 and 2 are preferred for use in cancer treatment.

Example 10

Stimulation of Human PBMC with Immunogen 5-12

PBMC (100.000/well) of Der p1 sensitized normal donors were cultured in triplicate with medium, 3 µg/ml Der p1 or 5, 1 or 0.5 µg/ml immunogen 5-12 (Immo5-12) at 37° C./5% $CO_2$ for 24 h. Supernatants were assayed in duplicate for IL-10 and IFNg levels using a commercially-available ELISA kits (eBioscience) in accordance with the manufacturer's instructions. See FIG. 5.

Example 11

Treatment of Auto-immune Diseases

A vaccine comprising a warhead that recognizes CD32a and CD32b a coiled coil and a TLR9 antagonist or an agonist that induces inhibitory TLR9 signalling (references) combined with an autoantigen. Such a vaccine will not induce new antibodies against any part of the vaccine including the autoantigen and is therefore safe for use in such patients. The use of an inhibitory CpG (inhibitory ODN) in this vaccine will induce T reg cell against the vaccine including the autoantigen. The same will happen when a CpG agonist of group 1 or 2 is used. A TLR9 agonist of group 3 is not preferred while this will lead to induction of more autoimmunity see FIG. 4.

Example 12

Exemplary Binders 12.1. CD32 Binding Region, Herein Also Called Anti-CD32 Moiety or CD32 Binder
CD32a Binders:
  Antibody specifically binding to CD32a: mAb IV.3 (Stuart et al. (1987) J. Exp. Med. 166: 1668)
  ScFV derived from mAb IV.3 (VH-linker-VL):

(SEQ ID 44)
<u>EVQLQQSGPELKKPGETVKISCKASGYTFTNYGMNWVKQAPGKGLKWMGW</u>

<u>LNTYTGESIYPDDFKGRFAFSSETSASTAYLQINNLKNEDMATYFCARGD</u>

<u>YGYDDPLDYWGQGTSVTVSS</u>GGGGSGGGGSGGGGSDIVMTQAAPSVPTP

GESVSISCRSSKSLLHTNGNTYLHWFLQRPGQSPQLLIYRMSVLASGVPD

RFSGSGSGTAFTLSISRVEAEDVGVFYCMQHLEYPLTFGAGTKLELKGSI

Underlined: VH domain
  Bold: HL domain
  Normal type set. Flexible linker (maybe any linker)

Anti-CD32a Peptide: Berntzen et al. (J. Biol. Chem. (2009) 284: 1126-1135):

(SEQ ID 45)
ADGAWAWVWLTETAVGAAK

Group CD32a+b Binders:
  Antibody specifically binding to CD32a and CD32b: mAb AT-10 (AbD Serotec) ScFV derived from mAb AT-10 (VH-linker-VL):

(SEQ ID 46)
<u>EVKLEESGGGLVQPGGSMKLSCVASGFTFSYYWMNWVRQSPEKGLEWVAE</u>

<u>IRLKSNNYATHYAESVKGRFTISRDDSKNNVYLQMNNLRAEDTGIYYCNR</u>

<u>RDEYYAMDYWGQGTSVSVSS</u>GGGGSGGGGSGGGGSDIVLTQSPGSLAVSL

GQRATISCRASESVDNFGISFMNWFQQKPGQPPRLLIYGASNQGSGVPAR

FSGSGSGTDFSLNIHPVEEDDAAMYFCQQSKEVPWTFGGGTKLEIKGSI

Underlined: VH domain
  Bold: HL domain
  Normal type set. Flexible linker (maybe any linker)
  IgG1 Fc fragment (CH2-CH3 domain):

(SEQ ID 47)
(PKSCDKTHTCPPCP)<u>PELLGGPSVFLFPPKPKDTLMISRTPEVTCVVVD</u>

<u>VSHEDPEVKFNWYVDGVEVHNAKTKPREEQYNSTYRVVSVLTVLHQDWLN</u>

<u>GKEYKCKVSNKALPAPIEKTISKAKGQP</u>REPQVYTLPPSRDELTKNQVSL

TCLVKGFYPSDIAVEWESNGQPENNYKTTPPVLDSDGSFFLYSKLTVDKS

RWQQGNVFSCSVMHEALHNHYTQKSLSLSPGK

Between ( ) is hinge region may be omitted
  Underlined: CH2 domain
  Bold: CH3 domain 12.2 TLR9 Binding Region or Moiety, Herein Also Called TLR9 Binder or TLR9 Ligand
CpG Class A
  Group CpG-A:

ODN2216:
(SEQ ID 48)
GGGGGACGATCGTCGGGGGG

CpG Class B
  Group CpG-B:
  Natural ligands:

ODN2006:
(SEQ ID 49)
TCGTCGTTTTGTCGTTTTGTCGTT

Peptidic ligands (immunostimulatory peptides):

| Name | SEQ ID | Sequence |
| --- | --- | --- |
| 12-2 | 50 | ESWDKFLSHYLP |
| 7-6 | 51 | TDWSWFY |
| 7-7 | 52 | YPVYWPW |
| 7-12 | 53 | EWWFYWP |

| Name | SEQ ID | Sequence |
|---|---|---|
| 7-13 | 54 | WFPIEWW |
| 7-37 | 55 | DQVDIGY |
| 7-38 | 56 | THQVYIS |
| 7-12/13 | 57 | WFPIEWWFYWP |
| 12-1 | 58 | DSWQAFLTKFVL |
| 12-3 | 59 | HDIQWFWQHWNS |
| 12-4 | 60 | WSWWDHTFNYML |
| 12-6 | 61 | TTQQTWNVRYPY |
| 12-8 | 62 | DHTMPWTRNAKN |
| 12-12 | 63 | SWDPYWPFPWFS |
| 12-14 | 64 | AIYYVPSPMFTV |
| 12-16 | 65 | ETTLLKMWLAQM |
| 12-18 | 66 | YPWLDVAVVSLY |
| 12-20 | 67 | VPGWHYLATLRA |
| 12-21 | 68 | FDPLGSRDIKGS |

Such immunostimulatory peptides may be preferably used as a CpG mimic. Likewise functionally active variants thereof may be used, which are fragments, mutants, or hybrids, including combinations thereof.

Functionally active variants are specifically characterized in that they stimulate pDCs, thereby inducing an increased level of IL-6 and/or TNFalpha and/or IFNalpha, as compared to a negative control.

Functionally active variants of the immunostimulatory TLR9 binding peptides specifically a) have at least 60% homology or sequence identity to any of the peptides of SEQ ID 73-91, preferably at least 70%, at least 80% or at least 90%;

b) are mutants of any of the peptides of SEQ ID 50-68, obtainable by modifying the parent amino acid sequence by insertion, deletion or substitution of one or more amino acids within the sequence or at either or both of the distal ends of the sequence, preferably less than 5, 4, 3, 2 or 1 point mutations; or c) are fragments of any of the peptides of SEQ ID 50-68 comprising at least 50% of the parent sequence, or at least 60%, at least 70%, at least 80%, or at least 90%; or at least 5 amino acids, preferably at least 6, at least 7, at least 8, at least 9, at least 10 or at least 11 amino acids.

CpG Class C
Group CpG-C
ODNM362: (SEQ ID 69)
TCGTCGTCGTTCGAACGACGTTGAT 12.3 Exemplary CD32 Binding Products with Coils ScFV-coil 1 (IV.3):
(SEQ ID 70)
EVQLQQSGPELKKPGETVKISCKASGYTFTNYGMNWVKQAPGKGLKWMG

WLNTYTGESIYPDDFKGRFAFSSETSASTAYLQINNLKNEDMATYFCAR

GDYGYDDPLDYWGQGTSVTVSSGGGGSGGGGSGGGGSDIVMTQAAPSVP

VTPGESVSISCRSSKSLLHTNGNTYLHWFLQRPGQSPQLLIYRMSVLAS

GVPDRFSGSGSGTAFTLSISRVEAEDVGVFYCMQHLEYPLTFGAGTKLE

LKGSISAWSHPQFEKGPEVSALEKEVSALEKEVSALEKEVSALEKEVSA

LEK

Underlined: VH domain
Bold: HL domain
Normal type set. Flexible linker (maybe any linker)
In italics: pepE coil plus C' StrepTag II sequence and "GP" linker may be any flexible linker (StrepTag II may be removed or replaced by HIS Tag or any other tag)

ScFV-coil 2 (AT10):
(SEQ ID 71)
EVKLEESGGGLVQPGGSMKLSCVASGFTFSYYWMNWVRQSPEKGLEWVA

EIRLKSNNYATHYAESVKGRFTISRDDSKNNVYLQMNNLRAEDTGIYYC

NRRDEYYAMDYWGQGTSVSVSSGGGGSGGGGSGGGGSDIVLTQSPGSLA

VSLGQRATISCRASESVDNFGISFMNWFQQKPGQPPRLLIYGASNQGSG

VPARFSGSGSGTDFSLNIHPVEEDDAAMYFCQQSKEVPWTFGGGTKLEI

KGSISAWSHPQFEKGPEVSALEKEVSALEKEVSALEKEVSALEKEVSAL

EK

Underlined: VH domain
Bold: HL domain
Normal type set. Flexible linker (maybe any linker)
In italics: pepE coil plus at C' StrepTag II sequence and "GP" linker may be any flexible linker (StrepTag II may be removed or replaced by HIS Tag or any other tag)

Peptide-coil:
(SEQ ID 72)
ADGAWAWVWLTETAVGAAKGPEVSALEKEVSALEKEVSALEKEVSALE

KEVSALEK

In italics: pepE coil plus "GP" linker may be any flexible linker

IgG1 Fc fragment-coil:
(SEQ ID 73)
(PKSCDKTHTCPPCP)PELLGGPSVFLFPPKPKDTLMISRTPEVTCVVV

DVSHEDPEVKFNWYVDGVEVHNAKTKPREEQYNSTYRVVSVLTVLHQDW

LNGKEYKCKVSNKALPAPIEKTISKAKGQPREPQVYTLPPSRDELTKNQ

VSLTCLVKGFYPSDIAVEWESNGQPENNYKTTPPVLDSDGSFFLYSKLT

VDKSRWQQGNVFSCSVMHEALHNHYTQKSLSLSPGKGPEVSALEKEVSA

LEKEVSALEKEVSALEKEVSALEK

Between ( ) is hinge region may be omitted
Underlined: CH2 domain
Bold CH3 domain
In italics: pepE coil plus "GP" linker may be any flexible linker 12.4. Exemplary TLR9 Binding Products with SH Group for Chemical Cross-linking to the CD32 Binder Group CpG-A:

ODN2216_SH:

(SEQ ID 48)

GGGGGACGATCGTCGGGGGG-SH

In bold flexible linker with SH group for chemical cross-linking to ScFV-coil (Maybe any linker and chemically reactive group e.g NH2 suited for chemical crosslinking)

Group CpG-B:
Natural ligands:

ODN2006_SH:

(SEQ ID 49)

TCGTCGTTTTGTCGTTTTGTCGTT-SH

Peptidic ligands_SH:

| Name | SEQ ID | Sequence |
|---|---|---|
| 12-12_SH | 106 | SWDPYWPFPWFSGGGS-SH |
| 7-6_SH | 107 | TDWSWFYGGGS-SH |
| 7-7_SH | 108 | YPVYWPWGGGS-SH |
| 7-12_SH | 109 | EWWFYWPGGGS-SH |
| 7-13_SH | 110 | WFPIEWWGGGS-SH |
| 7-37_SH | 111 | DQVDIGYGGGS-SH |
| 7-38_SH | 112 | THQVYISGGGS-SH |
| 7-12/13_SH | 113 | WFPIEWWFYWPGGGS-SH |
| 12-1_SH | 114 | DSWQAFLTKFVLGGGS-SH |
| 12-2_SH | 115 | ESWDKFLSHYLPGGGS-SH |
| 12-3_SH | 116 | HDIQWFWQHWNSGGGS-SH |
| 12-4_SH | 117 | WSWWDHTFNYMLGGGS-SH |
| 12-6_SH | 118 | TTQQTWNVRYPYGGGS-SH |
| 12-8_SH | 119 | DHTMPWTRNAKNGGGS-SH |
| 12-14_SH | 120 | AIYYVPSPMFTVGGGS-SH |
| 12-16_SH | 121 | ETTLLKMWLAQMGGGS-SH |
| 12-18_SH | 122 | YPWLDVAVVSLYGGGS-SH |
| 12-20_SH | 123 | VPGWHYLATLRAGGGS-SH |
| 12-21_SH | 124 | FDPLGSRDIKGSGGGS-SH |

In bold flexible linker with SH group for chemical cross-linking to ScFV-coil (maybe any linker and chemically reactive group e.g. NH2 suited for chemical crosslinking)

Group CpG-C

ODNM362_SH:

(SEQ ID 69)

TCGTCGTCGTTCGAACGACGTTGAT-SH

In bold flexible linker with SH group for chemical cross-linking to ScFV-coil (maybe any linker and chemically reactive group e.g NH2 suited for chemical crosslinking)

12.5 Exemplary Warhead, i.e. a Structure Comprising a CD32 Binder and a TLR9 Binder Any representative from the group of CD32 binders chemically linked by any method with any representative of the group of TLR9 binders, where preferably the TLR9 binders are coupled to available Lysines (K) in the CD32 binders e.g. Also mixtures of different TLR9 binders may be coupled e.g. CpG-B natural or peptidic binders.

ScFV-coil1 (IV.3)

(SEQ ID 70)

EVQLQQSGPELKKPGETVKISCKASGYTFTNYGMNWVKQAPGKGLKWMGW

LNTYTGESIYPDDFKGRFAFSSETSASTAYLQINNLKNEDMATYFCARGD

YGYDDPLDYWGQGTSVTVSSGGGGSGGGGSGGGGSDIVMTQAAPSVPVTP

GESVSISCRSSKSLLHTNGNTYLHWFLQRPGQSPQLLIYRMSVLASGVPD

RFSGSGSGTAFTLSISRVEAEDVGVFYCMQHLEYPLTFGAGTKLELKGSI

SAWSHPQFEKGPEVSALE*K*EVSALE*K*EVSALE*K*EVSALE*K*

EVSALE*K*

Lysines in coil structure (Italic) are preferred or

Peptide-coil:

(SEQ ID 72)

ADGAWAWVWLTETAVGAAKGPEVSALE*K*EVSALE*K*EVSALE*K*

EVSALE*K*EVSALE*K*

Lysines in coil structure (Italic) are preferred 12.6. Exemplary Immunogen, Herein Also Called Antigen Immunogen 3 containing coil (Der P1 and Der P2 T cell epitopes based on human Class II expression)

(SEQ ID 74)

HHHHHHYYRYVAREQSCRRPNAQRFGISNYCQIYPPNVNKIREALAQTHS

AIAVDLRQMRTVTPIRMQGGCGSCWAFSGVAATESAYLQQYDIKYTWNVP

KIAPKSENVVVTVKVMGDDGVLACAIATHAKIRDDAFRHYDGRTIIQRDN

GYQPNYHAVNIVGYSNAQGVDYWIVRNSWDTNWHEIKKVLVPGCHGSEPC

IIHRGKPFGGGSGGGS*GGKVSALKEKVSALKEKVSALKEKVSALKEKVSA*

*LKE*

Underlined: HIS tag (may be removed)

In bold: a linker (can be any linker)

In italics: the pepK coil for interaction with warhead

Immunogen 5-12 containing coil (~29 T cell epitopes of Der p1, Der p2, Der p3, Der p4, Der p7, Der p9, Der p10, Der p11, Der p14, Der p15, based on human Class II expression)

(SEQ ID 75)

GVLACAIATHAKIREQERLVKLETVKKSLEQEVRTLHVRIEEVEANALAG

GDLRQMRTVTPIRMQGGCGSCWEAHEQQIRIMTTKLKEAEARQQYDIKYT

WNVPKIAVNIVGYSNAQGVDYWIVRNSWDTNWYHNPHFIGNRSVITHLME

DLKGELDMRNIQVRGLKQMKRVGDANVKSEDDAFRHYDGRTIIQRDNGYQ

PNYLDEYWILTAAHCVDGQTVSKLIRSKVLGEKISYYRYVAREQSCRRPN

AQRFGISNYCVVVTVKVMGDDELHTYFNVNYTMHYYLNNGATRDILDEYW

-continued

ILTAAHCVAGQTASKLSIRYNSLKHSLFKYRPFKVNELNLEGEFGRELQH

KFRLMRNSQMEVEEGGGSHHHHHHGGGSCGGKVSALKEKVSALKEKVSAL

KEKVSALKEKVSALKE

Underlined: HIS tag (may be removed)
In bold: a linker (can be any linker)
In italics: the pepK coil for interaction with warhead

12.7 Exemplary Allergy Vaccine SG100 Against House Dust Mite (HDM)

The exemplary molecule complex is formed by chemical linkeage, fusion and/or affinity binding, in particular by a coiled-coil structure.

Warhead (based on ScFVcoil1 IV.3+ODNM362) is mixed with Immunogen 5-12 in a ratio which indicates 90% of warhead is complexed with immunogen, no free immunogen (molar ratio of ~1:1.5) and formulated on Alum.

12.8 Efficacy of SG100 in Rhesus Monkeys:

Methods:
5 healthy house dust mite (HDM) naïve rhesus monkeys were immunized 3× with SG100 (100 μg/shot) absorbed on Alum) on d0, d14 and d28. Blood samples were taken on d0 and d49 for T cell activation and antibody production.

Antibody Immune Response:
Serum samples were tested in standard ELISA for IgG antibodies against warhead, immo 5-12 (Immo5), Der p1, Der p2, Der p5 and Der p7. The antigens were coated to maxisorb plates (1 μg/ml I PBS) overnight at 4° C., washed twice, blocked with PBS 1% BSA, washed twice incubated with the sera in a 1:1000 dilution for 1 h at 4° C., washed twice and subsequently detected with anti-human-IgG-PO (cross reactive with rhesus monkey IgG).

Cellular Immune Response:
Proliferation: PBMC ($10^5$/well) were cultured for 4 days (37° C./5% $CO_2$/99% humidity) in 8 plex with medium, warhead (2 μg/ml), Immunogen (2 μg/ml), Der p1 (2 μg/ml), Der p2 (2 μg/ml), Der p5 (2 μg/ml) and Der p7 (2 μg/ml). As positive control Con A (Concanavaline A, Sigma) was used. Proliferation was measured by [$^3$H]-thymidine (0.5 μCi/well) during the final 18 hrs of a 4 day culture. Cells were harvested for β-scintillation counting (Topcount NXT, Packerd, Ramsey, Minn., USA). Net counts per minutes were calculated by subtracting the counts of the medium control from the counts induced by the different antigens.

Cytokine Production:
From each well of the 8plex stimulations of the proliferation experiment, 50 μl supernatant was taken after 24 h and pooled. The pooled supernatants were tested for the presence of IFNγ and IL-4 using commercially available ELISA kits from U-Cytech, Utrecht The Netherlands).

Results:
Antibody Responses:
Strong IgG responses were measured against the warhead and the immunogen of SG100, but no antibodies were detected against Der p1, Der p2, Der p5 or Der p7 (FIG. 7), indicating that the animals were naive for the tested HDM allergens and that SG100 does not contain B cell epitopes, which cross-react with the tested HDM allergens.

T Cell Response:
In FIG. 8 it can be seen that the animals showed strong proliferation when stimulated in vitro with warhead, immo5, Der p1, Der p2, Der p7, but not against Der p5. Also IFNγ but no IL-4 was measured in supernatants from in vitro cultures with warhead, immo5, Der p1, Der p2, Der p7 but not against Der p5. (FIG. 9). IL-4 was seen after stimulation with Con A (data not shown).

Conclusion:
Immunization with SG100 induces a Th1 type memory response against the vaccine as indicated by the presence of IgG antibodies as well the induction of T cells which produce IFNγ but not IL-4 when stimulated by warhead or Immo5. As expected, no IgG (=B cell memory) against Der p1, Der p2, Der p5 or Der p7 was induced because the vaccine does not contain B ell epitopes from these allergens. However, Th1 type memory, was induced against the T cell epitopes of the house dust mite allergens which are present in the vaccine Der p1, Der p2, Der p7. No Th1 type memory is induced against Der p5, which is not included in the vaccine.

This confirms the concept of SG100.

12.9 Exemplary Vaccine, Warhead for Use in Oncology

ScFV-coil 1 (IV.3):

(SEQ ID 70)

EVQLQQSGPELKKPGETVKISCKASGYTFTNYGMNWVKQAPGKGLKWMGW

LNTYTGESIYPDDFKGRFAFSSETSASTAYLQINNLKNEDMATYFCARGD

YGYDDPLDYWGQGTSVTVSSGGGGSGGGGSGGGGSDIVMTQAAPSVPVTP

GESVSISCRSSKSLLHTNGNTYLHWFLQRPGQSPQLLIYRMSVLASGVPD

RFSGSGSGTAFTLSISRVEAEDVGVFYCMQHLEYPLTFGAGTKLELKGSI

*SAWSHPQFEKGPEVSALEKEVSALEKEVSALEKEVSALEKEVSALEK*

Underlined: VH domain
Bold: HL domain
Normal type set. Flexible linker (maybe any linker)
In italics: pepE coil plus C' StrepTag II sequence and "GP" linker may be any flexible linker (StrepTag II may be removed or replaced by HIS Tag or any other tag)

Warhead with ODNM362:

EVQLQQSGPELKKPGETVKISCKASGYTFTNYGMNWVKQAPGKGLKWMGW

LNTYTGESIYPDDFKGRFAFSSETSASTAYLQINNLKNEDMATYFCARGD

YGYDDPLDYWGQGTSVTVSSGGGGSGGGGSGGGGSDIVMTQAAPSVPVTP

GESVSISCRSSKSLLHTNGNTYLHWFLQRPGQSPQLLIYRMSVLASGVPD

RFSGSGSGTAFTLSISRVEAEDVGVFYCMQHLEYPLTFGAGTKLELKGSI

SAWSHPQFEKGPEVSALEKEVSALEKEVSALEKEVSALEK

EVSALEK

ODNM362_SH (SEQ ID 69)

TCGTCGTCGTTCGAACGACGTTGAT-SH

ODN-M362 may be coupled to any of the available lysines in ScFV-1-coil

Warhead (SG100):
ScFV-1-coil chemically linked with ODN-M362-SH. The preparation is a mix of ScFV-1-coil linked with 1 to 18 molecules ODN-M362 preferred is a mix with 1-6 molecules ODN-M362 coupled to ScFV-1-coil. All these mixes may be named warhead or ScFv-1-coil-M362.

Background:
Oncological targets for active immunotherapy are almost per definition autoantigens which are over expressed on tumour cells. These antigens are called tumour associated antigens (TAA) and the immune system is not able to respond against these antigens because they are recognized as self. A vaccine formulation that enables the immune system to generate a specific antibody and/or cellular immune response against an autoantigen is potentially suited for use as anti-tumour vaccination.

The warhead of SG100 enables an autoimmune response:

24 mice (6/group) were immunized s.c. 2× with 35 µg in 150 µl ScFV-1-coil or with warhead (ScFV-1-coil-M362) either formulated on Alum or diluted in PBS. Immunizations were done on d0, and d14, sera were taken on d0 (before immunization) and d28 and analyzed for IgG1 and IgG2a against ScFV-1-coil (indicated as ScFV) and mAb IV.3 by standard ELISA. See FIG. 6.

As can be seen in FIG. 6, immunization with warhead induced a strong IgG1 and IgG2a response to ScFV-1-coil as well as to mAb IV.3 on day 28. A positive response was seen independent of the presence of Alum. Immunization with ScFV-1-coil only induced an IgG1 response against ScFV-1-coil and only in the presence of Alum, no IgG2a response was induced. These data fit with the concept that CpG (M362) induces a Th1 type response (IgG2a) and Alum induces a TH2 type response (IgG1). The response against ScFV-1-coil indicates that this protein is immunogenic in the mouse, indeed both the StrepTagII (amino acid sequence "SAWSHPQFEK" (SEQ ID 76)) and the pepE (amino acid sequence "EVSALEKEVSALEKEVSALEKEVSALE-KEVSALEK" SEQ ID 77) were target of the IgG responses (data not shown). However ScFV-1-coil also contains "mouse-self-sequences" because the ScFV contains the VH and VL domains of the mouse mAb IV.3. Therefore, an immune response against IV.3 indicates the presence of autoimmune antibodies. Indeed, only the warhead with or without Alum was able to induce this type of immune response. Hence, the presence of M362 on the ScFV-1-coil is able to break the tolerance against the autoantigens VH and VL domain of the parent antibody. By combining an autoantigen e.g. a TAA, through high affinity interaction with pepE of the warhead, the warhead will be able to induce the necessary autoimmune response against the TAA. The complex of the warhead (ScFV-1-coil-M362) with the TAA forms a potent vaccine for the treatment of cancer with over expression of the TAA in the vaccine. Such a vaccine may be formulated with any adjuvants, e.g. on Alum.

Example 13

Using the Technology Platform in Oncology, Immunogen G17

Warhead based on ScFV-coil1 (IV.3)+ODNM362, and immunogen G17 from rhesus and cynomolgus monkey (G17RM). In the following pE is understood as pyroGlu.

Sequence of human immunogen little gastrin (G17H, 1$^{st}$ 13 AA, SEQ ID 86):
pEGPWLEEEE EAYG Sequence of rhesus and cynomolgus monkey immunogen little gastrin (G17RM, 1$^{st}$ 13 AA, SEQ ID 99):
pEGPWMEEEE AAYG Sequence of mouse immunogen little gastrin (G17M, 1$^{st}$ 13 AA, SEQ ID 100):
pERPRMEEEE EAYG differences to G17RM in bold
Final Product Immunogen G17RM_1-Coil and G17H_1-Coil:

G17RM_1-coil, SEQ ID 101:
pEGPWMEEEEAAYGGGSGG*KVSALKEKVSALKEKVSALKEKVSALKEKVS ALKE*

G17H_1-coil,
SEQ ID 102
pEGPWLEEEEAYGGGSGG*KVSALKEKVSALKEKVSALKEKVSALKEKVS ALKE*

In bold: a linker (can be any linker)
In italics: the pepK coil for interaction with warhead
Ready-to-Use (Final Product) TYG100_1RM and TYG100_1H Warhead as described above (based ScFV-coil1 IV.3) is mixed with G17RM_1-coil or G17H_1-coil in a ratio which indicates 100% of warhead is complexed with G17RM_1-coil or G17H_1-coil, without G17 free immunogen being present (molar ratio of ~1:1) and formulated on Alum. Thereby TYG100_1RM and TYG100_1H are produced.

Example 14

TYG100_1RM for Treatment of Gastrin Dependent Cancer e.g. Pancreatic Cancer

6 Balb/c Mice were immunized 3 times on day 0, day 14 and day 35 with TYG100_1RM or G17_1RM (without warhead) containing rhesus monkey G17 (58.4 µg/shot in 0.5 ml). Two weeks after last immunization, serum was taken and analyzed for the presence of IgG antibodies against G17RM, G17H and G17M (=G17 from the mouse)

TABLE 2

| Mouse nr | IgG titre against warhead (ScFV-coil1) | IgG titre against G17RM | IgG titre against G17H | IgG titre against G17M |
|---|---|---|---|---|
| 1 | 2.5 * 10$^{-7}$ | 2.1 * 10$^{-6}$ | 1.2 * 10$^{-6}$ | 3.5 * 10$^{-3}$ |
| 2 | 2.1 * 10$^{-7}$ | 4.7 * 10$^{-5}$ | 1.4 * 10$^{-4}$ | 5 6 * 10$^{-3}$ |
| 3 | 1.2 * 10$^{-7}$ | 8.9 * 10$^{-7}$ | 2.1 * 10$^{-6}$ | 1 * 10$^{-2}$ |
| 4 | 1.1 * 10$^{-6}$ | 1.6 * 10$^{-5}$ | 1.7 * 10$^{-5}$ | 1 * 10$^{-2}$ |
| 5 | 2.0 * 10$^{-7}$ | 9.7 * 10$^{-6}$ | 9.8 * 10$^{-6}$ | nd |
| 6 | 5.8 * 10$^{-7}$ | 4.7 * 10$^{-6}$ | 6.5 * 10$^{-6}$ | 3.7 * 10$^{-3}$ |
| average | 4.1 * 10$^{-7}$ | 1.3 * 10$^{-5}$ | 2.9 * 10$^{-5}$ | 6.6 * 10$^{-3}$ |

Table 2 shows that all mice responded with IgG against the 2 components of the vaccine (warhead and G17RM). Importantly all mice produced IgG that cross reacted with human G17 and to a lesser extend with mouse G17 (G17M). The latter is remarkable because the first 13 immuno acids of mouse G17 (pERPRMEEEEEAYG, SEQ ID 86) are different in 3 AA from G17RM (differences indicated as bold and underlined) and G17M is an autoantigen for the mouse. The antibodies recognizing G17M are therefore autoantibodies, indicating that TYG100_1RM has been able to break the natural tolerance against the auto-antigen G17M. There was no response against G17 when the G17-peptide was immunized without the warhead.

The capacity of a vaccine to induce an autoimmune response is a prerequisite for an anti-cancer vaccine, where all tumour associated antigens (TAA) are auto-antigens which are over expressed, e.g. overexpressed on tumour cells. Hence a vaccine composed of the warhead of TYG100_1RM combined with human G17 as immunogen can be used as vaccine for the treatment of gastrin dependent tumours such as pancreatic cancer.

Example 15

Exemplary Products Including a Dimer of the Peptide Immungen

Final Product Immunogen G17RM_2-Coil and G17H_2-Coil

A dimer of G17RM (1st 13 AA of little gastrin) was chemically synthesized using a special flexible linker connecting the 2 peptides to one pepK coil G17RM_2-coil: (SEQ ID 103: Part of an immunogenic composition of the invention, comprising two rhesus monkey gastrin peptides of SEQ ID 99, a branched linker sequence and a peptide alpha-helix (TYG100_2RM). This part may be linked to the suitable directed adjuvant by a coiled-coil linkage)

immuno acids of rhesus monkey G17 (66.8 µg/shot in 0.5 ml). Two weeks after last immunization, serum was taken and analyzed for the presence of IgG antibodies against G17RM, G17H and G17M (=G17 from the mouse)

TABLE 3

| Mouse nr | IgG titre against warhead (ScFV-coil1) | IgG titre against G17RM | IgG titre against G17H | IgG titre against G17M |
|---|---|---|---|---|
| 1 | $1 * 10^{-7}$ | $1.8 * 10^{-7}$ | $2.2 * 10^{-6}$ | $4.3 * 10^{-3}$ |
| 2 | $2.8 * 10^{-7}$ | $1.1 * 10^{-6}$ | $15.6 * 10^{-6}$ | $2.9 * 10^{-3}$ |
| 3 | $8.9 * 10^{-7}$ | $8.4 * 10^{-7}$ | $2.4 * 10^{-6}$ | $4.4 * 10^{-3}$ |
| 4 | $5.9 * 10^{-7}$ | $9.2 * 10^{-7}$ | $1.2 * 10^{-5}$ | $2.2 * 10^{-3}$ |
| 5 | $1.7 * 10^{-7}$ | $8.0 * 10^{-7}$ | $1 * 10^{-5}$ | $7.6 * 10^{-3}$ |
| 6 | $1.1 * 10^{-7}$ | $6.1 * 10^{-7}$ | $2.5 * 10^{-5}$ | $7.4 * 10^{-3}$ |
| average | $3.5 * 10^{-7}$ | $1.6 * 10^{-6}$ | $3.5 * 10^{-5}$ | $4.8 * 10^{-3}$ |

Table 3 shows that all mice responded with IgG against the 2 components of the vaccine (warhead and G17RM). Importantly all mice produced IgG that cross reacted with human G17 and to a lesser extend with mouse G17 (G17M). The latter is remarkable because the first 13 immuno acids of mouse G17 (pERPRMEEEEEAYG, SEQ ID 86) is different in 3 AA from G17RM (differences indicated as bold and underlined) and G17M is an auto antigen for the mouse.

in bold a special flexible linker (can be any linker that connects three peptides) In italics the pepK coil for interaction with warhead G17H_2-coil: (SEQ ID 88: Part of an immunogenic composition of the invention, comprising two human gastrin peptides of SEQ ID 86, a branched linker sequence and a peptide alpha-helix (TYG100_2H). This part may be linked to the suitable directed adjuvant by a coiled-coil linkage)

The antibodies recognizing G17M are therefore autoantibodies, indicating that TYG100_2RM has been able to break the natural tolerance against the auto-antigen G17M. There was no response against G17 when the G17 peptide was immunized without the warhead.

The capacity of a vaccine to induce an autoimmune response is a prerequisite for an anti-cancer vaccine, where all tumour associated antigens (TAA) are auto-antigens

in bold a special flexible linker (can be any linker that connects three peptides)

In italics the pepK coil for interaction with warhead

Final Product TYG100_2RM and TYG100_2H

Warhead as described above (based on ScFV-coil1; IV.3) is mixed with G17RM_2-coil or G17H_2-coil in a ratio which indicates 100% of warhead is complexed with G17RM_2-coil or G17H_2-coil immunogen, without G17 free immunogen being present (molar ratio of ~1:1) and formulated on Alum. Thereby TYG100_2RM and TYG100_2H are produced.

Example 16

TYG100_2RM for Treatment of Gastrin Dependent Cancer e.g. Pancreatic Cancer

6 Balb/c Mice were immunized 3 times on day 0, day 14 and day 35 with TYG100_2RM containing the first 13 which are over expressed on tumour cells. Hence a vaccine composed of the warhead of TYG100_2RM combined with human G17 as immunogen can be used as vaccine for the treatment of gastrin dependent tumours such as pancreatic cancer. The responses against all 3 types of G17 induced by TYG100_2RM were stronger than those induced by TYG100_1RM (table 2), indicating that the dimer is preferred in the vaccine.

Example 17

TYG100_2RM for Treatment of Gastrin Dependent Cancer e.g. Pancreatic Cancer

6 Cynomolgus monkeys were immunized with TYG100_2RM and 6 were immunized with G17RM_2-coil on d0, d14 and d28. On d0, d14, d28, 42 and d56 serum was analyzed for the presence of IgG antibodies against autologous little gastrin (G17RM), little gastrin from humans (G17H), an irrelevant control peptide of similar MW as gastrin (control peptide) or against warhead (ScFV-coil1) using the multiplex ELISA system of Meso Scale Discovery (MSD) according to the MSD manual. In FIG. 10, it can be seen that all 6 animals showed a strong time dependent IgG response to warhead (ScFV-coil1) as well as to G17RM and G17H, no response was seen against the control peptide. The response against G17RM after three immunizations was 75% of the response against ScFV-coil1. This is remarkable since G17RM is a 100% autologous protein of only ~1.2 kDa whereas ScFV-coil1 is a 100% allogeneic protein of >30 kDa. The anti G17RM antibodies cross reacted strongly with G17H. There was no response against G17RM when the G17RM_2-coil peptide was used without the warhead. The decrease in IgG titre between d42 and 56 was stronger for G17RM than it was for ScFV, indicating that part of the IgG antibodies were neutralized by endogenous G17. Importantly, the presence of endogenous G17 did not boost the response to G17RM.

The data in FIG. 10 show that the vaccine was able to induce a bonavide autoantibody response which is reversible. This is a prerequisite for anti-cancer vaccines, since tumour associated antigens (TAA) are auto-antigens which are over-expressed, e.g. overexpressed on tumour cells but also present at lower expression levels on normal healthy cells. Hence a vaccine such as TYG100_2RM or TYG100_2H can be used for the treatment of gastrin dependent tumours such as pancreatic cancer. Once the cancer has completely been cured, treatment may be stopped and the induced anti G17 antibodies will be cleared from the circulation. In order to maintain a steady state (during treatment) the autoimmune response needs to be boosted by repeated injections with the vaccine. No irreversible autoimmune disease is induced with this type vaccine.

Example 18

TYG100_2RM for Treatment of Obesity

The animals from, Example 17 were monitored for their appetite and body weight was measured on d0, d14, d28, d42, and d56. After two injections with TYG100-2RM, 4 out of 6 animals lost interest in their daily snacks (biscuits), whereas basic food intake remained normal. This was accompanied by significant weight loss (FIG. 11). but no unwanted side effects were documented. So far such observations were never made with other vaccination with vaccines that were based on warhead and coiled coil interactions such as targeting immunogens other than gastrin immunogens (data not shown).

These data indicate that TYG100_2RM reduces craving for snacks (in between food) without influencing basic food intake needed for a healthy life. The animals were normally active and happy. Therefore, TYG100_2RM may be used for treatment of obesity.

REFERENCE LIST

1. Mathis, D. and C. Benoist. 2004. Back to central tolerance. *Immunity* 20:509-516.
2. Miller, J. F. A. P. and G. Morahan. 1992. Peripheral T cell tolerance. *Annu. Rev. Immunol.* 10:51-69.
3. Tafuri, A., J. Alferink, P. Möller, G. J. Hammerling, and B. Arnold. 1995. T cell awareness of paternal alloantigens during pregnancy. *Science* 270:630-633.
4. Cheever, M. A. and C. S. Higano. 2011. PROVENGE (Sipuleucel-T) in prostate cancer: the first FDA-approved therapeutic cancer vaccine. *Clin. Cancer Res.* 17:3520-3526.
5. Linley, A. J., M. Ahmad, and R. C. Rees. 2011. Tumour-associated antigens: considerations for their use in tumour immunotherapy. *Int. J. Hematol.* 93:263-273.
6. Brett, B. T., S. C. Smith, C. V. Bouvier, D. Michaeli, D. Hochhauser, B. R. Davidson, T. R. Kurzawinski, A. F. Watkinson, S. N. Van, R. E. Pounder, and M. E. Caplin. 2002. Phase II study of anti-gastrin-17 antibodies, raised to G17DT, in advanced pancreatic cancer. *J Clin Oncol* 20:4225-4231.
7. Rengifo-Cam, W. and P. Singh. 2004. Role of progastrins and gastrins and their receptors in GI and pancreatic cancers: targets for treatment. *Curr. Pharm. Des* 10:2345-2358.
8. Watson, S. A., D. Michaeli, T. M. Morris, P. Clarke, A. Varro, N. Griffin, A. Smith, T. Justin, and J. D. Hardcastle. 1999. Antibodies raised by gastrimmune inhibit the spontaneous metastasis of a human colorectal tumour, AP5LV. *Eur J Cancer* 35:1286-1291.
9. Watson, S. A., T. M. Morris, D. F. McWilliams, J. Harris, S. Evans, A. Smith, and P. A. Clarke. 2002. Potential role of endocrine gastrin in the colonic adenoma carcinoma sequence. *Br. J. Cancer* 87:567-573.
10. Morton, M., G. C. Prendergast, and T. D. Barrett. 2011. Targeting gastrin for the treatment of gastric acid related disorders and pancreatic cancer. *Trends in pharmacological sciences* 32:201-205.
11. Ciccotosto, G. D., J. K. Dawborn, K. J. Hardy, and A. Shulkes. 1996. Gastrin processing and secretion in patients with end-stage renal failure. *J Clin Endocrinol. Metab* 81:3231-3238.
12. Eaton-Bassiri, A., S. B. Dillon, M. Cunningham, M. A. Rycyzyn, J. Mills, R. T. Sarisky, and M. L. Mbow. 2004. Toll-like receptor 9 can be expressed at the cell surface of distinct populations of tonsils and human peripheral blood mononuclear cells. *Infect. Immun.* 72:7202-7211.
13. Saikh, K. U., T. L. Kissner, A. Sultana, G. Ruthel, and R. G. Ulrich. 2004. Human monocytes infected with *Yersinia pestis* express cell surface TLR9 and differentiate into dendritic cells. *J. Immunol.* 173:7426-7434.
14. Tanaka, J., K. Sugimoto, K. Shiraki, M. Tameda, S. Kusagawa, K. Nojiri, T. Beppu, K. Yoneda, N. Yamamoto, K. Uchida, T. Kojima, and Y. Takei. 2010. Functional cell surface expression of toll-like receptor 9 promotes cell proliferation and survival in human hepatocellular carcinomas. *Int. J Oncol.* 37:805-814.
15. Hartmann, G., J. Battiany, H. Poeck, M. Wagner, M. Kerkmann, N. Lubenow, S. Rothenfusser, and S. Endres. 2003. Rational design of new CpG oligonucleotides that combine B cell activation with high IFN-α induction in plasmacytoid dendritic cells. *Eur. J. Immunol.* 33:1633-1641.
16. Tversky, J. R., A. P. Bieneman, K. L. Chichester, R. G. Hamilton, and J. T. Schroeder. 2010. Subcutaneous allergen immunotherapy restores human dendritic cell innate immune function. *Clin. Exp. Allergy.* 40:94-102.
17. Hartmann, G., J. Battiany, H. Poeck, M. Wagner, M. Kerkmann, N. Lubenow, S. Rothenfusser, and S. Endres. 2003. Rational design of new CpG oligonucleotides that combine B cell activation with high IFN-α induction in plasmacytoid dendritic cells. *Eur. J. Immunol.* 33:1633-1641.
18. Abel, K., Y. Wang, L. Fritts, E. Sanchez, E. Chung, P. Fitzgerald-Bocarsly, A. M. Krieg, and C. J. Miller. 2005.

Deoxycytidyl-deoxyguanosine oligonucleotide classes A, B, and C induce distinct cytokine gene expression patterns in rhesus monkey peripheral blood mononuclear cells and distinct alpha interferon responses in TLR9-expressing rhesus monkey plasmacytoid dendritic cells. *Clin Diagn. Lab Immunol* 12:606-621.
19. Puig, M., K. W. Tosh, L. M. Schramm, L. T. Grajkowska, K. D. Kirschman, C. Tami, J. Beren, R. L. Rabin, and D. Verthelyi. 2012. TLR9 and TLR7 agonists mediate distinct type I IFN responses in humans and nonhuman primates in vitro and in vivo. *J Leukoc. Biol.* 91:147-158.
20. Hartmann, G., J. Battiany, H. Poeck, M. Wagner, M. Kerkmann, N. Lubenow, S. Rothenfusser, and S. Endres. 2003. Rational design of new CpG oligonucleotides that combine B cell activation with high IFN-α induction in plasmacytoid dendritic cells. *Eur. J. Immunol.* 33:1633-1641.
21. Hartmann, G., J. Battiany, H. Poeck, M. Wagner, M. Kerkmann, N. Lubenow, S. Rothenfusser, and S. Endres. 2003. Rational design of new CpG oligonucleotides that combine B cell activation with high IFN-α induction in plasmacytoid dendritic cells. *Eur. J. Immunol.* 33:1633-1641.
22. Arndt, K. M., K. M. Muller, and A. Pluckthun. 2001. Helix-stabilized Fv (hsFv) antibody fragments: substituting the constant domains of a Fab fragment for a heterodimeric coiled-coil domain. *J Mol. Biol.* 312:221-228.
23. Puig, M., K. W. Tosh, L. M. Schramm, L. T. Grajkowska, K. D. Kirschman, C. Tami, J. Beren, R. L. Rabin, and D. Verthelyi. 2012. TLR9 and TLR7 agonists mediate distinct type I IFN responses in humans and nonhuman primates in vitro and in vivo. *J Leukoc. Biol.* 91:147-158.
24. Puig, M., K. W. Tosh, L. M. Schramm, L. T. Grajkowska, K. D. Kirschman, C. Tami, J. Beren, R. L. Rabin, and D. Verthelyi. 2012. TLR9 and TLR7 agonists mediate distinct type I IFN responses in humans and nonhuman primates in vitro and in vivo. *J Leukoc. Biol.* 91:147-158.
25. Puig, M., K. W. Tosh, L. M. Schramm, L. T. Grajkowska, K. D. Kirschman, C. Tami, J. Beren, R. L. Rabin, and D. Verthelyi. 2012. TLR9 and TLR7 agonists mediate distinct type I IFN responses in humans and nonhuman primates in vitro and in vivo. *J Leukoc. Biol.* 91:147-158.
26. Abel, K., Y. Wang, L. Fritts, E. Sanchez, E. Chung, P. Fitzgerald-Bocarsly, A. M. Krieg, and C. J. Miller. 2005. Deoxycytidyl-deoxyguanosine oligonucleotide classes A, B, and C induce distinct cytokine gene expression patterns in rhesus monkey peripheral blood mononuclear cells and distinct alpha interferon responses in TLR9-expressing rhesus monkey plasmacytoid dendritic cells. *Clin Diagn. Lab Immunol* 12:606-621.
27. Lund, J., A. Sato, S. Akira, R. Medzhitov, and A. Iwasaki. 2003. Toll-like receptor 9-mediated recognition of herpes simplex virus-2 by plasmacytoid dendritic cells. *J. Exp. Med.* 198:513-520.
28. Plitas, G., B. M. Burt, H. M. Nguyen, Z. M. Bamboat, and R. P. Dematteo. 2008. Toll-like receptor 9 inhibition reduces mortality in polymicrobial sepsis. *J. Exp. Med.* 205:1277-1283.
29. Ashman, R. F., J. A. Goeken, E. Latz, and P. Lenert. 2011. Optimal oligonucleotide sequences for TLR9 inhibitory activity in human cells: lack of correlation with TLR9 binding. *Int. Immunol.* 23:203-214.
30. Tel, J., N. Beenhakker, G. Koopman, B. Hart, G. C. Mudde, and V. de, I. 2012. Targeted delivery of CpG ODN to CD32 on human and monkey plasmacytoid dendritic cells augments IFNalpha secretion. *Immunobiology.* 217:1017-1024.
31. Van Reijsen, F. C., C. A. F. M. Bruijnzeel-Koomen, F. S. Kalthoff, E. Maggi, S. Romagnani, J. K. T. Westland, and G. C. Mudde. 1992. Skin-derived aeroallergen-specific T-cell clones of Th2 phenotype in patients with atopic dermatitis. *J. Allergy Clin. Immunol.* 90:184-193.
32. Litowski, J. R. and R. S. Hodges. 2002. Designing heterodimeric two-stranded alpha-helical coiled-coils. Effects of hydrophobicity and alpha-helical propensity on protein folding, stability, and specificity. *J. Biol. Chem.* 277:37272-37279.
33. Chao, H., D. L. Bautista, J. Litowski, R. T. Irvin, and R. S. Hodges. 1998. Use of a heterodimeric coiled-coil system for biosensor application and affinity purification. *J. Chromatogr. B Biomed. Sci. Appl.* 715:307-329.
34. Litowski, J. R. and R. S. Hodges. 2002. Designing heterodimeric two-stranded alpha-helical coiled-coils. Effects of hydrophobicity and alpha-helical propensity on protein folding, stability, and specificity. *J. Biol. Chem.* 277:37272-37279.
35. Greenman, J., A. L. Tutt, A. J. George, K. A. Pulford, G. T. Stevenson, and M. J. Glennie. 1991. Characterization of a new monoclonal anti-Fc gamma RII antibody, AT10, and its incorporation into a bispecific F(ab')2 derivative for recruitment of cytotoxic effectors. *Mol. Immunol* 28:1243-1254.
36. Looney, R. J., G. N. Abraham, and C. L. Anderson. 1986. Human monocytes and U937 cells bear two distinct Fc receptors for IgG. *J Immunol.* 136:1641-1647.
37. Macintyre, E. A., P. J. Roberts, R. bdul-Gaffar, K. O'Flynn, G. R. Pilkington, F. Farace, J. Morgan, and D. C. Linch. 1988. Mechanism of human monocyte activation via the 40-kDa Fc receptor for IgG. *J Immunol.* 141:4333-4343.
38. Krug, A., S. Rothenfusser, V. Hornung, B. Jahrsdorfer, S. Blackwell, Z. K. Ballas, S. Endres, A. M. Krieg, and G. Hartmann. 2001. Identification of CpG oligonucleotide sequences with high induction of IFN-alpha/beta in plasmacytoid dendritic cells. *Eur J Immunol.* 31:2154-2163.
39. Krieg, A. M., A. K. Yi, S. Matson, T. J. Waldschmidt, G. A. Bishop, R. Teasdale, G. A. Koretzky, and D. M. Klinman. 1995. CpG motifs in bacterial DNA trigger direct B-cell activation. *Nature.* 374:546-549.
40. Hartmann, G., J. Battiany, H. Poeck, M. Wagner, M. Kerkmann, N. Lubenow, S. Rothenfusser, and S. Endres. 2003. Rational design of new CpG oligonucleotides that combine B cell activation with high IFN-alpha induction in plasmacytoid dendritic cells. *Eur J Immunol.* 33:1633-1641.
41. Tel, J., N. Beenhakker, G. Koopman, B. Hart, G. C. Mudde, and V. de, I. 2012. Targeted delivery of CpG ODN to CD32 on human and monkey plasmacytoid dendritic cells augments IFNalpha secretion. *Immunobiology.* 217:1017-1024.
42. Chao, H., D. L. Bautista, J. Litowski, R. T. Irvin, and R. S. Hodges. 1998. Use of a heterodimeric coiled-coil system for biosensor application and affinity purification. *J. Chromatogr. B Biomed. Sci. Appl.* 715:307-329.
43. Litowski, J. R. and R. S. Hodges. 2001. Designing heterodimeric two-stranded alpha-helical coiled-coils: the effect of chain length on protein folding, stability and specificity. *J. Pept. Res.* 58:477-492.
44. Litowski, J. R. and R. S. Hodges. 2002. Designing heterodimeric two-stranded alpha-helical coiled-coils. Effects of hydrophobicity and alpha-helical propensity on protein folding, stability, and specificity. *J. Biol. Chem.* 277:37272-37279.

45. Berntzen, G., J. T. Andersen, K. Ustgard, T. E. Michaelsen, S. A. Mousavi, J. D. Qian, P. E. Kristiansen, V. Lauvrak, and I. Sandlie. 2009. Identification of a high affinity Fcgamma RIIA binding peptide that distinguishes Fcgamma RIIA from Fcgamma RIIB and exploits Fcgamma RIIA mediated phagocytosis and degradation. *J. Biol. Chem.* 284:1126-1135.
46. Chao, H., D. L. Bautista, J. Litowski, R. T. Irvin, and R. S. Hodges. 1998. Use of a heterodimeric coiled-coil system for biosensor application and affinity purification. *J. Chromatogr. B Biomed. Sci. Appl.* 715:307-329.
47. Litowski, J. R. and R. S. Hodges. 2001. Designing heterodimeric two-stranded alpha-helical coiled-coils: the effect of chain length on protein folding, stability and specificity. *J. Pept. Res.* 58:477-492.
48. Litowski, J. R. and R. S. Hodges. 2002. Designing heterodimeric two-stranded alpha-helical coiled-coils. Effects of hydrophobicity and alpha-helical propensity on protein folding, stability, and specificity. *J. Biol. Chem.* 277:37272-37279.
49. Chao, H., D. L. Bautista, J. Litowski, R. T. Irvin, and R. S. Hodges. 1998. Use of a heterodimeric coiled-coil system for biosensor application and affinity purification. *J. Chromatogr. B Biomed. Sci. Appl.* 715:307-329.
50. Litowski, J. R. and R. S. Hodges. 2001. Designing heterodimeric two-stranded alpha-helical coiled-coils: the effect of chain length on protein folding, stability and specificity. *J. Pept. Res.* 58:477-492.
51. Litowski, J. R. and R. S. Hodges. 2002. Designing heterodimeric two-stranded alpha-helical coiled-coils. Effects of hydrophobicity and alpha-helical propensity on protein folding, stability, and specificity. *J. Biol. Chem.* 277:37272-37279.
52. Chao, H., D. L. Bautista, J. Litowski, R. T. Irvin, and R. S. Hodges. 1998. Use of a heterodimeric coiled-coil system for biosensor application and affinity purification. *J. Chromatogr. B Biomed. Sci. Appl.* 715:307-329.
53. Litowski, J. R. and R. S. Hodges. 2001. Designing heterodimeric two-stranded alpha-helical coiled-coils: the effect of chain length on protein folding, stability and specificity. *J. Pept. Res.* 58:477-492.
54. Litowski, J. R. and R. S. Hodges. 2002. Designing heterodimeric two-stranded alpha-helical coiled-coils. Effects of hydrophobicity and alpha-helical propensity on protein folding, stability, and specificity. *J. Biol. Chem.* 277:37272-37279.
55. Chao, H., D. L. Bautista, J. Litowski, R. T. Irvin, and R. S. Hodges. 1998. Use of a heterodimeric coiled-coil system for biosensor application and affinity purification. *J. Chromatogr. B Biomed. Sci. Appl.* 715:307-329.
56. Litowski, J. R. and R. S. Hodges. 2001. Designing heterodimeric two-stranded alpha-helical coiled-coils: the effect of chain length on protein folding, stability and specificity. *J. Pept. Res.* 58:477-492.
57. Litowski, J. R. and R. S. Hodges. 2002. Designing heterodimeric two-stranded alpha-helical coiled-coils. Effects of hydrophobicity and alpha-helical propensity on protein folding, stability, and specificity. *J. Biol. Chem.* 277:37272-37279.
58. Sallusto, F. and A. Lanzavecchia. 1994. Efficient presentation of soluble antigen by cultured human dendritic cells is maintained by granulocyte/macrophage colony-stimulating factor plus interleukin 4 and downregulated by tumor necrosis factor α. *J. Exp. Med.* 179:1109-1118.
59. Mudde, G. C., F. C. Van Reijsen, G. J. Boland, G. C. De Gast, P. L. B. Bruijnzeel, and C. A. F. M. Bruijnzeel-Koomen. 1990. Allergen presentation by epidermal Langerhans' cells from patients with atopic dermatitis is mediated by IgE. *Immunology* 69:335-341.
60. Santamaria, L. F., R. Bheekha, F. C. Van Reijsen, M. T. Perez Soler, M. Suter, C. A. F. M. Bruijnzeel-Koomen, and G. C. Mudde. 1993. Antigen focusing by specific monomeric immunoglobulin E bound to CD23 on Epstein-Barr virus-transformed B cells. *Hum. Immunol.* 37:23-30.
61. Mudde, G. C., I. G. Reischl, N. Corvaïa, A. Hren, and E.-M. Pöllabauer. 1996. Antigen presentation in allergic sensitization. *Immunol. Cell Biol.* 74:167-173.
62. Maurer, D., C. Ebner, B. Reininger, E. Fiebiger, D. Kraft, J.-P. Kinet, and G. Stingl. 1995. The high affinity IgE receptor (FcεRI) mediates IgE-dependent allergen presentation. *J. Immunol.* 154:6285-6290.

The invention claimed is:

1. An immunogenic preparation for eliciting an immune response to an antigen, comprising:
   a first part comprising at least an anti-CD32 binding moiety linked to a TLR9 binding ligand and a first peptidic alpha-helix, wherein the anti-CD32 binding moiety is an antibody or an antibody fragment and the TLR9 binding ligand is a CpG oligodeoxynucleotide; and
   a second part comprising the antigen and a second peptidic alpha-helix coiled to the first alpha-helix, thereby obtaining a coiled coil, wherein the coiled coil is a heterocoil of two different matching helices, each of the matching helices comprising at least 3 coils and comprising a sequence selected from the group consisting of SEQ ID NOs:91-98.

2. The immunogenic preparation of claim 1, wherein each of said first and second alpha-helices comprises 3-5 amino acid repeats of an amino acid motif, specifically binding to each other with a Kd of less than $10^{-6}$ M.

3. The immunogenic preparation of claim 1, wherein said antigen is selected from the group consisting of:
   a tumor associated antigen;
   an antigen of a pathogen; and
   an allergen.

4. The immunogenic preparation of claim 1, wherein said anti-CD32 binding moiety is targeting CD32a.

5. The immunogenic preparation of claim 1, wherein said antigen is part of an allergen, and wherein said anti-CD32 binding moiety is targeting CD32a and CD32b.

6. The immunogenic preparation of claim 1, wherein said antigen is selected from the group consisting of:
   an antigen which is part of an allergen, and
   a human autoantigen.

7. The immunogenic preparation of claim 6, wherein said anti-CD32 binding moiety is targeting CD32b, or CD32a and CD32b.

8. The immunogenic preparation of claim 6, wherein said anti-CD32 binding moiety is targeting CD32a and CD32b.

9. The immunogenic preparation of claim 6, wherein the preparation comprises:
   a directed adjuvant that is composed of the anti-CD32 binding moiety linked to the first alpha-helix comprising the sequence of SEQ ID NO:70, which is coupled to the TLR9 binding ligand of SEQ ID NO:69; and
   an antigen that comprises or consists of a protein having an amino acid sequence according to SEQ ID NO:30 linked to the second alpha-helix;
   wherein the directed adjuvant and the antigen are bound to each other by the coiled-coil structure of the first and second alpha-helices.

10. The immunogenic preparation of claim 9, wherein the anti-CD32 binding moiety linked to the first alpha-helix is present in a ratio of 1:1-18 (molecule per molecule) compared to the TLR9 binding ligand.

11. The immunogenic preparation of claim 9, wherein the antigen that comprises a protein having an amino acid sequence according to SEQ ID NO:30 is a variant wherein Cys379 is removed from the protein according to SEQ ID NO:30.

12. The immunogenic preparation of claim 1, wherein the antigen is a hormone selected from the group consisting of gastrin, secretin, insulin, a thyroid hormone, and a sexual hormone.

13. The immunogenic preparation of claim 3, wherein the tumor associated antigen is selected from the group consisting of Her2/neu, interferon alpha (INFα), epidermal growth factor (EGF), EGF receptor (EGF-R), epithelial cell adhesion molecule (EpCAM), alphafetoprotein (AFP), carcinoembryonic antigen (CEA), MUC-1 and LewisY.

* * * * *

SEQUENCE LISTING

```
<160> NUMBER OF SEQ ID NOS: 128

<210> SEQ ID NO 1
<211> LENGTH: 35
<212> TYPE: PRT
<213> ORGANISM: artificial sequence
<220> FEATURE:
<223> OTHER INFORMATION: Peptide

<400> SEQUENCE: 1

Glu Val Ser Ala Leu Glu Lys Glu Val Ser Ala Leu Glu Lys Glu Val
1               5                   10                  15

Ser Ala Leu Glu Lys Glu Val Ser Ala Leu Glu Lys Glu Val Ser Ala
            20                  25                  30

Leu Glu Lys
        35

<210> SEQ ID NO 2
<211> LENGTH: 35
<212> TYPE: PRT
<213> ORGANISM: artificial sequence
<220> FEATURE:
```

<223> OTHER INFORMATION: Peptide

<400> SEQUENCE: 2

Lys Val Ser Ala Leu Lys Glu Lys Val Ser Ala Leu Lys Glu Lys Val
1               5                   10                  15
Ser Ala Leu Lys Glu Lys Val Ser Ala Leu Lys Glu Lys Val Ser Ala
            20                  25                  30
Leu Lys Glu
        35

<210> SEQ ID NO 3
<211> LENGTH: 21
<212> TYPE: PRT
<213> ORGANISM: artificial sequence
<220> FEATURE:
<223> OTHER INFORMATION: Peptide

<400> SEQUENCE: 3

Glu Ile Ala Ala Leu Glu Lys Glu Ile Ala Ala Leu Glu Lys Glu Ile
1               5                   10                  15
Ala Ala Leu Glu Lys
            20

<210> SEQ ID NO 4
<211> LENGTH: 28
<212> TYPE: PRT
<213> ORGANISM: artificial sequence
<220> FEATURE:
<223> OTHER INFORMATION: Peptide

<400> SEQUENCE: 4

Glu Ile Ala Ala Leu Glu Lys Glu Ile Ala Ala Leu Glu Lys Glu Ile
1               5                   10                  15
Ala Ala Leu Glu Lys Glu Ile Ala Ala Leu Glu Lys
            20                  25

<210> SEQ ID NO 5
<211> LENGTH: 21
<212> TYPE: PRT
<213> ORGANISM: artificial sequence
<220> FEATURE:
<223> OTHER INFORMATION: Peptide

<400> SEQUENCE: 5

Lys Ile Ala Ala Leu Lys Glu Lys Ile Ala Ala Leu Lys Glu Lys Ile
1               5                   10                  15
Ala Ala Leu Lys Glu
            20

<210> SEQ ID NO 6
<211> LENGTH: 28
<212> TYPE: PRT
<213> ORGANISM: artificial sequence
<220> FEATURE:
<223> OTHER INFORMATION: Peptide

<400> SEQUENCE: 6

Lys Ile Ala Ala Leu Lys Glu Lys Ile Ala Ala Leu Lys Glu Lys Ile
1               5                   10                  15
Ala Ala Leu Lys Glu Lys Ile Ala Ala Leu Lys Glu
            20                  25

<210> SEQ ID NO 7

```
<211> LENGTH: 21
<212> TYPE: PRT
<213> ORGANISM: artificial sequence
<220> FEATURE:
<223> OTHER INFORMATION: Peptide

<400> SEQUENCE: 7

Glu Ile Ser Ala Leu Glu Lys Glu Ile Ser Ala Leu Glu Lys Glu Ile
1               5                   10                  15

Ser Ala Leu Glu Lys
            20

<210> SEQ ID NO 8
<211> LENGTH: 28
<212> TYPE: PRT
<213> ORGANISM: artificial sequence
<220> FEATURE:
<223> OTHER INFORMATION: Peptide

<400> SEQUENCE: 8

Glu Ile Ser Ala Leu Glu Lys Glu Ile Ser Ala Leu Glu Lys Glu Ile
1               5                   10                  15

Ser Ala Leu Glu Lys Glu Ile Ser Ala Leu Glu Lys
            20                  25

<210> SEQ ID NO 9
<211> LENGTH: 21
<212> TYPE: PRT
<213> ORGANISM: artificial sequence
<220> FEATURE:
<223> OTHER INFORMATION: Peptide

<400> SEQUENCE: 9

Lys Ile Ser Ala Leu Lys Glu Lys Ile Ser Ala Leu Lys Glu Lys Ile
1               5                   10                  15

Ser Ala Leu Lys Glu
            20

<210> SEQ ID NO 10
<211> LENGTH: 28
<212> TYPE: PRT
<213> ORGANISM: artificial sequence
<220> FEATURE:
<223> OTHER INFORMATION: Peptide

<400> SEQUENCE: 10

Lys Ile Ser Ala Leu Lys Glu Lys Ile Ser Ala Leu Lys Glu Lys Ile
1               5                   10                  15

Ser Ala Leu Lys Glu Lys Ile Ser Ala Leu Lys Glu
            20                  25

<210> SEQ ID NO 11
<211> LENGTH: 21
<212> TYPE: PRT
<213> ORGANISM: artificial sequence
<220> FEATURE:
<223> OTHER INFORMATION: Peptide

<400> SEQUENCE: 11

Glu Val Ala Ala Leu Glu Lys Glu Val Ala Ala Leu Glu Lys Glu Val
1               5                   10                  15

Ala Ala Leu Glu Lys
            20
```

```
<210> SEQ ID NO 12
<211> LENGTH: 28
<212> TYPE: PRT
<213> ORGANISM: artificial sequence
<220> FEATURE:
<223> OTHER INFORMATION: Peptide

<400> SEQUENCE: 12

Glu Val Ala Ala Leu Glu Lys Glu Val Ala Ala Leu Glu Lys Glu Val
1               5                   10                  15
Ala Ala Leu Glu Lys Glu Val Ala Ala Leu Glu Lys
            20                  25

<210> SEQ ID NO 13
<211> LENGTH: 21
<212> TYPE: PRT
<213> ORGANISM: artificial sequence
<220> FEATURE:
<223> OTHER INFORMATION: Peptide

<400> SEQUENCE: 13

Lys Val Ala Ala Leu Lys Glu Lys Val Ala Ala Leu Lys Glu Lys Val
1               5                   10                  15
Ala Ala Leu Lys Glu
            20

<210> SEQ ID NO 14
<211> LENGTH: 28
<212> TYPE: PRT
<213> ORGANISM: artificial sequence
<220> FEATURE:
<223> OTHER INFORMATION: Peptide

<400> SEQUENCE: 14

Lys Val Ala Ala Leu Lys Glu Lys Val Ala Ala Leu Lys Glu Lys Val
1               5                   10                  15
Ala Ala Leu Lys Glu Lys Val Ala Ala Leu Lys Glu
            20                  25

<210> SEQ ID NO 15
<211> LENGTH: 21
<212> TYPE: PRT
<213> ORGANISM: artificial sequence
<220> FEATURE:
<223> OTHER INFORMATION: Peptide

<400> SEQUENCE: 15

Glu Val Ser Ala Leu Glu Lys Glu Val Ser Ala Leu Glu Lys Glu Val
1               5                   10                  15
Ser Ala Leu Glu Lys
            20

<210> SEQ ID NO 16
<211> LENGTH: 28
<212> TYPE: PRT
<213> ORGANISM: artificial sequence
<220> FEATURE:
<223> OTHER INFORMATION: Peptide

<400> SEQUENCE: 16

Glu Val Ser Ala Leu Glu Lys Glu Val Ser Ala Leu Glu Lys Glu Val
1               5                   10                  15
Ser Ala Leu Glu Lys Glu Val Ser Ala Leu Glu Lys
            20                  25
```

```
<210> SEQ ID NO 17
<211> LENGTH: 21
<212> TYPE: PRT
<213> ORGANISM: artificial sequence
<220> FEATURE:
<223> OTHER INFORMATION: Peptide

<400> SEQUENCE: 17

Lys Val Ser Ala Leu Lys Glu Lys Val Ser Ala Leu Lys Glu Lys Val
1               5                   10                  15

Ser Ala Leu Lys Glu
            20

<210> SEQ ID NO 18
<211> LENGTH: 28
<212> TYPE: PRT
<213> ORGANISM: artificial sequence
<220> FEATURE:
<223> OTHER INFORMATION: Peptide

<400> SEQUENCE: 18

Lys Val Ser Ala Leu Lys Glu Lys Val Ser Ala Leu Lys Glu Lys Val
1               5                   10                  15

Ser Ala Leu Lys Glu Lys Val Ser Ala Leu Lys Glu
            20                  25

<210> SEQ ID NO 19
<211> LENGTH: 297
<212> TYPE: PRT
<213> ORGANISM: artificial sequence
<220> FEATURE:
<223> OTHER INFORMATION: ScFV-coil

<400> SEQUENCE: 19

Glu Val Gln Leu Gln Gln Ser Gly Pro Glu Leu Lys Lys Pro Gly Glu
1               5                   10                  15

Thr Val Lys Ile Ser Cys Lys Ala Ser Gly Tyr Thr Phe Thr Asn Tyr
            20                  25                  30

Gly Met Asn Trp Val Lys Gln Ala Pro Gly Lys Gly Leu Lys Trp Met
        35                  40                  45

Gly Trp Leu Asn Thr Tyr Thr Gly Glu Ser Ile Tyr Pro Asp Asp Phe
    50                  55                  60

Lys Gly Arg Phe Ala Phe Ser Ser Glu Thr Ser Ala Ser Thr Ala Tyr
65                  70                  75                  80

Leu Gln Ile Asn Asn Leu Lys Asn Glu Asp Met Ala Thr Tyr Phe Cys
                85                  90                  95

Ala Arg Gly Asp Tyr Gly Tyr Asp Asp Pro Leu Asp Tyr Trp Gly Gln
            100                 105                 110

Gly Thr Ser Val Thr Val Ser Ser Gly Gly Gly Ser Gly Gly Gly
        115                 120                 125

Gly Ser Gly Gly Gly Ser Asp Ile Val Met Thr Gln Ala Ala Pro
    130                 135                 140

Ser Val Pro Val Thr Pro Gly Glu Ser Val Ser Ile Ser Cys Arg Ser
145                 150                 155                 160

Ser Lys Ser Leu Leu His Thr Asn Gly Asn Thr Tyr Leu His Trp Phe
                165                 170                 175

Leu Gln Arg Pro Gly Gln Ser Pro Gln Leu Leu Ile Tyr Arg Met Ser
            180                 185                 190

Val Leu Ala Ser Gly Val Pro Asp Arg Phe Ser Gly Ser Gly Ser Gly
```

```
                    195                 200                 205
Thr Ala Phe Thr Leu Ser Ile Ser Arg Val Glu Ala Glu Asp Val Gly
210                 215                 220

Val Phe Tyr Cys Met Gln His Leu Glu Tyr Pro Leu Thr Phe Gly Ala
225                 230                 235                 240

Gly Thr Lys Leu Glu Leu Lys Gly Ser Ile Ser Ala Trp Ser His Pro
                245                 250                 255

Gln Phe Glu Lys Gly Pro Glu Val Ser Ala Leu Glu Lys Glu Val Ser
                260                 265                 270

Ala Leu Glu Lys Glu Val Ser Ala Leu Glu Lys Glu Val Ser Ala Leu
                275                 280                 285

Glu Lys Glu Val Ser Ala Leu Glu Lys
290                 295

<210> SEQ ID NO 20
<211> LENGTH: 18
<212> TYPE: PRT
<213> ORGANISM: artificial sequence
<220> FEATURE:
<223> OTHER INFORMATION: Peptide

<400> SEQUENCE: 20

Ala Asp Gly Ala Trp Ala Trp Val Trp Leu Thr Glu Thr Ala Val Gly
1               5                   10                  15

Ala Ala

<210> SEQ ID NO 21
<211> LENGTH: 316
<212> TYPE: PRT
<213> ORGANISM: artificial sequence
<220> FEATURE:
<223> OTHER INFORMATION: ScFV-coil

<400> SEQUENCE: 21

Met Glu Leu Gly Leu Ser Trp Ile Phe Leu Leu Ala Ile Leu Lys Gly
1               5                   10                  15

Val Gln Cys Glu Val Gln Leu Gln Gln Ser Gly Pro Glu Leu Lys Lys
                20                  25                  30

Pro Gly Glu Thr Val Lys Ile Ser Cys Lys Ala Ser Gly Tyr Thr Phe
            35                  40                  45

Thr Asn Tyr Asn Trp Val Lys Gln Ala Pro Gly Lys Gly Leu Lys Trp
        50                  55                  60

Met Gly Trp Leu Asn Thr Tyr Thr Gly Glu Ser Ile Tyr Pro Asp Asp
65                  70                  75                  80

Phe Lys Gly Arg Phe Ala Phe Ser Ser Glu Thr Ser Ala Ser Thr Ala
                85                  90                  95

Tyr Leu Gln Ile Asn Asn Leu Lys Gly Met Asn Glu Asp Met Ala Thr
                100                 105                 110

Tyr Phe Cys Ala Arg Gly Asp Tyr Gly Tyr Asp Pro Leu Asp Tyr
                115                 120                 125

Trp Gly Gln Gly Thr Ser Val Thr Val Ser Ser Gly Gly Gly Gly Ser
            130                 135                 140

Gly Gly Gly Gly Ser Gly Gly Gly Gly Asp Ile Val Met Thr Gln
145                 150                 155                 160

Ala Ala Pro Ser Val Pro Val Thr Pro Gly Glu Ser Val Ser Ile Ser
                165                 170                 175

Cys Arg Ser Ser Lys Ser Leu Leu His Thr Asn Gly Asn Thr Tyr Leu
```

```
                180                 185                 190
His Trp Phe Leu Gln Arg Pro Gly Gln Ser Pro Gln Leu Leu Ile Tyr
        195                 200                 205

Arg Met Ser Val Leu Ala Ser Gly Val Pro Asp Arg Phe Ser Gly Ser
    210                 215                 220

Gly Ser Gly Thr Ala Phe Thr Leu Ser Ile Ser Arg Val Glu Ala Glu
225                 230                 235                 240

Asp Val Gly Val Phe Tyr Cys Met Gln His Leu Glu Tyr Pro Leu Thr
                245                 250                 255

Phe Gly Ala Gly Thr Lys Leu Glu Leu Lys Gly Ser Ile Ser Ala Trp
            260                 265                 270

Ser His Pro Gln Phe Glu Lys Gly Pro Glu Val Ser Ala Leu Glu Lys
        275                 280                 285

Glu Val Ser Ala Leu Glu Lys Glu Val Ser Ala Leu Glu Lys Glu Val
    290                 295                 300

Ser Ala Leu Glu Lys Glu Val Ser Ala Leu Glu Lys
305                 310                 315

<210> SEQ ID NO 22
<211> LENGTH: 68
<212> TYPE: PRT
<213> ORGANISM: artificial sequence
<220> FEATURE:
<223> OTHER INFORMATION: Peptide-coil

<400> SEQUENCE: 22

Ala Asp Gly Ala Trp Ala Trp Val Trp Leu Thr Glu Thr Ala Val Gly
1               5                   10                  15

Ala Ala Lys Gly Gly Gly Ser Trp Ser His Pro Gln Phe Glu Lys Gly
            20                  25                  30

Pro Glu Val Ser Ala Leu Glu Lys Glu Val Ser Ala Leu Glu Lys Glu
        35                  40                  45

Val Ser Ala Leu Glu Lys Glu Val Ser Ala Leu Glu Lys Glu Val Ser
    50                  55                  60

Ala Leu Glu Lys
65

<210> SEQ ID NO 23
<211> LENGTH: 254
<212> TYPE: PRT
<213> ORGANISM: artificial sequence
<220> FEATURE:
<223> OTHER INFORMATION: Immunogen-coil

<400> SEQUENCE: 23

His His His His His His Tyr Tyr Arg Tyr Val Ala Arg Glu Gln Ser
1               5                   10                  15

Cys Arg Arg Pro Asn Ala Gln Arg Phe Gly Ile Ser Asn Tyr Cys Gln
            20                  25                  30

Ile Tyr Pro Pro Asn Val Asn Lys Ile Arg Glu Ala Leu Ala Gln Thr
        35                  40                  45

His Ser Ala Ile Ala Val Asp Leu Arg Gln Met Arg Thr Val Thr Pro
    50                  55                  60

Ile Arg Met Gln Gly Gly Cys Gly Ser Cys Trp Ala Phe Ser Gly Val
65                  70                  75                  80

Ala Ala Thr Glu Ser Ala Tyr Leu Gln Gln Tyr Asp Ile Lys Tyr Thr
                85                  90                  95
```

Trp Asn Val Pro Lys Ile Ala Pro Lys Ser Glu Asn Val Val Thr
            100                 105                 110

Val Lys Val Met Gly Asp Asp Gly Val Leu Ala Cys Ala Ile Ala Thr
        115                 120                 125

His Ala Lys Ile Arg Asp Asp Ala Phe Arg His Tyr Asp Gly Arg Thr
    130                 135                 140

Ile Ile Gln Arg Asp Asn Gly Tyr Gln Pro Asn Tyr His Ala Val Asn
145                 150                 155                 160

Ile Val Gly Tyr Ser Asn Ala Gln Gly Val Asp Tyr Trp Ile Val Arg
                165                 170                 175

Asn Ser Trp Asp Thr Asn Trp His Glu Ile Lys Lys Val Leu Val Pro
            180                 185                 190

Gly Cys His Gly Ser Glu Pro Cys Ile Ile His Arg Gly Lys Pro Phe
        195                 200                 205

Gly Gly Gly Ser Gly Gly Ser Cys Gly Gly Lys Val Ser Ala Leu
    210                 215                 220

Lys Glu Lys Val Ser Ala Leu Lys Glu Lys Val Ser Ala Leu Lys Glu
225                 230                 235                 240

Lys Val Ser Ala Leu Lys Glu Lys Val Ser Ala Leu Lys Glu
                245                 250

<210> SEQ ID NO 24
<211> LENGTH: 48
<212> TYPE: PRT
<213> ORGANISM: artificial sequence
<220> FEATURE:
<223> OTHER INFORMATION: Peptide

<400> SEQUENCE: 24

Tyr Tyr Arg Tyr Val Ala Arg Glu Gln Ser Cys Arg Arg Pro Asn Ala
1               5                   10                  15

Gln Arg Phe Gly Ile Ser Asn Tyr Cys Gln Ile Tyr Pro Pro Asn Ala
            20                  25                  30

Asn Lys Ile Arg Glu Ala Leu Ala Gln Thr His Ser Ala Ile Ala Val
        35                  40                  45

<210> SEQ ID NO 25
<211> LENGTH: 34
<212> TYPE: PRT
<213> ORGANISM: artificial sequence
<220> FEATURE:
<223> OTHER INFORMATION: Peptide

<400> SEQUENCE: 25

Asp Leu Arg Gln Met Arg Thr Val Thr Pro Ile Arg Met Gln Gly Gly
1               5                   10                  15

Cys Gly Ser Cys Trp Ala Phe Ser Gly Val Ala Ala Thr Glu Ser Ala
            20                  25                  30

Tyr Leu

<210> SEQ ID NO 26
<211> LENGTH: 20
<212> TYPE: PRT
<213> ORGANISM: artificial sequence
<220> FEATURE:
<223> OTHER INFORMATION: Peptide

<400> SEQUENCE: 26

Gln Gln Tyr Asp Ile Lys Tyr Thr Trp Asn Val Pro Lys Ile Ala Pro
1               5                   10                  15

Lys Ser Glu Asn
            20

<210> SEQ ID NO 27
<211> LENGTH: 26
<212> TYPE: PRT
<213> ORGANISM: artificial sequence
<220> FEATURE:
<223> OTHER INFORMATION: Peptide

<400> SEQUENCE: 27

Val Val Val Thr Val Lys Val Met Gly Asp Asp Gly Val Leu Ala Cys
1               5                   10                  15

Ala Ile Ala Thr His Ala Lys Ile Arg Asp
            20                  25

<210> SEQ ID NO 28
<211> LENGTH: 49
<212> TYPE: PRT
<213> ORGANISM: artificial sequence
<220> FEATURE:
<223> OTHER INFORMATION: Peptide

<400> SEQUENCE: 28

Asp Ala Phe Arg His Tyr Asp Gly Arg Thr Ile Ile Gln Arg Asp Asn
1               5                   10                  15

Gly Tyr Gln Pro Asn Tyr His Ala Val Asn Ile Val Gly Tyr Ser Asn
            20                  25                  30

Ala Gln Gly Val Asp Tyr Trp Ile Val Arg Asn Ser Trp Asp Thr Asn
        35                  40                  45

Trp

<210> SEQ ID NO 29
<211> LENGTH: 25
<212> TYPE: PRT
<213> ORGANISM: artificial sequence
<220> FEATURE:
<223> OTHER INFORMATION: Peptide

<400> SEQUENCE: 29

His Glu Ile Lys Lys Val Leu Val Pro Gly Cys His Gly Ser Glu Pro
1               5                   10                  15

Cys Ile Ile His Arg Gly Lys Pro Phe
            20                  25

<210> SEQ ID NO 30
<211> LENGTH: 416
<212> TYPE: PRT
<213> ORGANISM: artificial sequence
<220> FEATURE:
<223> OTHER INFORMATION: Immunogen-coil

<400> SEQUENCE: 30

Gly Val Leu Ala Cys Ala Ile Ala Thr His Ala Lys Ile Arg Glu Gln
1               5                   10                  15

Glu Arg Leu Val Lys Leu Glu Thr Val Lys Lys Ser Leu Glu Gln Glu
            20                  25                  30

Val Arg Thr Leu His Val Arg Ile Glu Glu Val Glu Ala Asn Ala Leu
        35                  40                  45

Ala Gly Gly Asp Leu Arg Gln Met Arg Thr Val Thr Pro Ile Arg Met
    50                  55                  60

-continued

Gln Gly Gly Cys Gly Ser Cys Trp Glu Ala His Glu Gln Gln Ile Arg
 65                  70                  75                  80

Ile Met Thr Thr Lys Leu Lys Glu Ala Glu Ala Arg Gln Gln Tyr Asp
                 85                  90                  95

Ile Lys Tyr Thr Trp Asn Val Pro Lys Ile Ala Val Asn Ile Val Gly
                100                 105                 110

Tyr Ser Asn Ala Gln Gly Val Asp Tyr Trp Ile Val Arg Asn Ser Trp
            115                 120                 125

Asp Thr Asn Trp Tyr His Asn Pro His Phe Ile Gly Asn Arg Ser Val
            130                 135                 140

Ile Thr His Leu Met Glu Asp Leu Lys Gly Glu Leu Asp Met Arg Asn
145                 150                 155                 160

Ile Gln Val Arg Gly Leu Lys Gln Met Lys Arg Val Gly Asp Ala Asn
                165                 170                 175

Val Lys Ser Glu Asp Asp Ala Phe Arg His Tyr Asp Gly Arg Thr Ile
            180                 185                 190

Ile Gln Arg Asp Asn Gly Tyr Gln Pro Asn Tyr Leu Asp Glu Tyr Trp
            195                 200                 205

Ile Leu Thr Ala Ala His Cys Val Asp Gly Gln Thr Val Ser Lys Leu
            210                 215                 220

Ile Arg Ser Lys Val Leu Gly Glu Lys Ile Ser Tyr Arg Tyr Val
225                 230                 235                 240

Ala Arg Glu Gln Ser Cys Arg Arg Pro Asn Ala Gln Arg Phe Gly Ile
                245                 250                 255

Ser Asn Tyr Cys Val Val Thr Val Lys Val Met Gly Asp Asp Glu
            260                 265                 270

Leu His Thr Tyr Phe Asn Val Asn Tyr Thr Met His Tyr Tyr Leu Asn
            275                 280                 285

Asn Gly Ala Thr Arg Asp Ile Leu Asp Glu Tyr Trp Ile Leu Thr Ala
            290                 295                 300

Ala His Cys Val Ala Gly Gln Thr Ala Ser Lys Leu Ser Ile Arg Tyr
305                 310                 315                 320

Asn Ser Leu Lys His Ser Leu Phe Lys Tyr Arg Pro Phe Lys Val Asn
                325                 330                 335

Glu Leu Asn Leu Glu Gly Glu Phe Gly Arg Glu Leu Gln His Lys Phe
            340                 345                 350

Arg Leu Met Arg Asn Ser Gln Met Glu Val Glu Gly Gly Ser
            355                 360                 365

His His His His His His Gly Gly Gly Ser Cys Gly Gly Lys Val Ser
            370                 375                 380

Ala Leu Lys Glu Lys Val Ser Ala Leu Lys Glu Lys Val Ser Ala Leu
385                 390                 395                 400

Lys Glu Lys Val Ser Ala Leu Lys Glu Lys Val Ser Ala Leu Lys Glu
                405                 410                 415

<210> SEQ ID NO 31
<211> LENGTH: 14
<212> TYPE: PRT
<213> ORGANISM: artificial sequence
<220> FEATURE:
<223> OTHER INFORMATION: Peptide

<400> SEQUENCE: 31

Gly Val Leu Ala Cys Ala Ile Ala Thr His Ala Lys Ile Arg
1               5                   10

```
<210> SEQ ID NO 32
<211> LENGTH: 37
<212> TYPE: PRT
<213> ORGANISM: artificial sequence
<220> FEATURE:
<223> OTHER INFORMATION: Peptide

<400> SEQUENCE: 32

Glu Gln Glu Arg Leu Val Lys Leu Glu Thr Val Lys Lys Ser Leu Glu
1               5                   10                  15

Gln Glu Val Arg Thr Leu His Val Arg Ile Glu Glu Val Glu Ala Asn
            20                  25                  30

Ala Leu Ala Gly Gly
        35

<210> SEQ ID NO 33
<211> LENGTH: 21
<212> TYPE: PRT
<213> ORGANISM: artificial sequence
<220> FEATURE:
<223> OTHER INFORMATION: Peptide

<400> SEQUENCE: 33

Asp Leu Arg Gln Met Arg Thr Val Thr Pro Ile Arg Met Gln Gly Gly
1               5                   10                  15

Cys Gly Ser Cys Trp
            20

<210> SEQ ID NO 34
<211> LENGTH: 20
<212> TYPE: PRT
<213> ORGANISM: artificial sequence
<220> FEATURE:
<223> OTHER INFORMATION: Peptide

<400> SEQUENCE: 34

Glu Ala His Glu Gln Gln Ile Arg Ile Met Thr Thr Lys Leu Lys Glu
1               5                   10                  15

Ala Glu Ala Arg
            20

<210> SEQ ID NO 35
<211> LENGTH: 14
<212> TYPE: PRT
<213> ORGANISM: artificial sequence
<220> FEATURE:
<223> OTHER INFORMATION: Peptide

<400> SEQUENCE: 35

Gln Gln Tyr Asp Ile Lys Tyr Thr Trp Asn Val Pro Lys Ile
1               5                   10

<210> SEQ ID NO 36
<211> LENGTH: 31
<212> TYPE: PRT
<213> ORGANISM: artificial sequence
<220> FEATURE:
<223> OTHER INFORMATION: Peptide

<400> SEQUENCE: 36

Asp Leu Lys Gly Glu Leu Asp Met Arg Asn Ile Gln Val Arg Gly Leu
1               5                   10                  15

Lys Gln Met Lys Arg Val Gly Asp Ala Asn Val Lys Ser Glu Asp
            20                  25                  30
```

```
<210> SEQ ID NO 37
<211> LENGTH: 22
<212> TYPE: PRT
<213> ORGANISM: artificial sequence
<220> FEATURE:
<223> OTHER INFORMATION: Peptide

<400> SEQUENCE: 37

Asp Ala Phe Arg His Tyr Asp Gly Arg Thr Ile Ile Gln Arg Asp Asn
1               5                   10                  15

Gly Tyr Gln Pro Asn Tyr
            20

<210> SEQ ID NO 38
<211> LENGTH: 32
<212> TYPE: PRT
<213> ORGANISM: artificial sequence
<220> FEATURE:
<223> OTHER INFORMATION: Peptide

<400> SEQUENCE: 38

Leu Asp Glu Tyr Trp Ile Leu Thr Ala Ala His Cys Val Asp Gly Gln
1               5                   10                  15

Thr Val Ser Lys Leu Ile Arg Ser Lys Val Leu Gly Glu Lys Ile Ser
            20                  25                  30

<210> SEQ ID NO 39
<211> LENGTH: 25
<212> TYPE: PRT
<213> ORGANISM: artificial sequence
<220> FEATURE:
<223> OTHER INFORMATION: Peptide

<400> SEQUENCE: 39

Tyr Tyr Arg Tyr Val Ala Arg Glu Gln Ser Cys Arg Arg Pro Asn Ala
1               5                   10                  15

Gln Arg Phe Gly Ile Ser Asn Tyr Cys
            20                  25

<210> SEQ ID NO 40
<211> LENGTH: 11
<212> TYPE: PRT
<213> ORGANISM: artificial sequence
<220> FEATURE:
<223> OTHER INFORMATION: Peptide

<400> SEQUENCE: 40

Val Val Val Thr Val Lys Val Met Gly Asp Asp
1               5                   10

<210> SEQ ID NO 41
<211> LENGTH: 23
<212> TYPE: PRT
<213> ORGANISM: artificial sequence
<220> FEATURE:
<223> OTHER INFORMATION: Peptide

<400> SEQUENCE: 41

Glu Leu His Thr Tyr Phe Asn Val Asn Tyr Thr Met His Tyr Tyr Leu
1               5                   10                  15

Asn Asn Gly Ala Thr Arg Asp
            20
```

<210> SEQ ID NO 42
<211> LENGTH: 33
<212> TYPE: PRT
<213> ORGANISM: artificial sequence
<220> FEATURE:
<223> OTHER INFORMATION: Peptide

<400> SEQUENCE: 42

Ile Leu Asp Glu Tyr Trp Ile Leu Thr Ala Ala His Cys Val Ala Gly
1               5                   10                  15

Gln Thr Ala Ser Lys Leu Ser Ile Arg Tyr Asn Ser Leu Lys His Ser
            20                  25                  30

Leu

<210> SEQ ID NO 43
<211> LENGTH: 37
<212> TYPE: PRT
<213> ORGANISM: artificial sequence
<220> FEATURE:
<223> OTHER INFORMATION: Peptide

<400> SEQUENCE: 43

Phe Lys Tyr Arg Pro Phe Lys Val Asn Glu Leu Asn Leu Glu Gly Glu
1               5                   10                  15

Phe Gly Arg Glu Leu Gln His Lys Phe Arg Leu Met Arg Asn Ser Gln
            20                  25                  30

Met Glu Val Glu Glu
        35

<210> SEQ ID NO 44
<211> LENGTH: 250
<212> TYPE: PRT
<213> ORGANISM: artificial sequence
<220> FEATURE:
<223> OTHER INFORMATION: ScFV

<400> SEQUENCE: 44

Glu Val Gln Leu Gln Gln Ser Gly Pro Glu Leu Lys Lys Pro Gly Glu
1               5                   10                  15

Thr Val Lys Ile Ser Cys Lys Ala Ser Gly Tyr Thr Phe Thr Asn Tyr
            20                  25                  30

Gly Met Asn Trp Val Lys Gln Ala Pro Gly Lys Gly Leu Lys Trp Met
        35                  40                  45

Gly Trp Leu Asn Thr Tyr Thr Gly Glu Ser Ile Tyr Pro Asp Asp Phe
    50                  55                  60

Lys Gly Arg Phe Ala Phe Ser Ser Glu Thr Ser Ala Ser Thr Ala Tyr
65                  70                  75                  80

Leu Gln Ile Asn Asn Leu Lys Asn Glu Asp Met Ala Thr Tyr Phe Cys
                85                  90                  95

Ala Arg Gly Asp Tyr Gly Tyr Asp Asp Pro Leu Asp Tyr Trp Gly Gln
            100                 105                 110

Gly Thr Ser Val Thr Val Ser Ser Gly Gly Gly Gly Ser Gly Gly Gly
        115                 120                 125

Gly Ser Gly Gly Gly Gly Ser Asp Ile Val Met Thr Gln Ala Ala Pro
    130                 135                 140

Ser Val Pro Val Thr Pro Gly Glu Ser Val Ser Ile Ser Cys Arg Ser
145                 150                 155                 160

Ser Lys Ser Leu Leu His Thr Asn Gly Asn Thr Tyr Leu His Trp Phe
                165                 170                 175

```
Leu Gln Arg Pro Gly Gln Ser Pro Gln Leu Ile Tyr Arg Met Ser
            180                 185                 190

Val Leu Ala Ser Gly Val Pro Asp Arg Phe Ser Gly Ser Gly Ser Gly
        195                 200                 205

Thr Ala Phe Thr Leu Ser Ile Ser Arg Val Glu Ala Glu Asp Val Gly
    210                 215                 220

Val Phe Tyr Cys Met Gln His Leu Glu Tyr Pro Leu Thr Phe Gly Ala
225                 230                 235                 240

Gly Thr Lys Leu Glu Leu Lys Gly Ser Ile
            245                 250
```

<210> SEQ ID NO 45
<211> LENGTH: 19
<212> TYPE: PRT
<213> ORGANISM: artificial sequence
<220> FEATURE:
<223> OTHER INFORMATION: Peptide

<400> SEQUENCE: 45

```
Ala Asp Gly Ala Trp Ala Trp Val Trp Leu Thr Glu Thr Ala Val Gly
1               5                   10                  15

Ala Ala Lys
```

<210> SEQ ID NO 46
<211> LENGTH: 249
<212> TYPE: PRT
<213> ORGANISM: artificial sequence
<220> FEATURE:
<223> OTHER INFORMATION: ScFV

<400> SEQUENCE: 46

```
Glu Val Lys Leu Glu Glu Ser Gly Gly Gly Leu Val Gln Pro Gly Gly
1               5                   10                  15

Ser Met Lys Leu Ser Cys Val Ala Ser Gly Phe Thr Phe Ser Tyr Tyr
            20                  25                  30

Trp Met Asn Trp Val Arg Gln Ser Pro Glu Lys Gly Leu Glu Trp Val
        35                  40                  45

Ala Glu Ile Arg Leu Lys Ser Asn Asn Tyr Ala Thr His Tyr Ala Glu
    50                  55                  60

Ser Val Lys Gly Arg Phe Thr Ile Ser Arg Asp Asp Ser Lys Asn Asn
65                  70                  75                  80

Val Tyr Leu Gln Met Asn Asn Leu Arg Ala Glu Asp Thr Gly Ile Tyr
            85                  90                  95

Tyr Cys Asn Arg Arg Asp Glu Tyr Tyr Ala Met Asp Tyr Trp Gly Gln
        100                 105                 110

Gly Thr Ser Val Ser Val Ser Ser Gly Gly Gly Gly Ser Gly Gly Gly
    115                 120                 125

Gly Ser Gly Gly Gly Gly Ser Asp Ile Val Leu Thr Gln Ser Pro Gly
130                 135                 140

Ser Leu Ala Val Ser Leu Gly Gln Arg Ala Thr Ile Ser Cys Arg Ala
145                 150                 155                 160

Ser Glu Ser Val Asp Asn Phe Gly Ile Ser Phe Met Asn Trp Phe Gln
            165                 170                 175

Gln Lys Pro Gly Gln Pro Pro Arg Leu Leu Ile Tyr Gly Ala Ser Asn
        180                 185                 190

Gln Gly Ser Gly Val Pro Ala Arg Phe Ser Gly Ser Gly Ser Gly Thr
    195                 200                 205
```

```
Asp Phe Ser Leu Asn Ile His Pro Val Glu Glu Asp Ala Ala Met
            210                 215                 220

Tyr Phe Cys Gln Gln Ser Lys Glu Val Pro Trp Thr Phe Gly Gly Gly
225                 230                 235                 240

Thr Lys Leu Glu Ile Lys Gly Ser Ile
                245

<210> SEQ ID NO 47
<211> LENGTH: 230
<212> TYPE: PRT
<213> ORGANISM: artificial sequence
<220> FEATURE:
<223> OTHER INFORMATION: IgG1 Fc

<400> SEQUENCE: 47

Pro Lys Ser Cys Asp Lys Thr His Thr Cys Pro Pro Cys Pro Pro Glu
1               5                   10                  15

Leu Leu Gly Gly Pro Ser Val Phe Leu Phe Pro Pro Lys Pro Lys Asp
            20                  25                  30

Thr Leu Met Ile Ser Arg Thr Pro Glu Val Thr Cys Val Val Val Asp
        35                  40                  45

Val Ser His Glu Asp Pro Glu Val Lys Phe Asn Trp Tyr Val Asp Gly
    50                  55                  60

Val Glu Val His Asn Ala Lys Thr Lys Pro Arg Glu Glu Gln Tyr Asn
65                  70                  75                  80

Ser Thr Tyr Arg Val Val Ser Val Leu Thr Val Leu His Gln Asp Trp
                85                  90                  95

Leu Asn Gly Lys Glu Tyr Lys Cys Lys Val Ser Asn Lys Ala Leu Pro
            100                 105                 110

Ala Pro Ile Glu Lys Thr Ile Ser Lys Ala Lys Gly Gln Pro Arg Glu
        115                 120                 125

Pro Gln Val Tyr Thr Leu Pro Pro Ser Arg Asp Glu Leu Thr Lys Asn
    130                 135                 140

Gln Val Ser Leu Thr Cys Leu Val Lys Gly Phe Tyr Pro Ser Asp Ile
145                 150                 155                 160

Ala Val Glu Trp Glu Ser Asn Gly Gln Pro Glu Asn Asn Tyr Lys Thr
                165                 170                 175

Thr Pro Pro Val Leu Asp Ser Asp Gly Ser Phe Phe Leu Tyr Ser Lys
            180                 185                 190

Leu Thr Val Asp Lys Ser Arg Trp Gln Gln Gly Asn Val Phe Ser Cys
        195                 200                 205

Ser Val Met His Glu Ala Leu His Asn His Tyr Thr Gln Lys Ser Leu
    210                 215                 220

Ser Leu Ser Pro Gly Lys
225                 230

<210> SEQ ID NO 48
<211> LENGTH: 20
<212> TYPE: PRT
<213> ORGANISM: artificial sequence
<220> FEATURE:
<223> OTHER INFORMATION: Peptide

<400> SEQUENCE: 48

Gly Gly Gly Gly Gly Ala Cys Gly Ala Thr Cys Gly Thr Cys Gly Gly
1               5                   10                  15

Gly Gly Gly Gly
            20
```

```
<210> SEQ ID NO 49
<211> LENGTH: 24
<212> TYPE: PRT
<213> ORGANISM: artificial sequence
<220> FEATURE:
<223> OTHER INFORMATION: Peptide

<400> SEQUENCE: 49

Thr Cys Gly Thr Cys Gly Thr Thr Thr Gly Thr Cys Gly Thr Thr
1               5                   10                  15

Thr Thr Gly Thr Cys Gly Thr Thr
            20

<210> SEQ ID NO 50
<211> LENGTH: 12
<212> TYPE: PRT
<213> ORGANISM: artificial sequence
<220> FEATURE:
<223> OTHER INFORMATION: Peptide

<400> SEQUENCE: 50

Glu Ser Trp Asp Lys Phe Leu Ser His Tyr Leu Pro
1               5                   10

<210> SEQ ID NO 51
<211> LENGTH: 7
<212> TYPE: PRT
<213> ORGANISM: artificial sequence
<220> FEATURE:
<223> OTHER INFORMATION: Peptide

<400> SEQUENCE: 51

Thr Asp Trp Ser Trp Phe Tyr
1               5

<210> SEQ ID NO 52
<211> LENGTH: 7
<212> TYPE: PRT
<213> ORGANISM: artificial sequence
<220> FEATURE:
<223> OTHER INFORMATION: Peptide

<400> SEQUENCE: 52

Tyr Pro Val Tyr Trp Pro Trp
1               5

<210> SEQ ID NO 53
<211> LENGTH: 7
<212> TYPE: PRT
<213> ORGANISM: artificial sequence
<220> FEATURE:
<223> OTHER INFORMATION: Peptide

<400> SEQUENCE: 53

Glu Trp Trp Phe Tyr Trp Pro
1               5

<210> SEQ ID NO 54
<211> LENGTH: 7
<212> TYPE: PRT
<213> ORGANISM: artificial sequence
<220> FEATURE:
<223> OTHER INFORMATION: Peptide

<400> SEQUENCE: 54
```

```
Trp Phe Pro Ile Glu Trp Trp
1               5

<210> SEQ ID NO 55
<211> LENGTH: 7
<212> TYPE: PRT
<213> ORGANISM: artificial sequence
<220> FEATURE:
<223> OTHER INFORMATION: Peptide

<400> SEQUENCE: 55

Asp Gln Val Asp Ile Gly Tyr
1               5

<210> SEQ ID NO 56
<211> LENGTH: 7
<212> TYPE: PRT
<213> ORGANISM: artificial sequence
<220> FEATURE:
<223> OTHER INFORMATION: Peptide

<400> SEQUENCE: 56

Thr His Gln Val Tyr Ile Ser
1               5

<210> SEQ ID NO 57
<211> LENGTH: 11
<212> TYPE: PRT
<213> ORGANISM: artificial sequence
<220> FEATURE:
<223> OTHER INFORMATION: Peptide

<400> SEQUENCE: 57

Trp Phe Pro Ile Glu Trp Trp Phe Tyr Trp Pro
1               5                   10

<210> SEQ ID NO 58
<211> LENGTH: 12
<212> TYPE: PRT
<213> ORGANISM: artificial sequence
<220> FEATURE:
<223> OTHER INFORMATION: Peptide

<400> SEQUENCE: 58

Asp Ser Trp Gln Ala Phe Leu Thr Lys Phe Val Leu
1               5                   10

<210> SEQ ID NO 59
<211> LENGTH: 12
<212> TYPE: PRT
<213> ORGANISM: artificial sequence
<220> FEATURE:
<223> OTHER INFORMATION: Peptide

<400> SEQUENCE: 59

His Asp Ile Gln Trp Phe Trp Gln His Trp Asn Ser
1               5                   10

<210> SEQ ID NO 60
<211> LENGTH: 12
<212> TYPE: PRT
<213> ORGANISM: artificial sequence
<220> FEATURE:
<223> OTHER INFORMATION: Peptide

<400> SEQUENCE: 60

Trp Ser Trp Trp Asp His Thr Phe Asn Tyr Met Leu
```

-continued

```
1               5                   10
```

<210> SEQ ID NO 61
<211> LENGTH: 12
<212> TYPE: PRT
<213> ORGANISM: artificial sequence
<220> FEATURE:
<223> OTHER INFORMATION: Peptide

<400> SEQUENCE: 61

```
Thr Thr Gln Gln Thr Trp Asn Val Arg Tyr Pro Tyr
1               5                   10
```

<210> SEQ ID NO 62
<211> LENGTH: 12
<212> TYPE: PRT
<213> ORGANISM: artificial sequence
<220> FEATURE:
<223> OTHER INFORMATION: Peptide

<400> SEQUENCE: 62

```
Asp His Thr Met Pro Trp Thr Arg Asn Ala Lys Asn
1               5                   10
```

<210> SEQ ID NO 63
<211> LENGTH: 12
<212> TYPE: PRT
<213> ORGANISM: artificial sequence
<220> FEATURE:
<223> OTHER INFORMATION: Peptide

<400> SEQUENCE: 63

```
Ser Trp Asp Pro Tyr Trp Pro Phe Pro Trp Phe Ser
1               5                   10
```

<210> SEQ ID NO 64
<211> LENGTH: 12
<212> TYPE: PRT
<213> ORGANISM: artificial sequence
<220> FEATURE:
<223> OTHER INFORMATION: Peptide

<400> SEQUENCE: 64

```
Ala Ile Tyr Tyr Val Pro Ser Pro Met Phe Thr Val
1               5                   10
```

<210> SEQ ID NO 65
<211> LENGTH: 12
<212> TYPE: PRT
<213> ORGANISM: artificial sequence
<220> FEATURE:
<223> OTHER INFORMATION: Peptide

<400> SEQUENCE: 65

```
Glu Thr Thr Leu Leu Lys Met Trp Leu Ala Gln Met
1               5                   10
```

<210> SEQ ID NO 66
<211> LENGTH: 12
<212> TYPE: PRT
<213> ORGANISM: artificial sequence
<220> FEATURE:
<223> OTHER INFORMATION: Peptide

<400> SEQUENCE: 66

```
Tyr Pro Trp Leu Asp Val Ala Val Val Ser Leu Tyr
1               5                   10
```

```
<210> SEQ ID NO 67
<211> LENGTH: 12
<212> TYPE: PRT
<213> ORGANISM: artificial sequence
<220> FEATURE:
<223> OTHER INFORMATION: Peptide

<400> SEQUENCE: 67

Val Pro Gly Trp His Tyr Leu Ala Thr Leu Arg Ala
1               5                   10

<210> SEQ ID NO 68
<211> LENGTH: 12
<212> TYPE: PRT
<213> ORGANISM: artificial sequence
<220> FEATURE:
<223> OTHER INFORMATION: Peptide

<400> SEQUENCE: 68

Phe Asp Pro Leu Gly Ser Arg Asp Ile Lys Gly Ser
1               5                   10

<210> SEQ ID NO 69
<211> LENGTH: 25
<212> TYPE: PRT
<213> ORGANISM: artificial sequence
<220> FEATURE:
<223> OTHER INFORMATION: Peptide

<400> SEQUENCE: 69

Thr Cys Gly Thr Cys Gly Thr Cys Gly Thr Cys Gly Ala Ala Cys
1               5                   10                  15

Gly Ala Cys Gly Thr Thr Gly Ala Thr
                20                  25

<210> SEQ ID NO 70
<211> LENGTH: 297
<212> TYPE: PRT
<213> ORGANISM: artificial sequence
<220> FEATURE:
<223> OTHER INFORMATION: ScFV-coil

<400> SEQUENCE: 70

Glu Val Gln Leu Gln Gln Ser Gly Pro Glu Leu Lys Lys Pro Gly Glu
1               5                   10                  15

Thr Val Lys Ile Ser Cys Lys Ala Ser Gly Tyr Thr Phe Thr Asn Tyr
                20                  25                  30

Gly Met Asn Trp Val Lys Gln Ala Pro Gly Lys Gly Leu Lys Trp Met
        35                  40                  45

Gly Trp Leu Asn Thr Tyr Thr Gly Glu Ser Ile Tyr Pro Asp Asp Phe
    50                  55                  60

Lys Gly Arg Phe Ala Phe Ser Ser Glu Thr Ser Ala Ser Thr Ala Tyr
65                  70                  75                  80

Leu Gln Ile Asn Asn Leu Lys Asn Glu Asp Met Ala Thr Tyr Phe Cys
                85                  90                  95

Ala Arg Gly Asp Tyr Gly Tyr Asp Asp Pro Leu Asp Tyr Trp Gly Gln
            100                 105                 110

Gly Thr Ser Val Thr Val Ser Ser Gly Gly Gly Ser Gly Gly Gly
        115                 120                 125

Gly Ser Gly Gly Gly Gly Ser Asp Ile Val Met Thr Gln Ala Ala Pro
    130                 135                 140
```

```
Ser Val Pro Val Thr Pro Gly Glu Ser Val Ser Ile Ser Cys Arg Ser
145                 150                 155                 160

Ser Lys Ser Leu Leu His Thr Asn Gly Asn Thr Tyr Leu His Trp Phe
            165                 170                 175

Leu Gln Arg Pro Gly Gln Ser Pro Gln Leu Leu Ile Tyr Arg Met Ser
        180                 185                 190

Val Leu Ala Ser Gly Val Pro Asp Arg Phe Ser Gly Ser Gly Ser Gly
    195                 200                 205

Thr Ala Phe Thr Leu Ser Ile Ser Arg Val Glu Ala Glu Asp Val Gly
210                 215                 220

Val Phe Tyr Cys Met Gln His Leu Glu Tyr Pro Leu Thr Phe Gly Ala
225                 230                 235                 240

Gly Thr Lys Leu Glu Leu Lys Gly Ser Ile Ser Ala Trp Ser His Pro
                245                 250                 255

Gln Phe Glu Lys Gly Pro Glu Val Ser Ala Leu Glu Lys Glu Val Ser
            260                 265                 270

Ala Leu Glu Lys Glu Val Ser Ala Leu Glu Lys Glu Val Ser Ala Leu
            275                 280                 285

Glu Lys Glu Val Ser Ala Leu Glu Lys
    290                 295
```

<210> SEQ ID NO 71
<211> LENGTH: 296
<212> TYPE: PRT
<213> ORGANISM: artificial sequence
<220> FEATURE:
<223> OTHER INFORMATION: ScFV-coil

<400> SEQUENCE: 71

```
Glu Val Lys Leu Glu Glu Ser Gly Gly Gly Leu Val Gln Pro Gly Gly
1               5                   10                  15

Ser Met Lys Leu Ser Cys Val Ala Ser Gly Phe Thr Phe Ser Tyr Tyr
            20                  25                  30

Trp Met Asn Trp Val Arg Gln Ser Pro Glu Lys Gly Leu Glu Trp Val
        35                  40                  45

Ala Glu Ile Arg Leu Lys Ser Asn Asn Tyr Ala Thr His Tyr Ala Glu
    50                  55                  60

Ser Val Lys Gly Arg Phe Thr Ile Ser Arg Asp Asp Ser Lys Asn Asn
65                  70                  75                  80

Val Tyr Leu Gln Met Asn Asn Leu Arg Ala Glu Asp Thr Gly Ile Tyr
                85                  90                  95

Tyr Cys Asn Arg Arg Asp Glu Tyr Tyr Ala Met Asp Tyr Trp Gly Gln
            100                 105                 110

Gly Thr Ser Val Ser Val Ser Gly Gly Gly Gly Ser Gly Gly Gly Gly
        115                 120                 125

Gly Ser Gly Gly Gly Gly Ser Asp Ile Val Leu Thr Gln Ser Pro Gly
    130                 135                 140

Ser Leu Ala Val Ser Leu Gly Gln Arg Ala Thr Ile Ser Cys Arg Ala
145                 150                 155                 160

Ser Glu Ser Val Asp Asn Phe Gly Ile Ser Phe Met Asn Trp Phe Gln
                165                 170                 175

Gln Lys Pro Gly Gln Pro Pro Arg Leu Leu Ile Tyr Gly Ala Ser Asn
            180                 185                 190

Gln Gly Ser Gly Val Pro Ala Arg Phe Ser Gly Ser Gly Ser Gly Thr
        195                 200                 205
```

```
Asp Phe Ser Leu Asn Ile His Pro Val Glu Glu Asp Ala Ala Met
        210                 215                 220

Tyr Phe Cys Gln Gln Ser Lys Glu Val Pro Trp Thr Phe Gly Gly Gly
225                 230                 235                 240

Thr Lys Leu Glu Ile Lys Gly Ser Ile Ser Ala Trp Ser His Pro Gln
                245                 250                 255

Phe Glu Lys Gly Pro Glu Val Ser Ala Leu Glu Lys Glu Val Ser Ala
                260                 265                 270

Leu Glu Lys Glu Val Ser Ala Leu Glu Lys Glu Val Ser Ala Leu Glu
            275                 280                 285

Lys Glu Val Ser Ala Leu Glu Lys
        290                 295

<210> SEQ ID NO 72
<211> LENGTH: 56
<212> TYPE: PRT
<213> ORGANISM: artificial sequence
<220> FEATURE:
<223> OTHER INFORMATION: Peptide-coil

<400> SEQUENCE: 72

Ala Asp Gly Ala Trp Ala Trp Val Trp Leu Thr Glu Thr Ala Val Gly
1               5                   10                  15

Ala Ala Lys Gly Pro Glu Val Ser Ala Leu Glu Lys Glu Val Ser Ala
            20                  25                  30

Leu Glu Lys Glu Val Ser Ala Leu Glu Lys Glu Val Ser Ala Leu Glu
        35                  40                  45

Lys Glu Val Ser Ala Leu Glu Lys
    50                  55

<210> SEQ ID NO 73
<211> LENGTH: 267
<212> TYPE: PRT
<213> ORGANISM: artificial sequence
<220> FEATURE:
<223> OTHER INFORMATION: IgG1 Fc-coil

<400> SEQUENCE: 73

Pro Lys Ser Cys Asp Lys Thr His Thr Cys Pro Pro Cys Pro Pro Glu
1               5                   10                  15

Leu Leu Gly Gly Pro Ser Val Phe Leu Phe Pro Pro Lys Pro Lys Asp
                20                  25                  30

Thr Leu Met Ile Ser Arg Thr Pro Glu Val Thr Cys Val Val Val Asp
            35                  40                  45

Val Ser His Glu Asp Pro Glu Val Lys Phe Asn Trp Tyr Val Asp Gly
        50                  55                  60

Val Glu Val His Asn Ala Lys Thr Lys Pro Arg Glu Glu Gln Tyr Asn
65                  70                  75                  80

Ser Thr Tyr Arg Val Val Ser Val Leu Thr Val Leu His Gln Asp Trp
                85                  90                  95

Leu Asn Gly Lys Glu Tyr Lys Cys Lys Val Ser Asn Lys Ala Leu Pro
            100                 105                 110

Ala Pro Ile Glu Lys Thr Ile Ser Lys Ala Lys Gly Gln Pro Arg Glu
        115                 120                 125

Pro Gln Val Tyr Thr Leu Pro Pro Ser Arg Asp Glu Leu Thr Lys Asn
    130                 135                 140

Gln Val Ser Leu Thr Cys Leu Val Lys Gly Phe Tyr Pro Ser Asp Ile
```

Ala Val Glu Trp Glu Ser Asn Gly Gln Pro Glu Asn Asn Tyr Lys Thr
145                 150                 155                 160

Thr Pro Pro Val Leu Asp Ser Asp Gly Ser Phe Phe Leu Tyr Ser Lys
            165                 170                 175

Leu Thr Val Asp Lys Ser Arg Trp Gln Gln Gly Asn Val Phe Ser Cys
                180                 185                 190

Ser Val Met His Glu Ala Leu His Asn His Tyr Thr Gln Lys Ser Leu
            195                 200                 205

Ser Leu Ser Pro Gly Lys Gly Pro Glu Val Ser Ala Leu Glu Lys Glu
225                 230                 235                 240

Val Ser Ala Leu Glu Lys Glu Val Ser Ala Leu Glu Lys Glu Val Ser
            245                 250                 255

Ala Leu Glu Lys Glu Val Ser Ala Leu Glu Lys
            260                 265

<210> SEQ ID NO 74
<211> LENGTH: 253
<212> TYPE: PRT
<213> ORGANISM: artificial sequence
<220> FEATURE:
<223> OTHER INFORMATION: Immunogen-coil

<400> SEQUENCE: 74

His His His His His His Tyr Tyr Arg Tyr Val Ala Arg Glu Gln Ser
1               5                   10                  15

Cys Arg Arg Pro Asn Ala Gln Arg Phe Gly Ile Ser Asn Tyr Cys Gln
            20                  25                  30

Ile Tyr Pro Pro Asn Val Asn Lys Ile Arg Glu Ala Leu Ala Gln Thr
            35                  40                  45

His Ser Ala Ile Ala Val Asp Leu Arg Gln Met Arg Thr Val Thr Pro
50                  55                  60

Ile Arg Met Gln Gly Gly Cys Gly Ser Cys Trp Ala Phe Ser Gly Val
65                  70                  75                  80

Ala Ala Thr Glu Ser Ala Tyr Leu Gln Gln Tyr Asp Ile Lys Tyr Thr
            85                  90                  95

Trp Asn Val Pro Lys Ile Ala Pro Lys Ser Glu Asn Val Val Val Thr
            100                 105                 110

Val Lys Val Met Gly Asp Asp Gly Val Leu Ala Cys Ala Ile Ala Thr
            115                 120                 125

His Ala Lys Ile Arg Asp Asp Ala Phe Arg His Tyr Asp Gly Arg Thr
130                 135                 140

Ile Ile Gln Arg Asp Asn Gly Tyr Gln Pro Asn Tyr His Ala Val Asn
145                 150                 155                 160

Ile Val Gly Tyr Ser Asn Ala Gln Gly Val Asp Tyr Trp Ile Val Arg
            165                 170                 175

Asn Ser Trp Asp Thr Asn Trp His Glu Ile Lys Lys Val Leu Val Pro
            180                 185                 190

Gly Cys His Gly Ser Glu Pro Cys Ile Ile His Arg Gly Lys Pro Phe
            195                 200                 205

Gly Gly Gly Ser Gly Gly Gly Ser Gly Gly Lys Val Ser Ala Leu Lys
            210                 215                 220

Glu Lys Val Ser Ala Leu Lys Glu Lys Val Ser Ala Leu Lys Glu Lys
225                 230                 235                 240

Val Ser Ala Leu Lys Glu Lys Val Ser Ala Leu Lys Glu
            245                 250

```
              245                 250

<210> SEQ ID NO 75
<211> LENGTH: 416
<212> TYPE: PRT
<213> ORGANISM: artificial sequence
<220> FEATURE:
<223> OTHER INFORMATION: Immunogen-coil

<400> SEQUENCE: 75

Gly Val Leu Ala Cys Ala Ile Ala Thr His Ala Lys Ile Arg Glu Gln
1               5                   10                  15

Glu Arg Leu Val Lys Leu Glu Thr Val Lys Lys Ser Leu Glu Gln Glu
            20                  25                  30

Val Arg Thr Leu His Val Arg Ile Glu Glu Val Glu Ala Asn Ala Leu
        35                  40                  45

Ala Gly Gly Asp Leu Arg Gln Met Arg Thr Val Thr Pro Ile Arg Met
    50                  55                  60

Gln Gly Gly Cys Gly Ser Cys Trp Glu Ala His Glu Gln Gln Ile Arg
65                  70                  75                  80

Ile Met Thr Thr Lys Leu Lys Glu Ala Glu Ala Arg Gln Gln Tyr Asp
                85                  90                  95

Ile Lys Tyr Thr Trp Asn Val Pro Lys Ile Ala Val Asn Ile Val Gly
            100                 105                 110

Tyr Ser Asn Ala Gln Gly Val Asp Tyr Trp Ile Val Arg Asn Ser Trp
        115                 120                 125

Asp Thr Asn Trp Tyr His Asn Pro His Phe Ile Gly Asn Arg Ser Val
    130                 135                 140

Ile Thr His Leu Met Glu Asp Leu Lys Gly Glu Leu Asp Met Arg Asn
145                 150                 155                 160

Ile Gln Val Arg Gly Leu Lys Gln Met Lys Arg Val Gly Asp Ala Asn
                165                 170                 175

Val Lys Ser Glu Asp Asp Ala Phe Arg His Tyr Asp Gly Arg Thr Ile
            180                 185                 190

Ile Gln Arg Asp Asn Gly Tyr Gln Pro Asn Tyr Leu Asp Glu Tyr Trp
        195                 200                 205

Ile Leu Thr Ala Ala His Cys Val Asp Gly Gln Thr Val Ser Lys Leu
    210                 215                 220

Ile Arg Ser Lys Val Leu Gly Glu Lys Ile Ser Tyr Arg Tyr Val
225                 230                 235                 240

Ala Arg Glu Gln Ser Cys Arg Arg Pro Asn Ala Gln Arg Phe Gly Ile
                245                 250                 255

Ser Asn Tyr Cys Val Val Thr Val Lys Val Met Gly Asp Asp Glu
            260                 265                 270

Leu His Thr Tyr Phe Asn Val Asn Tyr Thr Met His Tyr Tyr Leu Asn
        275                 280                 285

Asn Gly Ala Thr Arg Asp Ile Leu Asp Glu Tyr Trp Ile Leu Thr Ala
    290                 295                 300

Ala His Cys Val Ala Gly Gln Thr Ala Ser Lys Leu Ser Ile Arg Tyr
305                 310                 315                 320

Asn Ser Leu Lys His Ser Leu Phe Lys Tyr Arg Pro Phe Lys Val Asn
                325                 330                 335

Glu Leu Asn Leu Glu Gly Glu Phe Gly Arg Glu Leu Gln His Lys Phe
            340                 345                 350

Arg Leu Met Arg Asn Ser Gln Met Glu Val Glu Glu Gly Gly Gly Ser
```

```
                355                 360                 365
His His His His His His Gly Gly Gly Ser Cys Gly Gly Lys Val Ser
            370                 375                 380

Ala Leu Lys Glu Lys Val Ser Ala Leu Lys Glu Lys Val Ser Ala Leu
385                 390                 395                 400

Lys Glu Lys Val Ser Ala Leu Lys Glu Lys Val Ser Ala Leu Lys Glu
                405                 410                 415
```

<210> SEQ ID NO 76
<211> LENGTH: 10
<212> TYPE: PRT
<213> ORGANISM: artificial sequence
<220> FEATURE:
<223> OTHER INFORMATION: Peptide

<400> SEQUENCE: 76

```
Ser Ala Trp Ser His Pro Gln Phe Glu Lys
1               5                   10
```

<210> SEQ ID NO 77
<211> LENGTH: 35
<212> TYPE: PRT
<213> ORGANISM: artificial sequence
<220> FEATURE:
<223> OTHER INFORMATION: Peptide

<400> SEQUENCE: 77

```
Glu Val Ser Ala Leu Glu Lys Glu Val Ser Ala Leu Glu Lys Glu Val
1               5                   10                  15

Ser Ala Leu Glu Lys Glu Val Ser Ala Leu Glu Lys Glu Val Ser Ala
            20                  25                  30

Leu Glu Lys
        35
```

<210> SEQ ID NO 78
<211> LENGTH: 17
<212> TYPE: PRT
<213> ORGANISM: artificial sequence
<220> FEATURE:
<223> OTHER INFORMATION: Peptide

<400> SEQUENCE: 78

```
Glu Gly Pro Trp Leu Glu Glu Glu Glu Ala Tyr Gly Trp Met Asp
1               5                   10                  15

Phe
```

<210> SEQ ID NO 79
<211> LENGTH: 12
<212> TYPE: PRT
<213> ORGANISM: artificial sequence
<220> FEATURE:
<223> OTHER INFORMATION: Peptide

<400> SEQUENCE: 79

```
Glu Gly Pro Trp Leu Glu Glu Glu Glu Ala Tyr
1               5                   10
```

<210> SEQ ID NO 80
<211> LENGTH: 4
<212> TYPE: PRT
<213> ORGANISM: artificial sequence
<220> FEATURE:
<223> OTHER INFORMATION: Peptide
<220> FEATURE:

```
<221> NAME/KEY: PEPTIDE
<222> LOCATION: (2)..(2)
<223> OTHER INFORMATION: X is any amino acid
<220> FEATURE:
<221> NAME/KEY: PEPTIDE
<222> LOCATION: (4)..(4)
<223> OTHER INFORMATION: X is any amino acid

<400> SEQUENCE: 80

Glu Xaa Pro Xaa
1

<210> SEQ ID NO 81
<211> LENGTH: 4
<212> TYPE: PRT
<213> ORGANISM: artificial sequence
<220> FEATURE:
<223> OTHER INFORMATION: Peptide
<220> FEATURE:
<221> NAME/KEY: PEPTIDE
<222> LOCATION: (2)..(2)
<223> OTHER INFORMATION: X is any of G or R
<220> FEATURE:
<221> NAME/KEY: PEPTIDE
<222> LOCATION: (4)..(4)
<223> OTHER INFORMATION: X is any of W or R

<400> SEQUENCE: 81

Glu Xaa Pro Xaa
1

<210> SEQ ID NO 82
<211> LENGTH: 12
<212> TYPE: PRT
<213> ORGANISM: artificial sequence
<220> FEATURE:
<223> OTHER INFORMATION: Peptide
<220> FEATURE:
<221> NAME/KEY: PEPTIDE
<222> LOCATION: (2)..(2)
<223> OTHER INFORMATION: X is any amino acid
<220> FEATURE:
<221> NAME/KEY: PEPTIDE
<222> LOCATION: (4)..(4)
<223> OTHER INFORMATION: X is any amino acid
<220> FEATURE:
<221> NAME/KEY: PEPTIDE
<222> LOCATION: (5)..(5)
<223> OTHER INFORMATION: X is any amino acid
<220> FEATURE:
<221> NAME/KEY: PEPTIDE
<222> LOCATION: (10)..(10)
<223> OTHER INFORMATION: X is any amino acid

<400> SEQUENCE: 82

Glu Xaa Pro Xaa Xaa Glu Glu Glu Glu Xaa Ala Tyr
1               5                   10

<210> SEQ ID NO 83
<211> LENGTH: 12
<212> TYPE: PRT
<213> ORGANISM: artificial sequence
<220> FEATURE:
<223> OTHER INFORMATION: Peptide
<220> FEATURE:
<221> NAME/KEY: PEPTIDE
<222> LOCATION: (2)..(2)
<223> OTHER INFORMATION: X is any of G or R
<220> FEATURE:
<221> NAME/KEY: PEPTIDE
<222> LOCATION: (4)..(4)
<223> OTHER INFORMATION: X is any of W or R
<220> FEATURE:
```

```
<221> NAME/KEY: PEPTIDE
<222> LOCATION: (5)..(5)
<223> OTHER INFORMATION: X is any of L or M
<220> FEATURE:
<221> NAME/KEY: PEPTIDE
<222> LOCATION: (10)..(10)
<223> OTHER INFORMATION: X is any of E or A

<400> SEQUENCE: 83

Glu Xaa Pro Xaa Xaa Glu Glu Glu Glu Xaa Ala Tyr
1               5                   10

<210> SEQ ID NO 84
<211> LENGTH: 13
<212> TYPE: PRT
<213> ORGANISM: artificial sequence
<220> FEATURE:
<223> OTHER INFORMATION: Peptide
<220> FEATURE:
<221> NAME/KEY: PEPTIDE
<222> LOCATION: (2)..(2)
<223> OTHER INFORMATION: X is any amino acid
<220> FEATURE:
<221> NAME/KEY: PEPTIDE
<222> LOCATION: (4)..(4)
<223> OTHER INFORMATION: X is any amino acid
<220> FEATURE:
<221> NAME/KEY: PEPTIDE
<222> LOCATION: (5)..(5)
<223> OTHER INFORMATION: X is any amino acid
<220> FEATURE:
<221> NAME/KEY: PEPTIDE
<222> LOCATION: (10)..(10)
<223> OTHER INFORMATION: X is any amino acid

<400> SEQUENCE: 84

Glu Xaa Pro Xaa Xaa Glu Glu Glu Glu Xaa Ala Tyr Gly
1               5                   10

<210> SEQ ID NO 85
<211> LENGTH: 13
<212> TYPE: PRT
<213> ORGANISM: artificial sequence
<220> FEATURE:
<223> OTHER INFORMATION: Peptide
<220> FEATURE:
<221> NAME/KEY: PEPTIDE
<222> LOCATION: (2)..(2)
<223> OTHER INFORMATION: X is any of G or R
<220> FEATURE:
<221> NAME/KEY: PEPTIDE
<222> LOCATION: (4)..(4)
<223> OTHER INFORMATION: X is any of W or R
<220> FEATURE:
<221> NAME/KEY: PEPTIDE
<222> LOCATION: (5)..(5)
<223> OTHER INFORMATION: X is any of L or M
<220> FEATURE:
<221> NAME/KEY: PEPTIDE
<222> LOCATION: (10)..(10)
<223> OTHER INFORMATION: X is any of E or A

<400> SEQUENCE: 85

Glu Xaa Pro Xaa Xaa Glu Glu Glu Glu Xaa Ala Tyr Gly
1               5                   10

<210> SEQ ID NO 86
<211> LENGTH: 13
<212> TYPE: PRT
<213> ORGANISM: artificial sequence
<220> FEATURE:
<223> OTHER INFORMATION: Peptide
```

```
<400> SEQUENCE: 86

Glu Gly Pro Trp Leu Glu Glu Glu Glu Ala Tyr Gly
1               5                   10

<210> SEQ ID NO 87
<211> LENGTH: 53
<212> TYPE: PRT
<213> ORGANISM: artificial sequence
<220> FEATURE:
<223> OTHER INFORMATION: Immunogen-coil

<400> SEQUENCE: 87

Glu Gly Pro Trp Leu Glu Glu Glu Glu Ala Tyr Gly Gly Gly Ser
1               5                   10                  15

Gly Gly Lys Val Ser Ala Leu Lys Glu Lys Val Ser Ala Leu Lys Glu
            20                  25                  30

Lys Val Ser Ala Leu Lys Glu Lys Val Ser Ala Leu Lys Glu Lys Val
                35                  40                  45

Ser Ala Leu Lys Glu
        50

<210> SEQ ID NO 88
<211> LENGTH: 56
<212> TYPE: PRT
<213> ORGANISM: artificial sequence
<220> FEATURE:
<223> OTHER INFORMATION: Immunogen-coil
<220> FEATURE:
<221> NAME/KEY: PEPTIDE
<222> LOCATION: (16)..(16)
<223> OTHER INFORMATION: Wherein the peptide of the sequence
      EGPWLEEEEEAYGGG is further linked via the C-terminal G to the K at
      position 16

<400> SEQUENCE: 88

Glu Gly Pro Trp Leu Glu Glu Glu Glu Ala Tyr Gly Gly Gly Lys
1               5                   10                  15

Gly Gly Ser Gly Gly Lys Val Ser Ala Leu Lys Glu Lys Val Ser Ala
            20                  25                  30

Leu Lys Glu Lys Val Ser Ala Leu Lys Glu Lys Val Ser Ala Leu Lys
        35                  40                  45

Glu Lys Val Ser Ala Leu Lys Glu
    50                  55

<210> SEQ ID NO 89
<211> LENGTH: 5
<212> TYPE: PRT
<213> ORGANISM: artificial sequence
<220> FEATURE:
<223> OTHER INFORMATION: Peptide

<400> SEQUENCE: 89

Gly Gly Ser Gly Gly
1               5

<210> SEQ ID NO 90
<211> LENGTH: 8
<212> TYPE: PRT
<213> ORGANISM: artificial sequence
<220> FEATURE:
<223> OTHER INFORMATION: Peptide
<220> FEATURE:
<221> NAME/KEY: PEPTIDE
<222> LOCATION: (3)..(3)
<223> OTHER INFORMATION: Wherein the peptide of the sequence GG is
``` further linked via the C-terminal G to the K at position 3.

<400> SEQUENCE: 90

Gly Gly Lys Gly Gly Ser Gly Gly
1               5

<210> SEQ ID NO 91
<211> LENGTH: 5
<212> TYPE: PRT
<213> ORGANISM: artificial sequence
<220> FEATURE:
<223> OTHER INFORMATION: Peptide

<400> SEQUENCE: 91

Glu Ile Ala Ala Leu
1               5

<210> SEQ ID NO 92
<211> LENGTH: 5
<212> TYPE: PRT
<213> ORGANISM: artificial sequence
<220> FEATURE:
<223> OTHER INFORMATION: Peptide

<400> SEQUENCE: 92

Lys Ile Ala Ala Leu
1               5

<210> SEQ ID NO 93
<211> LENGTH: 5
<212> TYPE: PRT
<213> ORGANISM: artificial sequence
<220> FEATURE:
<223> OTHER INFORMATION: Peptide

<400> SEQUENCE: 93

Glu Ile Ser Ala Leu
1               5

<210> SEQ ID NO 94
<211> LENGTH: 5
<212> TYPE: PRT
<213> ORGANISM: artificial sequence
<220> FEATURE:
<223> OTHER INFORMATION: Peptide

<400> SEQUENCE: 94

Lys Ile Ser Ala Leu
1               5

<210> SEQ ID NO 95
<211> LENGTH: 5
<212> TYPE: PRT
<213> ORGANISM: artificial sequence
<220> FEATURE:
<223> OTHER INFORMATION: Peptide

<400> SEQUENCE: 95

Glu Val Ala Ala Leu
1               5

<210> SEQ ID NO 96
<211> LENGTH: 5
<212> TYPE: PRT
<213> ORGANISM: artificial sequence
<220> FEATURE:
<223> OTHER INFORMATION: Peptide

<400> SEQUENCE: 96

Lys Val Ala Ala Leu
1               5

<210> SEQ ID NO 97
<211> LENGTH: 5
<212> TYPE: PRT
<213> ORGANISM: artificial sequence
<220> FEATURE:
<223> OTHER INFORMATION: Peptide

<400> SEQUENCE: 97

Glu Val Ser Ala Leu
1               5

<210> SEQ ID NO 98
<211> LENGTH: 5
<212> TYPE: PRT
<213> ORGANISM: artificial sequence
<220> FEATURE:
<223> OTHER INFORMATION: Peptide

<400> SEQUENCE: 98

Lys Val Ser Ala Leu
1               5

<210> SEQ ID NO 99
<211> LENGTH: 13
<212> TYPE: PRT
<213> ORGANISM: artificial sequence
<220> FEATURE:
<223> OTHER INFORMATION: Immunogen

<400> SEQUENCE: 99

Glu Gly Pro Trp Met Glu Glu Glu Ala Ala Tyr Gly
1               5                   10

<210> SEQ ID NO 100
<211> LENGTH: 13
<212> TYPE: PRT
<213> ORGANISM: artificial sequence
<220> FEATURE:
<223> OTHER INFORMATION: Immunogen

<400> SEQUENCE: 100

Glu Arg Pro Arg Met Glu Glu Glu Ala Tyr Gly
1               5                   10

<210> SEQ ID NO 101
<211> LENGTH: 53
<212> TYPE: PRT
<213> ORGANISM: artificial sequence
<220> FEATURE:
<223> OTHER INFORMATION: Immunogen-coil

<400> SEQUENCE: 101

Glu Gly Pro Trp Met Glu Glu Glu Ala Ala Tyr Gly Gly Gly Ser
1               5                   10                  15

Gly Gly Lys Val Ser Ala Leu Lys Glu Lys Val Ser Ala Leu Lys Glu
            20                  25                  30

Lys Val Ser Ala Leu Lys Glu Lys Val Ser Ala Leu Lys Glu Lys Val
        35                  40                  45

Ser Ala Leu Lys Glu
    50

<210> SEQ ID NO 102
<211> LENGTH: 53
<212> TYPE: PRT
<213> ORGANISM: artificial sequence
<220> FEATURE:
<223> OTHER INFORMATION: Immunogen-coil

<400> SEQUENCE: 102

Glu Gly Pro Trp Leu Glu Glu Glu Glu Ala Tyr Gly Gly Gly Ser
1               5                   10                  15

Gly Gly Lys Val Ser Ala Leu Lys Glu Lys Val Ser Ala Leu Lys Glu
            20                  25                  30

Lys Val Ser Ala Leu Lys Glu Lys Val Ser Ala Leu Lys Glu Lys Val
        35                  40                  45

Ser Ala Leu Lys Glu
    50

<210> SEQ ID NO 103
<211> LENGTH: 56
<212> TYPE: PRT
<213> ORGANISM: artificial sequence
<220> FEATURE:
<223> OTHER INFORMATION: Peptide
<220> FEATURE:
<221> NAME/KEY: PEPTIDE
<222> LOCATION: (16)..(16)
<223> OTHER INFORMATION: Wherein the peptide of the sequence
      EGPWMEEEEAAYGGG is further linked via the C-terminal G to the K at
      position 16.

<400> SEQUENCE: 103

Glu Gly Pro Trp Met Glu Glu Glu Glu Ala Ala Tyr Gly Gly Gly Lys
1               5                   10                  15

Gly Gly Ser Gly Gly Lys Val Ser Ala Leu Lys Glu Lys Val Ser Ala
            20                  25                  30

Leu Lys Glu Lys Val Ser Ala Leu Lys Glu Lys Val Ser Ala Leu Lys
        35                  40                  45

Glu Lys Val Ser Ala Leu Lys Glu
    50                  55

<210> SEQ ID NO 104
<211> LENGTH: 26
<212> TYPE: PRT
<213> ORGANISM: artificial sequence
<220> FEATURE:
<223> OTHER INFORMATION: Peptide

<400> SEQUENCE: 104

Ala Val Asn Ile Val Gly Tyr Ser Asn Ala Gln Gly Val Asp Tyr Trp
1               5                   10                  15

Ile Val Arg Asn Ser Trp Asp Thr Asn Trp
            20                  25

<210> SEQ ID NO 105
<211> LENGTH: 18
<212> TYPE: PRT
<213> ORGANISM: artificial sequence
<220> FEATURE:
<223> OTHER INFORMATION: Peptide

<400> SEQUENCE: 105

Tyr His Asn Pro His Phe Ile Gly Asn Arg Ser Val Ile Thr His Leu
1               5                   10                  15

Met Glu

<210> SEQ ID NO 106
<211> LENGTH: 16
<212> TYPE: PRT
<213> ORGANISM: artificial sequence
<220> FEATURE:
<223> OTHER INFORMATION: Peptide

<400> SEQUENCE: 106

Ser Trp Asp Pro Tyr Trp Pro Phe Pro Trp Phe Ser Gly Gly Gly Ser
1               5                   10                  15

<210> SEQ ID NO 107
<211> LENGTH: 11
<212> TYPE: PRT
<213> ORGANISM: artificial sequence
<220> FEATURE:
<223> OTHER INFORMATION: Peptide

<400> SEQUENCE: 107

Thr Asp Trp Ser Trp Phe Tyr Gly Gly Gly Ser
1               5                   10

<210> SEQ ID NO 108
<211> LENGTH: 11
<212> TYPE: PRT
<213> ORGANISM: artificial sequence
<220> FEATURE:
<223> OTHER INFORMATION: Peptide

<400> SEQUENCE: 108

Tyr Pro Val Tyr Trp Pro Trp Gly Gly Gly Ser
1               5                   10

<210> SEQ ID NO 109
<211> LENGTH: 11
<212> TYPE: PRT
<213> ORGANISM: artificial sequence
<220> FEATURE:
<223> OTHER INFORMATION: Peptide

<400> SEQUENCE: 109

Glu Trp Trp Phe Tyr Trp Pro Gly Gly Gly Ser
1               5                   10

<210> SEQ ID NO 110
<211> LENGTH: 11
<212> TYPE: PRT
<213> ORGANISM: artificial sequence
<220> FEATURE:
<223> OTHER INFORMATION: Peptide

<400> SEQUENCE: 110

Trp Phe Pro Ile Glu Trp Trp Gly Gly Gly Ser
1               5                   10

<210> SEQ ID NO 111
<211> LENGTH: 11
<212> TYPE: PRT
<213> ORGANISM: artificial sequence
<220> FEATURE:
<223> OTHER INFORMATION: Peptide

<400> SEQUENCE: 111

Asp Gln Val Asp Ile Gly Tyr Gly Gly Gly Ser

```
1               5                  10
```

<210> SEQ ID NO 112
<211> LENGTH: 11
<212> TYPE: PRT
<213> ORGANISM: artificial sequence
<220> FEATURE:
<223> OTHER INFORMATION: Peptide

<400> SEQUENCE: 112

```
Thr His Gln Val Tyr Ile Ser Gly Gly Gly Ser
1               5                  10
```

<210> SEQ ID NO 113
<211> LENGTH: 15
<212> TYPE: PRT
<213> ORGANISM: artificial sequence
<220> FEATURE:
<223> OTHER INFORMATION: Peptide

<400> SEQUENCE: 113

```
Trp Phe Pro Ile Glu Trp Trp Phe Tyr Trp Pro Gly Gly Gly Ser
1               5                  10                  15
```

<210> SEQ ID NO 114
<211> LENGTH: 16
<212> TYPE: PRT
<213> ORGANISM: artificial sequence
<220> FEATURE:
<223> OTHER INFORMATION: Peptide

<400> SEQUENCE: 114

```
Asp Ser Trp Gln Ala Phe Leu Thr Lys Phe Val Leu Gly Gly Gly Ser
1               5                  10                  15
```

<210> SEQ ID NO 115
<211> LENGTH: 16
<212> TYPE: PRT
<213> ORGANISM: artificial sequence
<220> FEATURE:
<223> OTHER INFORMATION: Peptide

<400> SEQUENCE: 115

```
Glu Ser Trp Asp Lys Phe Leu Ser His Tyr Leu Pro Gly Gly Gly Ser
1               5                  10                  15
```

<210> SEQ ID NO 116
<211> LENGTH: 16
<212> TYPE: PRT
<213> ORGANISM: artificial sequence
<220> FEATURE:
<223> OTHER INFORMATION: Peptide

<400> SEQUENCE: 116

```
His Asp Ile Gln Trp Phe Trp Gln His Trp Asn Ser Gly Gly Gly Ser
1               5                  10                  15
```

<210> SEQ ID NO 117
<211> LENGTH: 16
<212> TYPE: PRT
<213> ORGANISM: artificial sequence
<220> FEATURE:
<223> OTHER INFORMATION: Peptide

<400> SEQUENCE: 117

```
Trp Ser Trp Trp Asp His Thr Phe Asn Tyr Met Leu Gly Gly Gly Ser
1               5                  10                  15
```

<210> SEQ ID NO 118
<211> LENGTH: 16
<212> TYPE: PRT
<213> ORGANISM: artificial sequence
<220> FEATURE:
<223> OTHER INFORMATION: Peptide

<400> SEQUENCE: 118

Thr Thr Gln Gln Thr Trp Asn Val Arg Tyr Pro Tyr Gly Gly Gly Ser
1               5                   10                  15

<210> SEQ ID NO 119
<211> LENGTH: 16
<212> TYPE: PRT
<213> ORGANISM: artificial sequence
<220> FEATURE:
<223> OTHER INFORMATION: Peptide

<400> SEQUENCE: 119

Asp His Thr Met Pro Trp Thr Arg Asn Ala Lys Asn Gly Gly Gly Ser
1               5                   10                  15

<210> SEQ ID NO 120
<211> LENGTH: 16
<212> TYPE: PRT
<213> ORGANISM: artificial sequence
<220> FEATURE:
<223> OTHER INFORMATION: Peptide

<400> SEQUENCE: 120

Ala Ile Tyr Tyr Val Pro Ser Pro Met Phe Thr Val Gly Gly Gly Ser
1               5                   10                  15

<210> SEQ ID NO 121
<211> LENGTH: 16
<212> TYPE: PRT
<213> ORGANISM: artificial sequence
<220> FEATURE:
<223> OTHER INFORMATION: Peptide

<400> SEQUENCE: 121

Glu Thr Thr Leu Leu Lys Met Trp Leu Ala Gln Met Gly Gly Gly Ser
1               5                   10                  15

<210> SEQ ID NO 122
<211> LENGTH: 16
<212> TYPE: PRT
<213> ORGANISM: artificial sequence
<220> FEATURE:
<223> OTHER INFORMATION: Peptide

<400> SEQUENCE: 122

Tyr Pro Trp Leu Asp Val Ala Val Val Ser Leu Tyr Gly Gly Gly Ser
1               5                   10                  15

<210> SEQ ID NO 123
<211> LENGTH: 16
<212> TYPE: PRT
<213> ORGANISM: artificial sequence
<220> FEATURE:
<223> OTHER INFORMATION: Peptide

<400> SEQUENCE: 123

Val Pro Gly Trp His Tyr Leu Ala Thr Leu Arg Ala Gly Gly Gly Ser
1               5                   10                  15

```
<210> SEQ ID NO 124
<211> LENGTH: 16
<212> TYPE: PRT
<213> ORGANISM: artificial sequence
<220> FEATURE:
<223> OTHER INFORMATION: Peptide

<400> SEQUENCE: 124

Phe Asp Pro Leu Gly Ser Arg Asp Ile Lys Gly Ser Gly Gly Gly Ser
1               5                   10                  15

<210> SEQ ID NO 125
<211> LENGTH: 3
<212> TYPE: PRT
<213> ORGANISM: artificial sequence
<220> FEATURE:
<223> OTHER INFORMATION: Peptide

<400> SEQUENCE: 125

Glu Trp Trp
1

<210> SEQ ID NO 126
<211> LENGTH: 3
<212> TYPE: PRT
<213> ORGANISM: artificial sequence
<220> FEATURE:
<223> OTHER INFORMATION: Peptide

<400> SEQUENCE: 126

Trp Phe Tyr
1

<210> SEQ ID NO 127
<211> LENGTH: 3
<212> TYPE: PRT
<213> ORGANISM: artificial sequence
<220> FEATURE:
<223> OTHER INFORMATION: Peptide

<400> SEQUENCE: 127

Tyr Trp Pro
1

<210> SEQ ID NO 128
<211> LENGTH: 4
<212> TYPE: PRT
<213> ORGANISM: artificial sequence
<220> FEATURE:
<223> OTHER INFORMATION: Peptide
<220> FEATURE:
<221> NAME/KEY: PEPTIDE
<222> LOCATION: (3)..(3)
<223> OTHER INFORMATION: X being any amino acid

<400> SEQUENCE: 128

Gln Val Xaa Ile
1
```